United States Patent
Wang et al.

(10) Patent No.: US 10,758,544 B2
(45) Date of Patent: Sep. 1, 2020

(54) PHARMACEUTICAL COMPOSITIONS AND METHODS OF TREATING CARDIOVASCULAR DISEASES

(71) Applicant: Cardix Therapeutics LLC, San Diego, CA (US)

(72) Inventors: Jin Jean Wang, San Diego, CA (US); Gerald J. Yakatan, Del Mar, CA (US); Ting N. Lin, Bengbu (CN); Jing H. Gao, Bengbu (CN)

(73) Assignee: CARDIX Therapeutics, LLC, San Diego, CA (US)

( * ) Notice: Subject to any disclaimer, the term of this patent is extended or adjusted under 35 U.S.C. 154(b) by 0 days.

(21) Appl. No.: 16/353,675

(22) Filed: Mar. 14, 2019

(65) Prior Publication Data

US 2019/0231786 A1     Aug. 1, 2019

Related U.S. Application Data

(62) Division of application No. 15/973,132, filed on May 7, 2018.

(60) Provisional application No. 62/652,812, filed on Apr. 4, 2018, provisional application No. 62/503,902, filed on May 9, 2017.

(51) Int. Cl.

| | |
|---|---|
| *A61K 31/522* | (2006.01) |
| *A61K 31/4422* | (2006.01) |
| *A61K 31/4402* | (2006.01) |
| *A61P 9/06* | (2006.01) |
| *A61K 31/575* | (2006.01) |
| *A61K 31/455* | (2006.01) |
| *A61K 31/46* | (2006.01) |
| *A61K 31/137* | (2006.01) |

(52) U.S. Cl.
CPC .......... *A61K 31/522* (2013.01); *A61K 31/137* (2013.01); *A61K 31/4402* (2013.01); *A61K 31/4422* (2013.01); *A61K 31/455* (2013.01); *A61K 31/46* (2013.01); *A61K 31/575* (2013.01); *A61P 9/06* (2018.01)

(58) Field of Classification Search
USPC ....................................................... 514/171
See application file for complete search history.

(56) References Cited

FOREIGN PATENT DOCUMENTS

| | | |
|---|---|---|
| JP | 2019-515882 | 3/2019 |
| RU | 2115419 | 4/2019 |
| TW | 1657826 | 10/2018 |

OTHER PUBLICATIONS

Ling (Theophylline for Chronic Symptomatic Bradycardia in the Elderly, The Annals of Pharmacotherapy • Jul./Aug. 1998, vol. 32, pp. 837-839).*
Schoffstall (Effects of calcium channel blocker overdose-induced toxicity in the conscious dog, Annal of Emergency Medicine, vol. 20, Issue 10, Oct. 1991, pp. 1104-1108).*
Betahistine (Betahistine side effect anyone??, https//ehealthforum.com/health/topic55452.html, pp. 1-5).*
Kelly (A Comparison of Heart Rate Changes Associated with Levalbuterol and Racemic Albuterol in Pediatric Cardiology Patients, Annals of Pharmacotherapy, Apr. 2013, https://journals.sagepub.com/doi/full/10.1345/aph.1S003?url_ver=Z39.88/2003&rfr_id=or &).*
Cardix Therapeutics LLC, Report for a Single Ascending Dose Clinical Study to Establish Safety and tolerability of Cardix-101 in Bradycardia Patients, Jun. 2020, IND # 131175.

* cited by examiner

*Primary Examiner* — Kathrien A Cruz
(74) *Attorney, Agent, or Firm* — Michael L. Greenberg, Esq.; Greenberg & Lieberman, LLC

(57) ABSTRACT

Provided herein is a pharmaceutical composition comprising two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist. Also provided herein is a method of treating, preventing, or ameliorating a cardiovascular disease in a subject, comprising administering to the subject in need thereof two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

10 Claims, No Drawings

PHARMACEUTICAL COMPOSITIONS AND METHODS OF TREATING CARDIOVASCULAR DISEASES

CROSS REFERENCE TO RELATED APPLICATIONS

This application is a divisional application which is directed to non-provisional application Ser. No. 15/973,132, filed on May 7, 2018, directed to U.S. Provisional Application No. 62/503,902, filed May 9, 2017, and U.S. Provisional Application No. 62/652,812, filed Apr. 4, 2018, the disclosure of each of which is incorporated herein by reference in its entirety.

FIELD

Provided herein is a pharmaceutical composition comprising two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist. Also provided herein is a method of treating, preventing, or ameliorating a cardiovascular disease in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

BACKGROUND

Cardiovascular diseases are a class of diseases that involve the heart or blood vessels. Mendis et al., *Global Atlas on Cardiovascular Disease Prevention and Control—World Health Organization, World Heart Federation, and World Stroke Organization* 2011. Cardiovascular diseases include coronary artery diseases such as angina and myocardial infarction (commonly known as heart attack), stroke, hypertensive heart disease, rheumatic heart disease, cardiomyopathy, cardiac arrhythmia, congenital heart disease, valvular heart disease, carditis, aortic aneurysms, peripheral artery disease, and venous thrombosis. Id.; *Lancet* 2014, 385, 117-171. Cardiovascular diseases are the leading cause of death globally. Mendis et al., *Global Atlas on Cardiovascular Disease Prevention and Control—World Health Organization, World Heart Federation, and World Stroke Organization* 2011. In 2013, cardiovascular diseases resulted in 17.3 million deaths (31.5%), up from 12.3 million (25.8%) in 1990. *Lancet* 2014, 385, 117-171. In the United States, 11% of people between 20 and 40 have a cardiovascular disease, while 37% between 40 and 60, 71% of people between 60 and 80, and 85% of people over 80 have a cardiovascular disease. Go et al., *Circulation* 2013, 127, e6-e245.

One form of cardiac arrhythmia is bradycardia, a slow heart rate condition, which can cause fainting, dizziness, malaise, general weakness, excessive fatigue, chest pain, or failing memory. With no approved drug therapy available for effective treatment of chronic bradycardia, a cardiac pacemaker must often be installed into a patient to sustain his/her life. Although several studies had investigated potential therapy with some drugs (Alboni et al., *Am. J. Cardiol.* 1990, 65, 1037-1039; Ling et al., *Ann. Pharmacother.* 1998, 32, 837-839; Benditt et al., *Am. J. Cardiol.* 1983, 52, 1223-229), the adverse side effects at therapeutic doses prevent routine, long-term use of these previously tested drug candidates. Thus, currently, there is no approved drug worldwide for treating bradycardia. The treatment of choice for chronic, symptomatic bradycardia is limited to the implantation of a cardiac pacemaker. It is estimated that the United States and Europe, as well as other advanced countries, have a rate of pacemaker implantation of about 50-60/100,000 people per annum. A worldwide survey published in 2009 indicates that approximately one million pacemaker implantations (approximately 740,000 new implants) were performed in the 61 countries responding to the survey. By 2028, it is estimated that over 700,000 new pacemaker implantations will be done in the US alone. The 10-year prevalence (US 1999-2008) of clinically defined bradycardia (abnormally slow heart rate, RPR (resting pulse rate)<60 beats/min) is 15.2% for male adults and 6.9% for females. *US National Health Statistics Reports* 2011, 41, 1-16. Since the human pulse rate is inversely associated with age and the aged population is increasing worldwide, there will be a continually increasing number of patients with bradycardia requiring pacemaker implants. Furthermore, due to the adverse side effects and high cost of pacemakers, many bradycardia patients either cannot or elect not to have a pacemaker implanted even when needed from a medical perspective.

As noted, current medical treatment for bradycardia requires a surgical insertion of a cardiac pacemaker. The first use of a buried cardiac pacemaker occurred in Sweden in 1958. Since then, this approach for the treatment of abnormal cardiac rhythms has gradually spread all over the world. In recent years, the quality of pacemakers has improved; and as a result, the use of pacemakers to treat bradycardia has greatly increased. Unfortunately, cardiac pacemakers have some limitations. For example, pacemakers require a surgical procedure for implantation in the human body, and infections requiring device removal do occur with a finite frequency. In addition, pacemakers may not provide a normal physiological heart rate response to exertion or a normal contractile pattern. Because of inadequate or inappropriate heart rate response during exertion, patients may develop significant symptoms related to inadequate cardiac output. In addition, pacing the right ventricle only (as occurs with single or dual chamber pacemakers) may lead to significant left ventricular dysfunction and worsening of heart failure in some patients. Left ventricular failure associated with right ventricular pacing may be ameliorated by implantation of a bi-ventricular pacemaker, but this procedure is time consuming, difficult, and not always possible due to technical issues. As has been recently observed, pacemakers and pacemaker leads may fail and are subject to periodic recalls by sovereign regulatory agencies such as the FDA. Finally, the costs of pacemaker implantation, replacement and follow up are high. Nonetheless, in the absence of a reasonable alternative treatment for bradycardia, doctors and patients usually opt to use a pacemaker when it is necessary. Furthermore, many bradycardia patients delay or forgo the pacemaker surgery due to the potential complications discussed herein and choose to live with bradycardia and the associated potentially fatal medical risks instead. Therefore, there is an unmet need for an effective drug therapy for treating bradycardia.

SUMMARY OF THE DISCLOSURE

To overcome the deficiencies associated with current treatments of bradycardia, provided herein are methods and pharmaceutical compositions useful for treating bradycardia and associated cardiovascular diseases.

Provided herein is a pharmaceutical composition comprising (a) two or more compounds, wherein each compound in the pharmaceutical composition is independently (i) a phosphodiesterase inhibitor or an adenosine receptor antagonist, (ii) a calcium channel blocker, (iii) a histamine $H_1$-receptor agonist, a histamine $H_2$-receptor agonist, or a histamine $H_3$-receptor antagonist, or (iv) a $\beta_2$-adrenoreceptor agonist; and (b) a pharmaceutically acceptable excipient.

Also provided herein is a pharmaceutical composition comprising (a) three or more compounds, wherein each compound in the pharmaceutical composition is independently (i) a phosphodiesterase inhibitor or an adenosine receptor antagonist, (ii) a calcium channel blocker, (iii) a histamine $H_1$-receptor agonist, a histamine $H_2$-receptor agonist, or a histamine $H_3$-receptor antagonist, or (iv) a $\beta_2$-adrenoreceptor agonist; and (b) a pharmaceutically acceptable excipient.

Furthermore provided herein is a pharmaceutical composition comprising (i) a phosphodiesterase inhibitor or an adenosine receptor antagonist; (ii) a calcium channel blocker; (iii) a histamine $H_1$-receptor agonist, a histamine $H_2$-receptor agonist, or a histamine $H_3$-receptor antagonist; or (iv) a $\beta_2$-adrenoreceptor agonist.

Additionally provided herein is a pharmaceutical composition comprising (i) a phosphodiesterase inhibitor or an adenosine receptor antagonist; (ii) a calcium channel blocker; and (iii) a histamine $H_1$-receptor agonist, a histamine $H_2$-receptor agonist, or a histamine $H_3$-receptor antagonist.

Provided herein is a pharmaceutical composition comprising (i) a phosphodiesterase inhibitor or an adenosine receptor antagonist; (ii) a calcium channel blocker; and (iii) a $\beta_2$-adrenoreceptor agonist.

Provided herein is a pharmaceutical composition comprising (i) a phosphodiesterase inhibitor or an adenosine receptor antagonist; (ii) a histamine $H_1$-receptor agonist, a histamine $H_2$-receptor agonist, or a histamine $H_3$-receptor antagonist; and (iii) a $\beta_2$-adrenoreceptor agonist.

Provided herein is a pharmaceutical composition comprising (i) a phosphodiesterase inhibitor or an adenosine receptor antagonist; (ii) a calcium channel blocker; (iii) a histamine $H_1$-receptor agonist, a histamine $H_2$-receptor agonist, or a histamine $H_3$-receptor antagonist; and (iv) a $\beta_2$-adrenoreceptor agonist.

Provided herein is a pharmaceutical composition comprising (a) two or more compounds, wherein each compound is independently (i) a phosphodiesterase inhibitor or an adenosine receptor antagonist, in one embodiment, theophylline, aminophylline, or an isotopic variant thereof, in the amount ranging from about 5 to about 90% or from about 5 to about 35% by weight; (ii) a calcium channel blocker, in one embodiment, nifedipine or an isotopic variant thereof, in the amount ranging from about 1 to about 20% or from about 1 to about 5% by weight; (iii) a histamine $H_1$-receptor agonist, a histamine $H_2$-receptor agonist, or a histamine $H_3$-receptor antagonist, in one embodiment, betahistine dihydrochloride or an isotopic variant thereof, in the amount ranging from about 0.1 to about 20% or from about 0.5 to about 5% by weight; or (iv) a $\beta_2$-adrenoreceptor agonist, in one embodiment, albuterol, levalbuterol hydrochloride, or an isotopic variant thereof, in the amount ranging from about 0.01 to about 5% or from about 0.1 to about 0.5% by weight; and (b) a pharmaceutically acceptable excipient.

Provided herein is a pharmaceutical composition comprising (a) three or more compounds, wherein each compound is independently (i) a phosphodiesterase inhibitor or an adenosine receptor antagonist, in one embodiment, theophylline, aminophylline, or an isotopic variant thereof, in the amount ranging from about 5 to about 90% or from about 5 to about 35% by weight; (ii) a calcium channel blocker, in one embodiment, nifedipine or an isotopic variant thereof, in the amount ranging from about 1 to about 20% or from about 1 to about 5% by weight; (iii) a histamine $H_1$-receptor agonist, a histamine $H_2$-receptor agonist, or a histamine $H_3$-receptor antagonist, in one embodiment, betahistine dihydrochloride or an isotopic variant thereof, in the amount ranging from about 0.1 to about 20% or from about 0.5 to about 5% by weight; and (iv) a $\beta_2$-adrenoreceptor agonist, in one embodiment, albuterol, levalbuterol hydrochloride, or an isotopic variant thereof, in the amount ranging from about 0.01 to about 5% or from about 0.1 to about 0.5% by weight; and (b) a pharmaceutically acceptable excipient.

Provided herein is a method of treating, preventing, or ameliorating a cardiovascular diseases in a subject, comprising administering to the subject in need thereof a therapeutically effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of treating, preventing, or ameliorating symptomatic sinus bradycardia in a subject, comprising administering to the subject in need thereof a therapeutically effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of treating, preventing, or ameliorating stroke in a subject, comprising administering to the subject in need thereof a therapeutically effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of treating, preventing, or ameliorating cerebral vascular thrombosis in a subject, comprising administering to the subject in need thereof a therapeutically effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of treating, preventing, or ameliorating abnormal heart rhythm in a subject, comprising administering to the subject in need thereof a therapeutically effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of increasing heart rate in a subject, comprising administering to the subject in need thereof an effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of increasing cardiac output in a subject, comprising administering to the subject in need thereof an effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Provided herein is a method of increasing cerebral blood flow in a subject, comprising administering to the subject in need thereof an effective amount of two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

DETAILED DESCRIPTION

To facilitate understanding of the disclosure set forth herein, a number of terms are defined below.

Generally, the nomenclature used herein and the laboratory procedures in medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "subtherapeutically effective amount" of a compound refers to a dose lower than the amount that is effective when the compound is administered alone.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, Pa., 2012; *Handbook of Pharmaceutical Excipients,* 7th ed.; Rowe et al., Eds.; The Pharmaceutical Press and the American Pharmaceutical Association: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient," "active pharmaceutical ingredient," "API," and "active substance" are used interchangeably herein in reference to a compound, which is administered, alone or in combination with one or more pharmaceutically acceptable excipients, to a subject for treating, preventing, or ameliorating one or more symptoms of a disorder, disease, or condition. As used herein, "active ingredient," "active pharmaceutical ingredient," "API," and "active substance" may be a metabolite and/or an isotopic variant and/or an optically active isomer of a compound described herein.

The term "isotopically enriched" or "isotopic variant" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$) and iodine-131 ($^{131}I$). It will be understood that, in a compound as provided herein, any hydrogen can be $^2H$, as example, or any carbon can be $^{13}C$, as example, or any nitrogen can be $^{15}N$, as example, or any oxygen can be $^{18}O$, as example, where feasible according to the judgment of one of skill.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopic enrichment" refers to the percentage of incorporation of a less prevalent isotope (e.g., D for hydrogen) of an element at a given position in a molecule in the place of a more prevalent isotope (e.g., $^1H$ for hydrogen) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1H$), deuterium ($^2H$ or D), and tritium ($^3H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable salt, solvate, hydrate, or prodrug thereof" has the same meaning as the phrase "(i) an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of an isotopic variant of the compound referenced therein."

Pharmaceutical Compositions

In an embodiment, provided herein are pharmaceutical compositions useful for treating symptomatic sinus bradycardia. In some embodiments, provided herein is a pharmaceutical composition comprising two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

The present disclosure discloses a surprising benefit associated with a combination of two or more active pharmaceutical ingredients (API) provided herein for treating a cardiovascular disease, e.g., bradycardia. Specifically, without being bound by theory, the combination of two or more APIs provided herein utilizes a secondary therapeutical effect (e.g., an undesired side effect associated with the currently approved indication(s)) of each API at a subtherapeutically effective amount to elicit/enhance a desired therapeutical effect, such as increased heart rate and/or increased cardiac output; and such desired therapeutical effect is useful to treat a cardiovascular disease, such as heart failure associated with abnormal cardiac output or bradycardia. Without being bound by theory, the combination of two or more APIs provided herein takes advantage of counteracting adverse side effects of each API such as increased/decreased oxygen consumption and increased/reduced blood pressure. As a result, the APIs when taken in a combination provided herein achieve desired therapeutical effects, including increased heart rate and cardiac output in patients with minimized adverse side effects or without undesired adverse side effects such as increased oxygen consumption or elevated blood pressure associated with an API when taken alone. The combination provided herein combines two or more APIs that all possess the same desired secondary therapeutic effects of increasing heart rate and cardiac output, where the undesired side effects of one API are counteracted by the side effects from another API in the combination. Furthermore, by reducing the amount of each API to a subtherapeutically effective amount, the undesired adverse side effects of each API are further reduced.

In one embodiment, provided herein is a pharmaceutical composition comprising two compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a phosphodiesterase inhibitor or an adenosine receptor antagonist; and (ii) a calcium channel blocker. In another embodiment, the pharmaceutical composition comprises (i) a phosphodiesterase inhibitor or an adenosine receptor antagonist; and (ii) a histamine $H_1$-receptor agonist, a histamine $H_2$-receptor agonist, or a histamine $H_3$-receptor antagonist. In yet another embodiment, the pharmaceutical composition comprises (i) a phosphodiesterase inhibitor or an adenosine receptor antagonist; and (ii) a $\beta_2$-adrenoreceptor agonist. In yet another embodiment, the pharmaceutical composition comprises (i) a calcium channel blocker; and (ii) a histamine $H_1$-receptor agonist, a histamine $H_2$-receptor agonist, or a histamine $H_3$-receptor antagonist. In yet another embodiment, the pharmaceutical composition comprises (i) a calcium channel blocker; and (ii) a $\beta_2$-adrenoreceptor agonist. In still another embodiment, the pharmaceutical composition comprises (i) a histamine $H_1$-receptor agonist, a histamine $H_2$-receptor agonist, or a histamine $H_3$-receptor antagonist; and (ii) a $\beta_2$-adrenoreceptor agonist.

In yet another embodiment, provided herein is a pharmaceutical composition comprising three compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a phosphodiesterase inhibitor or an adenosine receptor antagonist; (ii) a calcium channel blocker; and (iii) a histamine $H_1$-receptor agonist, a histamine $H_2$-receptor agonist, or a histamine $H_3$-receptor antagonist. In another embodiment, the pharmaceutical composition comprises (i) a phosphodiesterase inhibitor or an adenosine receptor antagonist; (ii) a calcium channel blocker; and (iii) a $\beta_2$-adrenoreceptor agonist. In yet another embodiment, the pharmaceutical composition comprises (i) a calcium channel blocker; (ii) a histamine $H_1$-receptor agonist, a histamine $H_2$-receptor agonist, or a histamine $H_3$-receptor antagonist; and (iii) a $\beta_2$-adrenoreceptor agonist. In yet another embodiment, the pharmaceutical composition comprises (i) a phosphodiesterase inhibitor or an adenosine receptor antagonist; (ii) a histamine $H_1$-receptor agonist, a histamine $H_2$-receptor agonist, or a histamine $H_3$-receptor antagonist; and (iii) a $\beta_2$-adrenoreceptor agonist.

In still another embodiment, provided herein is a pharmaceutical composition comprising four compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition provided herein comprises: (i) a phosphodiesterase inhibitor or an adenosine receptor antagonist; (ii) a calcium channel blocker; (iii) a histamine $H_1$-receptor agonist, a histamine $H_2$-receptor agonist, or a histamine $H_3$-receptor antagonist; and (iv) $\beta_2$-adrenoreceptor agonist.

In certain embodiments, the phosphodiesterase inhibitor or adenosine receptor antagonist is a solid. In certain embodiments, the phosphodiesterase inhibitor or adenosine receptor antagonist is a crystalline solid. In certain embodiments, the phosphodiesterase inhibitor or adenosine receptor antagonist is an amorphous solid.

In certain embodiments, the calcium channel blocker is a solid. In certain embodiments, the calcium channel blocker is a crystalline solid. In certain embodiments, the calcium channel blocker is an amorphous solid.

In certain embodiments, the histamine $H_1$-receptor agonist, the histamine $H_2$-receptor agonist, or the histamine $H_3$-receptor antagonist is a solid. In certain embodiments, the histamine $H_1$-receptor agonist, the histamine $H_2$-receptor agonist, or the histamine $H_3$-receptor antagonist is a crystalline solid. In certain embodiments, the histamine $H_1$-receptor agonist, the histamine $H_2$-receptor agonist, or the histamine $H_3$-receptor antagonist is an amorphous solid.

In certain embodiments, the $\beta_2$-adrenoreceptor agonist is a solid. In certain embodiments, the $\beta_2$-adrenoreceptor agonist is a crystalline solid. In certain embodiments, the $\beta_2$-adrenoreceptor agonist is an amorphous solid.

In certain embodiments, the weight ratio of (i) the phosphodiesterase inhibitor or adenosine receptor antagonist to (ii) the calcium channel blocker in a pharmaceutical composition provided herein is ranging from about 1 to about 180, from about 2 to about 100, from about 2 to about 50, or from about 2 to about 20. In certain embodiments, the weight ratio of (i) the phosphodiesterase inhibitor or adenosine receptor antagonist to (ii) the calcium channel blocker in a pharmaceutical composition provided herein is ranging from about 1 to about 180. In certain embodiments, the weight ratio of (i) the phosphodiesterase inhibitor or adenosine receptor antagonist to (ii) the calcium channel blocker in a pharmaceutical composition provided herein is ranging from about 2 to about 100. In certain embodiments, the weight ratio of (i) the phosphodiesterase inhibitor or adenosine receptor antagonist to (ii) the calcium channel blocker in a pharmaceutical composition provided herein is ranging from about 2 to about 50. In certain embodiments, the weight ratio of (i) the phosphodiesterase inhibitor or adenosine receptor antagonist to (ii) the calcium channel blocker in a pharmaceutical composition provided herein is ranging from about 2 to about 20. In certain embodiments, the weight ratio of (i) the phosphodiesterase inhibitor or adenosine receptor antagonist to (ii) the calcium channel blocker in a pharmaceutical composition provided herein is about 2, about 4, about 6, about 8, about 10, about 12, about 14, about 16, about 18, or about 20.

In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is ranging from about 2 to about 200, from about 4 to about 100, from about 5 to about 50, or from about 10 to about 30. In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is ranging from about 2 to about 200. In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is ranging from about 4 to about 100. In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is ranging from about 5 to about 50. In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is ranging from about 10 to about 30. In certain embodiments, the weight ratio of (i) the phosphodiesterase inhibitor or adenosine receptor antagonist to (ii) the histamine $H_1$-receptor agonist, the histamine $H_2$-receptor agonist, or the histamine $H_3$-receptor antagonist in a pharmaceutical composition provided herein is about 10, about 12, about 14, about 16, about 18, about 20, about 22, about 24, about 26, about 28, or about 30.

In certain embodiments, the weight ratio of (i) the phosphodiesterase inhibitor or adenosine receptor antagonist to (ii) the $\beta_2$-adrenoreceptor agonist in a pharmaceutical composition provided herein is ranging from about 1 to about 1,000, from about 10 to about 500, from about 20 to about 400, or from about 40 to about 300. In certain embodiments, the weight ratio of (i) the phosphodiesterase inhibitor or adenosine receptor antagonist to (ii) the $\beta_2$-adrenoreceptor agonist in a pharmaceutical composition provided herein is ranging from about 1 to about 1,000. In certain embodiments, the weight ratio of (i) the phosphodiesterase inhibitor or adenosine receptor antagonist to (ii) the $\beta_2$-adrenoreceptor agonist in a pharmaceutical composition provided herein is ranging from about 10 to about 500. In certain embodiments, the weight ratio of (i) the phosphodiesterase inhibitor or adenosine receptor antagonist to (ii) the $\beta_2$-adrenoreceptor agonist in a pharmaceutical composition provided herein is ranging from about 20 to about 400. In certain embodiments, the weight ratio of (i) the phosphodiesterase inhibitor or adenosine receptor antagonist to (ii) the $\beta_2$-adrenoreceptor agonist in a pharmaceutical composition provided herein is ranging from about 40 to about 300. In certain embodiments, the weight ratio of (i) the phosphodiesterase inhibitor or adenosine receptor antagonist to (ii) the $\beta_2$-adrenoreceptor agonist in a pharmaceutical composition provided herein is about 40, about 60, about 80, about 100, about 120, about 140, about 160, about 180, about 200, about 220, about 240, about 260, about 280, or about 300.

In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is ranging from about 1 to about 50, from about 1 to about 40, from about 1 to about 20, or from about 1 to about 10. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is ranging from about 1 to about 50. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is ranging from about 1 to about 40. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is ranging from about 1 to about 20. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is ranging from about 1 to about 10. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10. In certain embodiments, the weight ratio of (i) the calcium channel blocker to (ii) the histamine $H_1$-receptor agonist, the histamine $H_2$-receptor agonist, or the histamine $H_3$-receptor antagonist in a pharmaceutical composition provided herein is about 2, about 2.2, about 2.4, about 2.6, about 2.8, about 3, about 3.2, about 3.4, about 3.6, about 3.8, or about 4.

In certain embodiments, the weight ratio of (i) the calcium channel blocker to (ii) the $\beta_2$-adrenoreceptor agonist in a pharmaceutical composition provided herein is ranging from about 1 to about 100, from about 5 to about 50, or from about 5 to about 30. In certain embodiments, the weight ratio of (i) the calcium channel blocker to (ii) the $\beta_2$-adrenoreceptor agonist in a pharmaceutical composition provided herein is ranging from about 1 to about 100. In certain embodiments, the weight ratio of (i) the calcium channel blocker to (ii) the $\beta_2$-adrenoreceptor agonist in a pharmaceutical composition provided herein is ranging from about 5 to about 50. In certain embodiments, the weight ratio of (i) the calcium channel blocker to (ii) the $\beta_2$-adrenoreceptor agonist in a pharmaceutical composition provided herein is ranging from about 5 to about 30. In certain embodiments, the weight ratio of (i) the calcium channel blocker to (ii) the $\beta_2$-adrenoreceptor agonist in a pharmaceutical composition provided herein is about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is ranging from about 1 to about 100, from about 1 to about 50, from about 1 to about 30, or from about 1 to about 20. In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is ranging from about 1 to about 100. In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is ranging from about 1 to about 50. In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is ranging from about 1 to about 30. In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is ranging from about 1 to about 20. In certain embodiments, the weight ratio of (i) the histamine $H_1$-receptor agonist, the histamine $H_2$-receptor agonist, or the histamine $H_3$-receptor antagonist to (ii) the $\beta_2$-adrenoreceptor agonist in a pharmaceutical composition provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a pharmaceutical composition provided herein comprises a phosphodiesterase inhibitor or an adenosine receptor antagonist in the amount ranging from about 1 to about 1,200, from about 1 to about 1,000, from about 1 to about 800, from about 1 to about 600, from about 2 to about 300, or from about 10 to about 200 mg. In certain embodiments, a pharmaceutical composition provided herein comprises a phosphodiesterase inhibitor or an adenosine receptor antagonist in the amount ranging from about 1 to about 1,200 mg. In certain embodiments, a pharmaceutical composition provided herein comprises a phosphodiesterase inhibitor or an adenosine receptor antagonist in the amount ranging from about 1 to about 1,000 mg. In certain embodiments, a pharmaceutical composition provided herein comprises a phosphodiesterase inhibitor or an adenosine receptor antagonist in the amount ranging from about 1 to about 800 mg. In certain embodiments, a pharmaceutical composition provided herein comprises a phosphodiesterase inhibitor or an adenosine receptor antagonist in the amount ranging from about 1 to about 600 mg. In certain embodiments, a pharmaceutical composition provided herein comprises a phosphodiesterase inhibitor or an adenosine receptor antagonist in the amount ranging from about 2 to about 300 mg. In certain embodiments, a pharmaceutical composition provided herein comprises a phosphodiesterase inhibitor or an adenosine receptor antagonist in the amount ranging from about 10 to about 200 mg. In certain embodiments, a pharmaceutical composition provided herein comprises a phosphodiesterase inhibitor or an adenosine receptor antagonist in the amount of about 20, about 30, about 40, about 50, about 60, about 70, about 80, about 90, about 100, about 110, about 120, about 130, about 140, about 150, about 160, about 170, about 180, about 190, or about 200 mg.

In certain embodiments, a pharmaceutical composition provided herein comprises a calcium channel blocker in the amount ranging from about 0.1 to about 200, from about 0.1 to about 100, from about 0.2 to about 80, from about 1 to about 50, or from about 1 to about 30. In certain embodiments, a pharmaceutical composition provided herein comprises a calcium channel blocker in the amount ranging from about 0.1 to about 200 mg. In certain embodiments, a pharmaceutical composition provided herein comprises a calcium channel blocker in the amount ranging from about 0.1 to about 100 mg. In certain embodiments, a pharmaceutical composition provided herein comprises a calcium channel blocker in the amount ranging from about 0.2 to about 80 mg. In certain embodiments, a pharmaceutical composition provided herein comprises a calcium channel blocker in the amount ranging from about 1 to about 50 mg. In certain embodiments, a pharmaceutical composition provided herein comprises a calcium channel blocker in the amount ranging from about 1 to about 30 mg. In certain embodiments, a pharmaceutical composition provided herein comprises a calcium channel blocker in the amount of about 2, about 4, about 6, about 8, about 10, about 12, about 14, about 16, about 18, about 20, about 22, about 24, about 26, about 28, or about 30 mg.

In certain embodiments, a pharmaceutical composition provided herein comprises a histamine $H_1$-receptor agonist, a histamine $H_2$-receptor agonist, or a histamine $H_3$-receptor antagonist in the amount ranging from about 0.1 to about 200, from about 0.1 to about 100, from about 0.1 to about 60, from about 0.2 to about 50, from about 0.5 to about 40, or from about 1 to about 30 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.1 to about 200 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.1 to about 100 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.1 to about 60 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.2 to about 50 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.5 to about 40 mg. In certain embodiments, a pharmaceutical composition provided herein comprises a histamine $H_1$-receptor agonist, a histamine $H_2$-receptor agonist, or a histamine $H_3$-receptor antagonist in the amount ranging from about 1 to about 3 mg. In certain embodiments, a pharmaceutical composition provided herein comprises a histamine $H_1$-receptor agonist, a histamine $H_2$-receptor agonist, or a histamine $H_3$-receptor antagonist in the amount of about 1, about 5, about 10, about 15, about 20, about 25, or about 30 mg.

In certain embodiments, a pharmaceutical composition provided herein comprises a $\beta_2$-adrenoreceptor agonist in the amount ranging from about 0.01 to about 60, from about 0.01 to about 40, from about 0.05 to about 30, from about 0.05 to about 20, or from about 0.1 to about 10, or from about 0.1 to about 5 mg. In certain embodiments, a pharmaceutical composition provided herein comprises a $\beta_2$-adrenoreceptor agonist in the amount ranging from about 0.01 to about 60 mg. In certain embodiments, a pharmaceutical composition provided herein comprises a $\beta_2$-adrenoreceptor agonist in the amount ranging from about 0.01 to about 40 mg. In certain embodiments, a pharmaceutical composition provided herein comprises a $\beta_2$-adrenoreceptor agonist in the amount ranging from about 0.05 to about 30 mg. In certain embodiments, a pharmaceutical composition provided herein comprises a $\beta_2$-adrenoreceptor agonist in the amount ranging from about 0.05 to about 20 mg. In certain embodiments, a pharmaceutical composition provided herein comprises a $\beta_2$-adrenoreceptor agonist in the amount ranging from about 0.1 to about 10 mg. In certain embodiments, a pharmaceutical composition provided herein comprises a $\beta_2$-adrenoreceptor agonist in the amount ranging from about 0.1 to about 5 mg. In certain embodiments, a pharmaceutical composition provided herein comprises a $\beta_2$-adrenoreceptor agonist in the amount of about 0.1, about 0.5, about 1, about 1.5, about 2, about 2.5, about 3, about 3.5, about 4, about 4.5, or about 5 mg.

In certain embodiments, a pharmaceutical composition provided herein comprises a phosphodiesterase inhibitor or an adenosine receptor antagonist in the amount ranging from about 1 to about 90, from about 2 to about 80, from about 5 to 60, or from about 5 to about 35% by weight. In certain embodiments, a pharmaceutical composition provided herein comprises a phosphodiesterase inhibitor or an adenosine receptor antagonist in the amount ranging from about 1 to about 90% by weight. In certain embodiments, a pharmaceutical composition provided herein comprises a phosphodiesterase inhibitor or an adenosine receptor antagonist in the amount ranging from about 2 to about 80% by weight. In certain embodiments, a pharmaceutical composition provided herein comprises a phosphodiesterase inhibitor or an adenosine receptor antagonist in the amount ranging from about 5 to about 60% by weight. In certain embodiments, a pharmaceutical composition provided herein comprises a phosphodiesterase inhibitor or an adenosine receptor antagonist in the amount ranging from about 5 to about 35% by weight. In certain embodiments, a pharmaceutical composition provided herein comprises a phosphodiesterase inhibitor or an adenosine receptor antagonist in the amount of about 5, about 10, about 15, about 20, about 25, about 30, about 35, about 40, about 45, about 50, about 55, or about 60% by weight.

In certain embodiments, a pharmaceutical composition provided herein comprises a calcium channel blocker in the amount ranging from about 0.1 to about 30, from about 0.5 to about 20, or from about 1 to about 10% by weight. In certain embodiments, a pharmaceutical composition provided herein comprises a calcium channel blocker in the amount ranging from about 0.1 to about 30% by weight. In certain embodiments, a pharmaceutical composition provided herein comprises a calcium channel blocker in the amount ranging from about 0.5 to about 20% by weight. In certain embodiments, a pharmaceutical composition provided herein comprises a calcium channel blocker in the amount ranging from about 1 to about 10% by weight. In certain embodiments, a pharmaceutical composition provided herein comprises a calcium channel blocker in the amount of about 1, about 2, about 3, about 4, about 5, about 6, about 7, about 8, about 9, or about 10% by weight.

In certain embodiments, a pharmaceutical composition provided herein comprises a histamine $H_1$-receptor agonist, a histamine $H_2$-receptor agonist, or a histamine $H_3$-receptor antagonist in the amount ranging from about 0.02 to about 30, from about 0.05 to about 20, from about 0.1 to about 15, or from about 0.2 to about 10% by weight. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.02 to about 30% by weight. In certain embodiments, a pharmaceutical composition provided herein comprises a histamine $H_1$-receptor agonist, a histamine $H_2$-receptor agonist, or a histamine $H_3$-receptor antagonist in the amount ranging from about 0.05 to about 20% by weight. In certain embodiments, a pharmaceutical composition provided herein comprises a histamine $H_1$-receptor agonist, a histamine $H_2$-receptor agonist, or a histamine $H_3$-receptor antagonist in the amount ranging from 0.1 to about 15% by weight. In certain embodiments, a pharmaceutical composition provided herein comprises a histamine $H_1$-receptor agonist, a histamine $H_2$-receptor agonist, or a histamine $H_3$-receptor antagonist in the amount ranging from 0.2 to about 10% by weight. In certain embodiments, a pharmaceutical composition provided herein comprises a histamine $H_1$-receptor agonist, a histamine $H_2$-receptor agonist, or a histamine $H_3$-receptor antagonist in the amount of about 0.2, about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10% by weight.

In certain embodiments, a pharmaceutical composition provided herein comprises a $\beta_2$-adrenoreceptor agonist in the amount ranging from about 0.005 to about 10, from about 0.01 to about 8, from about 0.02 to about 6, from about 0.05 to about 5% by weight. In certain embodiments, a pharmaceutical composition provided herein comprises a $\beta_2$-adrenoreceptor agonist in the amount ranging from about 0.005 to about 10% by weight. In certain embodiments, a pharmaceutical composition provided herein comprises a $\beta_2$-adrenoreceptor agonist in the amount ranging from about 0.01 to about 8% by weight. In certain embodiments, a pharmaceutical composition provided herein comprises a $\beta_2$-adrenoreceptor agonist in the amount ranging from about 0.02 to about 6% by weight. In certain embodiments, a pharmaceutical composition provided herein comprises a $\beta_2$-adrenoreceptor agonist in the amount ranging from about 0.05 to about 5% by weight. In certain embodiments, a pharmaceutical composition provided herein comprises a 02-adrenoreceptor agonist in the amount of about 0.05, about 0.1, about 1, about 1.5, about 2.0, about 2.5, about 3.0, about 3.5, about 4.0, about 4.5, or about 5% by weight.

Phosphodiesterase Inhibitors or Adenosine Receptor Antagonists

In some embodiments, a pharmaceutical composition provided herein comprises an API that is a phosphodiesterase (PDE) inhibitor and/or an adenosine receptor antagonist. PDE inhibitors and adenosine receptor antagonists are primarily used in the treatment of chronic obstructive pulmonary disease (COPD) and asthma. One secondary therapeutical effect of this API is that it increases heart rate and cardiac output. The molecular mechanism of action of this API as a phosphodiesterase inhibitor and/or adenosine receptor is (i) inhibiting a phosphodiesterase competitively and nonselectively, which increase intracellular cyclic adenosine monophosphate (cAMP), activates protein kinase A (PKA), inhibits tumor necrosis factor (TNF)-alpha, inhibits leukotriene synthesis, and reduces inflammation and innate immunity; and (ii) antagonizing nonselectively an adenosine receptor, antagonizing $A_1$, $A_2$, and $A_3$ receptors almost equally, which explains many of its cardiac effects. By inhibiting a phosphodiesterase, the hydrolysis of cyclic cAMP is reduced, thus promoting endogenous epinephrine and controlling norepinephrine release. An adenosine receptor antagonist can antagonize adenosine and prevent the excessive release of adenosine, consequently increasing cAMP in myocardial cells resulting in an increase in heart rate (HR) and cardiac output. When taken in a combination of two or more APIs provided herein, the undesired side effects of this API, which includes an increase in myocardial contractility, myocardial metabolism, and oxygen consumption, can be minimized or even eliminated by the counteracting reduction of oxygen consumption and myocardial metabolism induced by another API such as a calcium channel blocker disclosed herein. Meanwhile, the desired effects can be enhanced that include, but are not limited to, increased heart rate and cardiac output using a combination of two or more APIs provided herein.

The present disclosure discloses a surprising finding that, when used as part of a combination of two or more APIs provided herein, a PDE inhibitor and/or adenosine receptor antagonist is useful in the treatment of bradycardia while avoiding or minimizing certain associated undesired side effects.

In certain embodiments, the phosphodiesterase (PDE) inhibitor is a xanthine compound or an isotopic variant thereof, or a pharmaceutically acceptable salt, hydrate, or solvate thereof. In certain embodiments, the PDE inhibitor is a methylxanthine compound or an isotopic variant thereof; or a pharmaceutically acceptable salt, hydrate, or solvate thereof. In certain embodiments, the PDE inhibitor is caffeine, doxophylline, dyphylline, oxtriphylline, paraxanthine, pentoxifylline, theobromine, theophylline, or an isotopic variant thereof; or a pharmaceutically acceptable salt, hydrate, or solvate thereof. In certain embodiments, the PDE inhibitor is aminophylline, caffeine, doxophylline, dyphylline, oxtriphylline, paraxanthine, pentoxifylline, theobromine, or theophylline. In certain embodiments, the PDE inhibitor is aminophylline, caffeine, doxophylline, dyphylline, oxtriphylline, pentoxifylline, or theophylline. In certain embodiments, the PDE inhibitor is aminophylline. In certain embodiments, the PDE inhibitor is caffeine. In certain embodiments, the PDE inhibitor is doxophylline. In certain embodiments, the PDE inhibitor is dyphylline. In certain embodiments, the PDE inhibitor is oxtriphylline. In certain embodiments, the PDE inhibitor is pentoxifylline. In certain embodiments, the PDE inhibitor is theophylline.

In certain embodiments, the PDE inhibitor is a nonselective PDE inhibitor. In certain embodiments, the PDE inhibitor is a competitive nonselective PDE inhibitor. In certain embodiments, the nonselective PDE inhibitor is caffeine, paraxanthine, pentoxifylline, theobromine, theophylline, or an isotopic variant thereof; or a pharmaceutically acceptable salt, hydrate, or solvate thereof.

In certain embodiments, the PDE inhibitor is a PDE1 inhibitor. In certain embodiments, the PDE inhibitor is a PDE1 selective inhibitor. In certain embodiments, the PDE1 inhibitor is vinpocetine or an isotopic variant thereof; or a pharmaceutically acceptable salt, hydrate, or solvate thereof.

In certain embodiments, the PDE inhibitor is a PDE2 inhibitor. In certain embodiments, the PDE inhibitor is a PDE2 selective inhibitor. In certain embodiments, the PDE2 inhibitor is EHNA (erythro-9-(2-hydroxy-3-nonyl)adenine), BAY 60-7550 (2-[(3,4-dimethoxyphenyl)methyl]-7-[(1R)-1-hydroxyethyl]-4-phenylbutyl]-5-methyl-imidazo[5,1-f][1,2,4]triazin-4(1H)-one), oxindole, PDP (9-(6-phenyl-2-oxo-hex-3-yl)-2-(3,4-dimethoxybenzyl)-purin-6-one), or an isotopic variant thereof; or a pharmaceutically acceptable salt, hydrate, or solvate thereof.

In certain embodiments, the PDE inhibitor is a PDE3 inhibitor. In certain embodiments, the PDE inhibitor is a PDE3 selective inhibitor. In certain embodiments, the PDE3 inhibitor is anagrelide, cilostazol, enoximone, inamrinone, milrinone, pimobendan, or an isotopic variant thereof, or a pharmaceutically acceptable salt, hydrate, or solvate thereof.

In certain embodiments, the PDE inhibitor is a PDE4 inhibitor. In certain embodiments, the PDE inhibitor is a PDE4 selective inhibitor. In certain embodiments, the PDE4 inhibitor is apremilast, drotaverine, ibudilast, luteolin, mesembrine, piclamilast, roflumilast, rolipram, or an isotopic variant thereof; or a pharmaceutically acceptable salt, hydrate, or solvate thereof.

In certain embodiments, the PDE inhibitor is a PDE5 inhibitor. In certain embodiments, the PDE inhibitor is a PDE5 selective inhibitor. In certain embodiments, the PDE5 inhibitor is avanafil, dipyridamole, icariin, sildenafil, tadalafil, udenafil, vardenafil, or an isotopic variant thereof, or a pharmaceutically acceptable salt, hydrate, or solvate thereof. In certain embodiments, the PDE5 inhibitor is 4-methylpiperazine, pyrazolo pyrimidin-7-1, or an isotopic variant thereof, or a pharmaceutically acceptable salt, hydrate, or solvate thereof.

In certain embodiments, the PDE inhibitor is a PDE7 inhibitor. In certain embodiments, the PDE inhibitor is a PDE7 selective inhibitor. In certain embodiments, the PDE7 inhibitor is quinazoline or an isotopic variant thereof, or a pharmaceutically acceptable salt, hydrate, or solvate thereof.

In certain embodiments, the PDE inhibitor is a PDE10 inhibitor. In certain embodiments, the PDE inhibitor is a PDE10 selective inhibitor. In certain embodiments, the PDE10 inhibitor is papaverine or an isotopic variant thereof, or a pharmaceutically acceptable salt, hydrate, or solvate thereof.

In certain embodiments, the PDE inhibitor is adibendan, amipizone, anagrelide, apremilast, arofylline, atizoram, avanafil, befuraline, bemarinone, bemoradan, benafentrine, bucladesine, buflomedil, buquineran, CC-1088, carbazeran, catramilast, cilomilast, cilostazol, crisaborole (AN2728), dipyridamole, drotaverin, enoximone, etamiphyllin, ibudilast, inamrinone, luteolin, mesembrenone, metescufylline, midaxifylline, milrinone, motapizone, papaverine, parogrelil, pelrinone, pentifylline, pentoxifylline, perbufylline, piclamilast, pimefylline, pimobendan, piroximone, prinoxodan, proxyphylline, pumafentrine, roflumilast, rolipram, sildenafil, tadalafil, theophylline, udenafil, vardenafil, vinpocetine, or an isotopic variant thereof; or a pharmaceutically acceptable salt, hydrate, or solvate thereof.

In certain embodiments, the PDE inhibitor is AN2728, adibendan, aminophylline, aminophylline dihydrate, amipizone, arofylline, atizoram, befuraline, bemarinone hydrochloride, bemoradan, benafentrine, bucladesine, buflomedil, buquineran, CC-1088, carbazeran, catramilast, cilomilast, cilostamide, cilostazol, cipamfylline, daxalipram, denbufylline, dimabefylline, diniprofylline, dipyridamole, doxofylline, drotaverine, dyphylline, enoximone, etamiphyllin, etofylline, filaminast, flufylline, fluprofylline, furafylline, imazodan, imazodan hydrochloride, inamrinone, inamrinone lactate, isbufylline, lirimilast, lisofylline, lomifylline, medorinone, metescufylline, midaxifylline, milrinone, milrinone lactate, motapizone, nanterinone, nestifylline, nitraquazone, oglemilast, oglemilast sodium, olprinone, oxagrelate, oxtriphylline, papaverine, papaverine hydrochloride, papaverine sulfate, parogrelil, pelrinone hydrochloride, pentifylline, pentoxifylline, perbufylline, piclamilast, pimefylline, pimobendan, piroximone, prinoxodan, proxyphylline, pumafentrine, quazinone, quazodine, revamilast, revizinone, roflumilast, rolipram, ronomilast, saterinone, senazodan, siguazodan, tetomilast, theophylline, tofimilast, trapidil, vesnarinone, or zardaverine.

In certain embodiments, the PDE inhibitor is aminotadalafil, avanafil, beminafil, dasantafil, gisadenafil, gisadenafil besylate, mirodenafil, sildenafil, sildenafil citrate, tadalafil, udenafil, vardenafil, vardenafil dihydrochloride, vardenafil hydrochloride trihydrate, or zaprinast.

In certain embodiments, the adenosine receptor antagonist is a xanthine compound or an isotopic variant thereof; or a pharmaceutically acceptable salt, hydrate, or solvate thereof. In certain embodiments, the adenosine receptor antagonist is a methylxanthine compound or an isotopic variant thereof; or a pharmaceutically acceptable salt, hydrate, or solvate thereof. In certain embodiments, the adenosine receptor antagonist is caffeine, paraxanthine, pentoxifylline, theobromine, theophylline, or an isotopic variant thereof; or a pharmaceutically acceptable salt, hydrate, or solvate thereof. In certain embodiments, the adenosine receptor antagonist is aminophylline, caffeine, doxophylline, dyphylline, oxtriphylline, paraxanthine, pentoxifylline, theobromine, or theophylline. In certain embodiments, the adenosine receptor antagonist is aminophylline. In certain embodiments, the adenosine receptor antagonist is theophylline.

In certain embodiments, the adenosine receptor antagonist is a nonselective adenosine receptor antagonist. In certain embodiments, the adenosine receptor antagonist is an $A_1$ antagonist. In certain embodiments, the adenosine receptor antagonist is an $A_2$ antagonist. In certain embodiments, the adenosine receptor antagonist is an $A_3$ antagonist. In certain embodiments, the adenosine receptor antagonist is an antagonist of $A_1$, $A_2$, and $A_3$ receptors.

In one embodiment, provided herein is a pharmaceutical composition comprising (i) a xanthine compound or an isotopic variant thereof; or a pharmaceutically acceptable salt, hydrate, or solvate thereof; and (ii) one or more compounds, wherein each compound is independently a calcium channel blocker, a histamine $H_1$-receptor agonist, a histamine $H_2$-receptor agonist, a histamine $H_3$-receptor antagonist, or a $\beta_2$-adrenoreceptor agonist.

In another embodiment, provided herein is a pharmaceutical composition comprising (i) a xanthine compound or an isotopic variant thereof; or a pharmaceutically acceptable salt, hydrate, or solvate thereof; and (ii) a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a xanthine compound or an isotopic variant thereof; or a pharmaceutically acceptable salt, hydrate, or solvate thereof; and (ii) a calcium channel blocker. In another embodiment, the pharmaceutical composition comprises (i) a xanthine compound or an isotopic variant thereof; or a pharmaceutically acceptable salt, hydrate, or solvate thereof; and (ii) a histamine $H_1$-receptor agonist, a histamine $H_2$-receptor agonist, or a histamine $H_3$-receptor antagonist. In yet another embodiment, the pharmaceutical composition comprises (i) a xanthine compound or an isotopic variant thereof; or a pharmaceutically acceptable salt, hydrate, or solvate thereof; and (ii) a $\beta_2$-adrenoreceptor agonist.

In yet another embodiment, provided herein is a pharmaceutical composition comprising (i) a xanthine compound or an isotopic variant thereof; or a pharmaceutically acceptable salt, hydrate, or solvate thereof; and (ii) two compounds, wherein each compound is independently a calcium channel blocker, a histamine $H_1$-receptor agonist, a histamine Hz-receptor agonist, a histamine $H_3$-receptor antagonist, or a $\beta_2$-adrenoreceptor agonist.

In one embodiment, the pharmaceutical composition comprises (i) a xanthine compound or an isotopic variant thereof; or a pharmaceutically acceptable salt, hydrate, or solvate thereof, (ii) a calcium channel blocker; and (iii) a histamine $H_1$-receptor agonist, a histamine $H_2$-receptor agonist, or a histamine $H_3$-receptor antagonist. In another embodiment, the pharmaceutical composition comprises (i) a xanthine compound or an isotopic variant thereof, or a pharmaceutically acceptable salt, hydrate, or solvate thereof; (ii) a calcium channel blocker; and (iii) a $\beta_2$-adrenoreceptor agonist. In yet another embodiment, the pharmaceutical composition comprises (i) a xanthine compound or an isotopic variant thereof, or a pharmaceutically acceptable salt, hydrate, or solvate thereof; (ii) a histamine $H_1$-receptor agonist, a histamine $H_2$-receptor agonist, or a histamine $H_3$-receptor antagonist; and (iii) a $\beta_2$-adrenoreceptor agonist.

In still another embodiment, provided herein is a pharmaceutical composition comprising (i) a xanthine compound or an isotopic variant thereof; or a pharmaceutically acceptable salt, hydrate, or solvate thereof; and (ii) three compounds, wherein each compound is independently a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a xanthine compound or an isotopic variant thereof; or a pharmaceutically acceptable salt, hydrate, or solvate thereof; (ii) a calcium channel blocker; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the xanthine compound is a methylxanthine. In certain embodiments, the xanthine compound is caffeine, doxophylline, dyphylline, oxtriphylline, paraxanthine, pentoxifylline, theobromine, theophylline, or an isotopic variant thereof; or a pharmaceutically acceptable salt, hydrate, or solvate thereof. In certain embodiments, the xanthine compound is aminophylline, caffeine, doxophylline, dyphylline, oxtriphylline, paraxanthine, pentoxifylline, theobromine, or theophylline. In certain embodiments, the xanthine compound is aminophylline. In certain embodiments, the xanthine compound is theophylline.

In certain embodiments, the xanthine compound or an isotopic variant thereof, or a pharmaceutically acceptable salt, hydrate, or solvate thereof is a solid. In certain embodiments, the xanthine compound or an isotopic variant thereof, or a pharmaceutically acceptable salt, hydrate, or solvate thereof is a crystalline solid. In certain embodiments, the xanthine compound or an isotopic variant thereof, or a pharmaceutically acceptable salt, hydrate, or solvate thereof is an amorphous solid.

In certain embodiments, the weight ratio of the xanthine compound to the calcium channel blocker in a pharmaceutical composition provided herein is ranging from about 1 to about 180, from about 2 to about 100, from about 2 to about 50, or from about 2 to about 20. In certain embodiments, the weight ratio of the xanthine compound to the calcium channel blocker in a pharmaceutical composition provided herein is ranging from about 1 to about 180. In certain embodiments, the weight ratio of the xanthine compound to the calcium channel blocker in a pharmaceutical composition provided herein is ranging from about 2 to about 100. In certain embodiments, the weight ratio of the xanthine compound to the calcium channel blocker in a pharmaceutical composition provided herein is ranging from about 2 to about 50. In certain embodiments, the weight ratio of the xanthine compound to the calcium channel blocker in a pharmaceutical composition provided herein is ranging from about 2 to about 20. In certain embodiments, the weight ratio of the xanthine compound to the calcium channel blocker in a pharmaceutical composition provided herein is about 2, about 4, about 6, about 8, about 10, about 12, about 14, about 16, about 18, or about 20.

In certain embodiments, the weight ratio of (i) the xanthine compound to (ii) the histamine $H_1$-receptor agonist, histamine $H_2$-receptor agonist, or histamine $H_3$-receptor antagonist in a pharmaceutical composition provided herein is ranging from about 2 to about 200, from about 4 to about 100, from about 5 to about 50, or from about 10 to about 30. In certain embodiments, the weight ratio of (i) the xanthine compound to (ii) the histamine $H_1$-receptor agonist, histamine $H_2$-receptor agonist, or histamine $H_3$-receptor antagonist in a pharmaceutical composition provided herein is about 10, about 12, about 14, about 16, about 17, about 18, about 19, about 20, about 21, about 22, about 23, about 24, about 25, about 26, about 27, about 28, about 29, or about 30.

In certain embodiments, the weight ratio of the xanthine compound to the $\beta_2$-adrenoreceptor agonist in a pharmaceutical composition provided herein is ranging from about 1 to about 1,000, from about 10 to about 500, from about 20 to about 400, or from about 40 to about 300. In certain embodiments, the weight ratio of the xanthine compound to the $\beta_2$-adrenoreceptor agonist in a pharmaceutical composition provided herein is about 40, about 60, about 80, about 100, about 120, about 140, about 160, about 180, about 200, about 220, about 240, about 260, about 280, or about 300.

In certain embodiments, a pharmaceutical composition provided herein comprises a xanthine compound in the amount ranging from about 1 to about 1,200, from about 1 to about 1,000, from about 1 to about 800, from about 1 to about 600, from about 2 to about 300, or from about 20 to about 200 mg. In certain embodiments, a pharmaceutical composition provided herein comprises a xanthine compound in the amount ranging from about 1 to about 1,200 mg. In certain embodiments, a pharmaceutical composition provided herein comprises a xanthine compound in the amount ranging from about 1 to about 1,000 mg. In certain embodiments, a pharmaceutical composition provided herein comprises a xanthine compound in the amount ranging from about 1 to about 800 mg. In certain embodiments, a pharmaceutical composition provided herein comprises a xanthine compound in the amount ranging from about 1 to about 600 mg. In certain embodiments, a pharmaceutical composition provided herein comprises a xanthine compound in the amount ranging from about 2 to about 300 mg. In certain embodiments, a pharmaceutical composition provided herein comprises a xanthine compound in the amount ranging from about 10 to about 200 mg. In certain embodiments, a pharmaceutical composition provided herein comprises a xanthine compound in the amount of about 10, about 20, about 30, about 40, about 50, about 60, about 70, about 80, about 90, about 100, about 110, about 120, about 130, about 140, about 150, about 160, about 170, about 180, about 190, or about 200 mg.

In certain embodiments, a pharmaceutical composition provided herein comprises a xanthine compound in the amount ranging from about 1 to about 90, from about 2 to about 80, from 5 to about 60, or from about 5 to about 35% by weight. In certain embodiments, a pharmaceutical composition provided herein comprises a xanthine compound in the amount ranging from about 1 to about 90% by weight. In certain embodiments, a pharmaceutical composition provided herein comprises a xanthine compound in the amount ranging from about 2 to about 80% by weight. In certain embodiments, a pharmaceutical composition provided herein comprises a xanthine compound in the amount ranging from about 5 to about 60% by weight. In certain embodiments, a pharmaceutical composition provided herein comprises a xanthine compound in the amount ranging from about 5 to about 35% by weight. In certain embodiments, a pharmaceutical composition provided herein comprises a xanthine compound in the amount of about 5, about 10, about 15, about 20, about 25, about 30, or about 35% by weight.

Calcium Channel Blockers

In some embodiments, a pharmaceutical composition provided herein comprises an API that is a calcium channel blocker. Calcium channel blockers are commonly used in the treatment of high blood pressure. By blocking calcium channels, these APIs relax coronary artery systems and prevent coronary artery spasms (thus dilating the main coronary arteries and coronary arterioles, both in normal and ischemic region), and further reduce oxygen utilization, thereby reducing arterial pressure by dilating peripheral arterioles and reducing the total peripheral resistance against which the heart works. The undesired side effects including, but not limited to, inhibition of myocardial contractility and reduction in myocardial metabolism, are minimized or eliminated by counteracting effects induced by another API in the combination such as an API that is a PDE inhibitor or an adenosine receptor antagonist. Meanwhile, desired effects can be enhanced that include, but are not limited to, increased heart rate and cardiac output using a combination of two or more APIs provided herein.

The present disclosure discloses a surprisingly finding that, when used as part of a combination provided herein, calcium channel blockers are useful in the treatment of bradycardia while avoiding or minimizing certain associated undesired side effects.

In certain embodiments, the calcium channel blocker is amlodipine, aranidipine, azelnidipine, barnidipine, benidipine, cilnidipine, clevidipine, diltiazem, efonidipine, felodipine, fendiline, gabapentin, gallopamil, isradipine, lacidipine, lercanidipine, manidipine, nicardipine, nifedipine, nilvadipine, nimodipine, nisoldipine, nitrendipine, pranidipine, pregabalin, verapamil, ziconotide, or an isotopic variant thereof; or a pharmaceutically acceptable salt, hydrate, or solvate thereof. In certain embodiments, the calcium channel blocker is bepridil, flunarizine, fluspirilene, mibefradil, or an isotopic variant thereof; or a pharmaceutically acceptable salt, hydrate, or solvate thereof.

In certain embodiments, the calcium channel blocker is a dihydropyridine or an isotopic variant thereof, or a pharmaceutically acceptable salt, hydrate, or solvate thereof. In certain embodiments, the calcium channel blocker is amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine, pranidipine, or an isotopic variant thereof; or a pharmaceutically acceptable salt, hydrate, or solvate thereof.

In certain embodiments, the calcium channel blocker is amlodipine or an isotopic variant thereof, or a pharmaceutically acceptable salt, hydrate, or solvate thereof. In certain embodiments, the calcium channel blocker is aranidipine or an isotopic variant thereof, or a pharmaceutically acceptable salt, hydrate, or solvate thereof. In certain embodiments, the calcium channel blocker is azelnidipine or an isotopic variant thereof; or a pharmaceutically acceptable salt, hydrate, or solvate thereof. In certain embodiments, the calcium channel blocker is barnidipine or an isotopic variant thereof; or a pharmaceutically acceptable salt, hydrate, or solvate thereof. In certain embodiments, the calcium channel blocker is benidipine or an isotopic variant thereof; or a pharmaceutically acceptable salt, hydrate, or solvate thereof. In certain embodiments, the calcium channel blocker is bepridil or an isotopic variant thereof, or a pharmaceutically acceptable salt, hydrate, or solvate thereof. In certain embodiments, the calcium channel blocker is cilnidipine or an isotopic variant thereof; or a pharmaceutically acceptable salt, hydrate, or solvate thereof. In certain embodiments, the calcium channel blocker is clevidipine or an isotopic variant thereof; or a pharmaceutically acceptable salt, hydrate, or solvate thereof. In certain embodiments, the calcium channel blocker is diltiazem or an isotopic variant thereof; or a pharmaceutically acceptable salt, hydrate, or solvate thereof. In certain embodiments, the calcium channel blocker is efonidipine or an isotopic variant thereof; or a pharmaceutically acceptable salt, hydrate, or solvate thereof. In certain embodiments, the calcium channel blocker is felodipine or an isotopic variant thereof; or a pharmaceutically acceptable salt, hydrate, or solvate thereof. In certain embodiments, the calcium channel blocker is fendiline or an isotopic variant thereof; or a pharmaceutically acceptable salt, hydrate, or solvate thereof. In certain embodiments, the calcium channel blocker is flunarizine or an isotopic variant thereof; or a pharmaceutically acceptable salt, hydrate, or solvate thereof. In certain embodiments, the calcium channel blocker is fluspirilene or an isotopic variant thereof; or a pharmaceutically acceptable salt, hydrate, or solvate thereof. In certain embodiments, the calcium channel blocker is gallopamil or an isotopic variant thereof; or a pharmaceutically acceptable salt, hydrate, or solvate thereof. In certain embodiments, the calcium channel blocker is isradipine or an isotopic variant thereof; or a pharmaceutically acceptable salt, hydrate, or solvate thereof. In certain embodiments, the calcium channel blocker is lacidipine or an isotopic variant thereof; or a pharmaceutically acceptable salt, hydrate, or solvate thereof. In certain embodiments, the calcium channel blocker is lercanidipine or an isotopic variant thereof, or a pharmaceutically acceptable salt, hydrate, or solvate thereof. In certain embodiments, the calcium channel blocker is manidipine or an isotopic variant thereof, or a pharmaceutically acceptable salt, hydrate, or solvate thereof. In certain embodiments, the calcium channel blocker is mibefradil or an isotopic variant thereof, or a pharmaceutically acceptable salt, hydrate, or solvate thereof. In certain embodiments, the calcium channel blocker is nicardipine or an isotopic variant thereof, or a pharmaceutically acceptable salt, hydrate, or solvate thereof. In certain embodiments, the calcium channel blocker is nifedipine or an isotopic variant thereof, or a pharmaceutically acceptable salt, hydrate, or solvate thereof. In certain embodiments, the calcium channel blocker is nilvadipine or an isotopic variant thereof, or a pharmaceutically acceptable salt, hydrate, or solvate thereof. In certain embodiments, the calcium channel blocker is nimodipine or an isotopic variant thereof, or a pharmaceutically acceptable salt, hydrate, or solvate thereof. In certain embodiments, the calcium channel blocker is nisoldipine or an isotopic variant thereof, or a pharmaceutically acceptable salt, hydrate, or solvate thereof. In certain embodiments, the calcium channel blocker is nitrendipine or an isotopic variant thereof, or a pharmaceutically acceptable salt, hydrate, or solvate thereof. In certain embodiments, the calcium channel blocker is pranidipine or an isotopic variant thereof; or a pharmaceutically acceptable salt, hydrate, or solvate thereof. In certain embodiments, the calcium channel blocker is verapamil or an isotopic variant thereof, or a pharmaceutically acceptable salt, hydrate, or solvate thereof. In certain embodiments, the calcium channel blocker is ziconotide or an isotopic variant thereof, or a pharmaceutically acceptable salt, hydrate, or solvate thereof.

In one embodiment, provided herein is a pharmaceutical composition comprising (i) a dihydropyridine or an isotopic variant thereof, or a pharmaceutically acceptable salt, hydrate, or solvate thereof, and (ii) one or more compounds, wherein each compound is independently a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In another embodiment, provided herein is a pharmaceutical composition comprising (i) a dihydropyridine or an isotopic variant thereof, or a pharmaceutically acceptable salt, hydrate, or solvate thereof; and (ii) a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a dihydropyridine or an isotopic variant thereof; or a pharmaceutically acceptable salt, hydrate, or solvate thereof; and (ii) a PDE inhibitor or an adenosine receptor antagonist. In another embodiment, the pharmaceutical composition comprises (i) a dihydropyridine or an isotopic variant thereof; or a pharmaceutically acceptable salt, hydrate, or solvate thereof; and (ii) a histamine $H_1$-receptor agonist, a histamine $H_2$-receptor agonist, or a histamine $H_3$-receptor antagonist. In yet another embodiment, the pharmaceutical composition comprises (i) a dihydropyridine or an isotopic variant thereof; or a pharmaceutically acceptable salt, hydrate, or solvate thereof; and (ii) a $\beta_2$-adrenoreceptor agonist.

In yet another embodiment, provided herein is a pharmaceutical composition comprising (i) a dihydropyridine or an isotopic variant thereof; or a pharmaceutically acceptable salt, hydrate, or solvate thereof; and (ii) two compounds, wherein each compound is independently a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a dihydropyridine or an isotopic variant thereof; or a pharmaceutically acceptable salt, hydrate, or solvate thereof; (ii) a PDE inhibitor or an adenosine receptor antagonist; and (iii) a histamine $H_1$-receptor agonist, a histamine $H_2$-receptor agonist, or a histamine $H_3$-receptor antagonist. In another embodiment, the pharmaceutical composition comprises (i) a dihydropyridine or an isotopic variant thereof; or a pharmaceutically acceptable salt, hydrate, or solvate thereof; (ii) a PDE inhibitor or an adenosine receptor antagonist; and (iii) a $\beta_2$-adrenoreceptor agonist. In yet another embodiment, the pharmaceutical composition comprises (i) a dihydropyridine or an isotopic variant thereof; or a pharmaceutically acceptable salt, hydrate, or solvate thereof; (ii) a histamine $H_1$-receptor agonist, a histamine $H_2$-receptor agonist, or a histamine $H_3$-receptor antagonist; and (iii) a $\beta_2$-adrenoreceptor agonist.

In yet another embodiment, provided herein is a pharmaceutical composition comprising (i) a dihydropyridine or an isotopic variant thereof; or a pharmaceutically acceptable salt, hydrate, or solvate thereof; and (ii) three compounds, wherein each compound is independently a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a dihydropyridine or an isotopic variant thereof, or a pharmaceutically acceptable salt, hydrate, or solvate thereof; (ii) a PDE inhibitor or an adenosine receptor antagonist; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the dihydropyridine is amlodipine, aranidipine, azelnidipine, barnidipine, benidipine, cilnidipine, clevidipine, cronidipine, darodipine, dexniguldipine, efonidipine, elgodipine, elnadipine, felodipine, flordipine, fumidipine, iganidine, isradipine, lacidipine, lemildipine, lercanidipine, levamlodipine, levniguldipine, manidipine, nicardipine, nifedipine, niguldipine, niludipine, nivadipine, nimodipine, nisoldipine, nitrendipine, olradipine, oxodipine, palonidipine, pranidipine, ryodipine, sagandipine, sornidipine, teludipine, tiamdipine, trombodipine, vatanidipine, or an isotopic variant thereof, or a pharmaceutically acceptable salt, hydrate, or solvate thereof.

In certain embodiments, the dihydropyridine is amlodipine, aranidipine, azelnidipine, barnidipine, benidipine, cilnidipine, clevidipine, efonidipine, felodipine, isradipine, lacidipine, lercanidipine, levamlodipine, manidipine, nicardipine, nifedipine, nivadipine, nimodipine, nisoldipine, nitrendipine, pranidipine, or an isotopic variant thereof, or a pharmaceutically acceptable salt, hydrate, or solvate thereof.

In certain embodiments, the dihydropyridine is amlodipine or an isotopic variant thereof, or a pharmaceutically acceptable salt, hydrate, or solvate thereof. In certain embodiments, the dihydropyridine is aranidipine or an isotopic variant thereof, or a pharmaceutically acceptable salt, hydrate, or solvate thereof. In certain embodiments, the dihydropyridine is azelnidipine or an isotopic variant thereof, or a pharmaceutically acceptable salt, hydrate, or solvate thereof. In certain embodiments, the dihydropyridine is barnidipine or an isotopic variant thereof, or a pharmaceutically acceptable salt, hydrate, or solvate thereof. In certain embodiments, the dihydropyridine is benidipine or an isotopic variant thereof, or a pharmaceutically acceptable salt, hydrate, or solvate thereof. In certain embodiments, the dihydropyridine is cilnidipine or an isotopic variant thereof, or a pharmaceutically acceptable salt, hydrate, or solvate thereof. In certain embodiments, the dihydropyridine is clevidipine or an isotopic variant thereof, or a pharmaceutically acceptable salt, hydrate, or solvate thereof. In certain embodiments, the dihydropyridine is efonidipine or an isotopic variant thereof; or a pharmaceutically acceptable salt, hydrate, or solvate thereof. In certain embodiments, the dihydropyridine is felodipine or an isotopic variant thereof, or a pharmaceutically acceptable salt, hydrate, or solvate thereof. In certain embodiments, the dihydropyridine is isradipine or an isotopic variant thereof, or a pharmaceutically acceptable salt, hydrate, or solvate thereof. In certain embodiments, the dihydropyridine is lacidipine or an isotopic variant thereof, or a pharmaceutically acceptable salt, hydrate, or solvate thereof. In certain embodiments, the dihydropyridine is lercanidipine or an isotopic variant thereof, or a pharmaceutically acceptable salt, hydrate, or solvate thereof. In certain embodiments, the dihydropyridine is levamlodipine or an isotopic variant thereof, or a pharmaceutically acceptable salt, hydrate, or solvate thereof. In certain embodiments, the dihydropyridine is manidipine or an isotopic variant thereof, or a pharmaceutically acceptable salt, hydrate, or solvate thereof. In certain embodiments, the dihydropyridine is nicardipine or an isotopic variant thereof, or a pharmaceutically acceptable salt, hydrate, or solvate thereof. In certain embodiments, the dihydropyridine is nifedipine or an isotopic variant thereof, or a pharmaceutically acceptable salt, hydrate, or solvate thereof. In certain embodiments, the dihydropyridine is nivadipine or an isotopic variant thereof, or a pharmaceutically acceptable salt, hydrate, or solvate thereof. In certain embodiments, the dihydropyridine is nimodipine or an isotopic variant thereof, or a pharmaceutically acceptable salt, hydrate, or solvate thereof. In certain embodiments, the dihydropyridine is nisoldipine or an isotopic variant thereof, or a pharmaceutically acceptable salt, hydrate, or solvate thereof. In certain embodiments, the dihydropyridine is nitrendipine or an isotopic variant thereof, or a pharmaceutically acceptable salt, hydrate, or solvate thereof. In certain embodiments, the dihydropyridine is pranidipine or an isotopic variant thereof, or a pharmaceutically acceptable salt, hydrate, or solvate thereof.

In certain embodiments, the dihydropyridine or an isotopic variant thereof, or a pharmaceutically acceptable salt, hydrate, or solvate thereof is a solid. In certain embodiments, the dihydropyridine or an isotopic variant thereof, or a pharmaceutically acceptable salt, hydrate, or solvate thereof is a crystalline solid. In certain embodiments, the dihydropyridine or an isotopic variant thereof, or a pharmaceutically acceptable salt, hydrate, or solvate thereof is an amorphous solid.

In certain embodiments, the weight ratio of (i) the phosphodiesterase inhibitor or adenosine receptor antagonist to (ii) the dihydropyridine in a pharmaceutical composition provided herein is ranging from about 1 to about 180, from about 2 to about 100, or from about 2 to about 20. In certain embodiments, the weight ratio of (i) the phosphodiesterase inhibitor or adenosine receptor antagonist to (ii) the dihydropyridine in a pharmaceutical composition provided herein is about 2, about 3, about 4, about 5, about 6, about 7, about 8, about 9, about 10, about 11, about 12, about 13, about 14, about 15, about 16, about 17, about 18, about 19, or about 20.

In certain embodiments, the weight ratio of (i) the dihydropyridine to (ii) the histamine $H_1$-receptor agonist, histamine $H_2$-receptor agonist, or histamine $H_3$-receptor antagonist in a pharmaceutical composition provided herein is ranging from about 0.1 to about 50, from about 1 to about 40, from about 1 to about 20, or from about 1 to about 10. In certain embodiments, the weight ratio of (i) the dihydropyridine to (ii) the histamine $H_1$-receptor agonist, histamine $H_2$-receptor agonist, or histamine $H_3$-receptor antagonist in a pharmaceutical composition provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10. In certain embodiments, the weight ratio of (i) the dihydropyridine to (ii) the histamine $H_1$-receptor agonist, histamine $H_2$-receptor agonist, or histamine $H_3$-receptor antagonist in a pharmaceutical composition provided herein is about 2, about 2.2, about 2.4, about 2.6, about 2.8, about 3, about 3.2, about 3.4, about 3.6, about 3.8, or about 4.

In certain embodiments, the weight ratio of the dihydropyridine to the $\beta_2$-adrenoreceptor agonist in a pharmaceutical composition provided herein is ranging from about 1 to about 100, from about 5 to about 50, or from about 5 to about 30. In certain embodiments, the weight ratio of the dihydropyridine to the $\beta_2$-adrenoreceptor agonist in a pharmaceutical composition provided herein is about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

In certain embodiments, a pharmaceutical composition provided herein comprises a dihydropyridine in the amount ranging from about 0.1 to about 200, from about 0.1 to about 100, from about 0.2 to about 80, from about 1 to about 50, or from about 1 to about 30 mg. In certain embodiments, a pharmaceutical composition provided herein comprises a dihydropyridine in the amount ranging from about 0.1 to about 200 mg. In certain embodiments, a pharmaceutical composition provided herein comprises a dihydropyridine in the amount ranging from about 0.1 to about 100 mg. In certain embodiments, a pharmaceutical composition provided herein comprises a dihydropyridine in the amount ranging from about 0.2 to about 80 mg. In certain embodiments, a pharmaceutical composition provided herein comprises a dihydropyridine in the amount ranging from about 1 to about 50 mg. In certain embodiments, a pharmaceutical composition provided herein comprises a dihydropyridine in the amount ranging from about 1 to about 30 mg. In certain embodiments, a pharmaceutical composition provided herein comprises a dihydropyridine in the amount of about 1, about 2, about 4, about 6, about 8, about 10, about 12, about 14, about 16, about 18, about 20, about 22, about 24, about 26, about 28, or about 30 mg.

In certain embodiments, a pharmaceutical composition provided herein comprises a dihydropyridine in the amount ranging from about 0.1 to about 30, from about 0.5 to about 20, or from about 1 to about 10% by weight. In certain embodiments, a pharmaceutical composition provided herein comprises a dihydropyridine in the amount ranging from about 0.1 to about 30% by weight. In certain embodiments, a pharmaceutical composition provided herein comprises a dihydropyridine in the amount ranging from about 0.5 to about 20% by weight. In certain embodiments, a pharmaceutical composition provided herein comprises a dihydropyridine in the amount ranging from about 1 to about 10% by weight. In certain embodiments, a pharmaceutical composition provided herein comprises a dihydropyridine in the amount of about 1, about 2, about 3, about 4, about 5, about 6, about 7, about 8, about 9, or about 10% by weight.

In one embodiment, provided herein is a pharmaceutical composition comprising (i) a xanthine compound or an isotopic variant thereof; or a pharmaceutically acceptable salt, hydrate, or solvate thereof; (ii) a dihydropyridine or an isotopic variant thereof, or a pharmaceutically acceptable salt, hydrate, or solvate thereof; and (iii) optionally two or more compounds, wherein each compound is independently a histamine $H_1$-receptor agonist, a histamine $H_2$-receptor agonist, a histamine $H_3$-receptor antagonist, or a $\beta_2$-adrenoreceptor agonist.

In another embodiment, provided herein is a pharmaceutical composition comprising (i) a xanthine compound or an isotopic variant thereof; or a pharmaceutically acceptable salt, hydrate, or solvate thereof, and (ii) a dihydropyridine or an isotopic variant thereof, or a pharmaceutically acceptable salt, hydrate, or solvate thereof.

In yet another embodiment, provided herein is a pharmaceutical composition comprising (i) a xanthine compound or an isotopic variant thereof, or a pharmaceutically acceptable salt, hydrate, or solvate thereof; (ii) a dihydropyridine or an isotopic variant thereof, or a pharmaceutically acceptable salt, hydrate, or solvate thereof; and (iii) a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a xanthine compound or an isotopic variant thereof, or a pharmaceutically acceptable salt, hydrate, or solvate thereof; (ii) a dihydropyridine or an isotopic variant thereof, or a pharmaceutically acceptable salt, hydrate, or solvate thereof; and (iii) a histamine $H_1$-receptor agonist, a histamine $H_2$-receptor agonist, or a histamine $H_3$-receptor antagonist. In another embodiment, the pharmaceutical composition comprises (i) a xanthine compound or an isotopic variant thereof; or a pharmaceutically acceptable salt, hydrate, or solvate thereof; (ii) a dihydropyridine or an isotopic variant thereof, or a pharmaceutically acceptable salt, hydrate, or solvate thereof; and (iii) a $\beta_2$-adrenoreceptor agonist.

In still another embodiment, provided herein is a pharmaceutical composition comprising (i) a xanthine compound or an isotopic variant thereof; or a pharmaceutically acceptable salt, hydrate, or solvate thereof, (ii) a dihydropyridine or an isotopic variant thereof; or a pharmaceutically acceptable salt, hydrate, or solvate thereof; and (iii) two compounds, wherein each compound is independently a histamine $H_1$-receptor agonist, a histamine $H_2$-receptor agonist, a histamine $H_3$-receptor antagonist, or a $\beta_2$-adrenoreceptor agonist.

In one embodiment, the pharmaceutical composition comprises (i) a xanthine compound or an isotopic variant thereof; or a pharmaceutically acceptable salt, hydrate, or solvate thereof; (ii) a dihydropyridine or an isotopic variant thereof, or a pharmaceutically acceptable salt, hydrate, or solvate thereof; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the weight ratio of the xanthine compound to the dihydropyridine in a pharmaceutical composition provided herein is ranging from about 1 to about 180, from about 2 to about 100, from about 2 to about 50, or from about 2 to about 20. In certain embodiments, the weight ratio of the xanthine compound to the dihydropyridine in a pharmaceutical composition provided herein is ranging from about 1 to about 180. In certain embodiments, the weight ratio of the xanthine compound to the dihydropyridine in a pharmaceutical composition provided herein is ranging from about 2 to about 100. In certain embodiments, the weight ratio of the xanthine compound to the dihydropyridine in a pharmaceutical composition provided herein is ranging from about 2 to about 50. In certain embodiments, the weight ratio of the xanthine compound to the dihydropyridine in a pharmaceutical composition provided herein is ranging from about 2 to about 20. In certain embodiments, the weight ratio of the xanthine compound to the dihydropyridine in a pharmaceutical composition provided herein is about 2, about 4, about 6, about 8, about 10, about 12, about 14, about 16, about 18, or about 20.

Histamine $H_1$-Receptor Agonists, Histamine $H_2$-Receptor Agonists, or Histamine $H_3$-Receptor Antagonists In some embodiments, a pharmaceutical composition provided herein comprises an API that is a histamine $H_1$-receptor agonist, a histamine $H_2$-receptor agonist, and/or a histamine $H_3$ receptor antagonist. Similar to PDE inhibitors, adenosine receptor antagonists, and calcium channel blockers, when used in a therapeutically effective amount, a variety of undesired side effects are associated with a histamine $H_1$-receptor agonist, $H_2$-receptor agonist, or histamine $H_3$ receptor antagonist for its currently approved indication(s). A histamine $H_1$-receptor agonist, a histamine $H_2$-receptor agonist, or a histamine $H_3$-receptor antagonist is known to be useful in the treatment of vertigo. Without wishing to be bound by theory, there are two potential modes of action for a histamine $H_1$-receptor agonist, histamine $H_2$-receptor agonist, or histamine $H_3$-receptor antagonist. First, some histamine $H_3$ receptor antagonists can have a stimulating effect on $H_1$ receptors, giving rise to local vasodilation and permeability. Second, antagonistic effects on H$_3$ receptors can cause an increasing the levels of histamine, acetylcholine, norepinephrine, serotonin, and γ-aminobutyric acid (GABA) released from nerve endings, causing vasodilatory effect, including reduced blood pressure. These undesired side effects can be minimized or eliminated by counteracting effects induced by another API such as a β$_2$-adrenoreceptor agonist (e.g., albuterol or levalbuterol) provided herein. Meanwhile, desired effects can be enhanced that include, but are not limited to, increased dilation of peripheral small arteries and venules, resulting in an increase in HR and cardiac output using a combination of two or more APIs provided herein.

The present disclosure discloses a surprising finding that, when used as part of a combination of two or more APIs provided herein, the histamine H$_1$-receptor agonist, histamine H$_2$-receptor agonist, or histamine H$_3$-receptor antagonist is useful in the treatment of bradycardia while avoiding certain associated undesired side effects.

In certain embodiments, the histamine H$_1$-receptor agonist is histamine, HTMT (histamine trifluoromethyl toluidide), 2-pyridylethylamine, 2-thiazolylethylamine, or an isotopic variant thereof, or a pharmaceutically acceptable salt, hydrate, or solvate thereof. In certain embodiments, the histamine H$_1$-receptor agonist, histamine H$_2$-receptor agonist, or histamine H$_3$-receptor antagonist is betahistine, betazole, impentamine, or an isotopic variant thereof; or a pharmaceutically acceptable salt, hydrate, or solvate thereof. In certain embodiments, the histamine H$_1$-receptor agonist, histamine H$_2$-receptor agonist, or histamine H$_3$-receptor antagonist is betazole or an isotopic variant thereof; or a pharmaceutically acceptable salt, hydrate, or solvate thereof. In certain embodiments, the histamine H$_1$-receptor agonist, histamine H$_2$-receptor agonist, or histamine H$_3$-receptor antagonist is impentamine or an isotopic variant thereof; or a pharmaceutically acceptable salt, hydrate, or solvate thereof.

In certain embodiments, the histamine H$_1$-receptor agonist, histamine H$_2$-receptor agonist, or histamine H$_3$-receptor antagonist is 4-methylhistamine, dimaprit, impromidine, or an isotopic variant thereof; or a pharmaceutically acceptable salt, hydrate, or solvate thereof.

In certain embodiments, the histamine H$_1$-receptor agonist, histamine H$_2$-receptor agonist, or histamine H$_3$-receptor antagonist is A-349,821, ABT-239, betahistine, burimamide, ciproxifan, clobenpropit, conessine, failproxifan, impentamine, indophenpropit, irdabisant, pitolisant, theioperamide, VUF-5681 (4-[3-(1H-imidazol-4-yl)propyl]piperidine), or an isotopic variant thereof; or a pharmaceutically acceptable salt, hydrate, or solvate thereof. In certain embodiments, the histamine H$_1$-receptor agonist, histamine H$_2$-receptor agonist, or histamine H$_3$-receptor antagonist is betahistine or an isotopic variant thereof, or a pharmaceutically acceptable salt, hydrate, or solvate thereof. In certain embodiments, the histamine H$_1$-receptor agonist, histamine H$_2$-receptor agonist, or histamine H$_3$-receptor antagonist is betahistine hydrochloride.

In certain embodiments, the histamine H$_1$-receptor agonist, histamine H$_2$-receptor agonist, or histamine H$_3$-receptor antagonist is a metabolite of betahistine. In certain embodiments, the metabolite is 2-(2-aminoethyl)pyridine, 2-(2-hydroxyethyl)pyridine, or pyridylacetic acid. In certain embodiments, the histamine H$_1$-receptor agonist, histamine H$_2$-receptor agonist, or histamine H$_3$-receptor antagonist is 2-(2-aminoethyl)pyridine, 2-(2-hydroxyethyl)pyridine, or pyridylacetic acid.

In one embodiment, provided herein is a pharmaceutical composition comprising (i) betahistine, or a metabolite thereof, or an isotopic variant thereof; or a pharmaceutically acceptable salt, hydrate, or solvate thereof, and (ii) one or more compounds, wherein each compound is independently a PDE inhibitor, an adenosine receptor antagonist, a calcium channel blocker, or a β$_2$-adrenergic receptor agonist.

In another embodiment, provided herein is a pharmaceutical composition comprising (i) betahistine, or a metabolite thereof, or an isotopic variant thereof; or a pharmaceutically acceptable salt, hydrate, or solvate thereof; and (ii) a PDE inhibitor, an adenosine receptor antagonist, a calcium channel blocker, or a β$_2$-adrenergic receptor agonist.

In one embodiment, the pharmaceutical composition comprises (i) betahistine, or a metabolite thereof, or an isotopic variant thereof; or a pharmaceutically acceptable salt, hydrate, or solvate thereof, and (ii) a PDE inhibitor or an adenosine receptor antagonist. In another embodiment, the pharmaceutical composition comprises (i) betahistine, or a metabolite thereof, or an isotopic variant thereof; or a pharmaceutically acceptable salt, hydrate, or solvate thereof, and (ii) a calcium channel blocker. In yet another embodiment, the pharmaceutical composition comprises (i) betahistine, or a metabolite thereof, or an isotopic variant thereof; or a pharmaceutically acceptable salt, hydrate, or solvate thereof, and (ii) a β$_2$-adrenergic receptor agonist.

In yet another embodiment, provided herein is a pharmaceutical composition comprising (i) betahistine, or a metabolite thereof, or an isotopic variant thereof; or a pharmaceutically acceptable salt, hydrate, or solvate thereof; and (ii) two compounds, wherein each compound is independently a PDE inhibitor, an adenosine receptor antagonist, a calcium channel blocker, or a β$_2$-adrenergic receptor agonist.

In one embodiment, the pharmaceutical composition comprises (i) betahistine, or a metabolite thereof, or an isotopic variant thereof; or a pharmaceutically acceptable salt, hydrate, or solvate thereof; (ii) a PDE inhibitor or adenosine receptor antagonist; and (iii) a calcium channel blocker. In another embodiment, the pharmaceutical composition comprises (i) betahistine, or a metabolite thereof, or an isotopic variant thereof; or a pharmaceutically acceptable salt, hydrate, or solvate thereof; (ii) a PDE inhibitor or adenosine receptor antagonist; and (iii) a β$_2$-adrenergic receptor agonist. In yet another embodiment, the pharmaceutical composition comprises (i) betahistine, or a metabolite thereof, or an isotopic variant thereof; or a pharmaceutically acceptable salt, hydrate, or solvate thereof; (ii) a calcium channel blocker; and (iii) a β$_2$-adrenergic receptor agonist.

In still another embodiment, provided herein is a pharmaceutical composition comprising (i) betahistine, or a metabolite thereof, or an isotopic variant thereof; or a pharmaceutically acceptable salt, hydrate, or solvate thereof; and (ii) three compounds, wherein each compound is independently a PDE inhibitor, an adenosine receptor antagonist, a calcium channel blocker, or a β$_2$-adrenergic receptor agonist.

In one embodiment, the pharmaceutical composition comprises (i) betahistine, or a metabolite thereof, or an isotopic variant thereof; or a pharmaceutically acceptable salt, hydrate, or solvate thereof; (ii) a PDE inhibitor or an adenosine receptor antagonist; (iii) a calcium channel blocker; and (iv) a β$_2$-adrenergic receptor agonist.

In certain embodiments, the betahistine, or a metabolite thereof, or an isotopic variant thereof, or a pharmaceutically acceptable salt, hydrate, or solvate thereof is a solid. In certain embodiments, the betahistine, or a metabolite thereof, or an isotopic variant thereof, or a pharmaceutically acceptable salt, hydrate, or solvate thereof is a crystalline solid. In certain embodiments, the betahistine, or a metabolite thereof, or an isotopic variant thereof, or a pharmaceutically acceptable salt, hydrate, or solvate thereof is an amorphous solid.

In certain embodiments, the weight ratio of (i) the phosphodiesterase inhibitor or adenosine receptor antagonist to (ii) betahistine or a metabolite thereof in a pharmaceutical composition provided herein is ranging from about 2 to about 200, from about 4 to about 100, from about 5 to about 50, or from about 10 to about 30. In certain embodiments, the weight ratio of (i) the phosphodiesterase inhibitor or adenosine receptor antagonist to (ii) betahistine or a metabolite thereof in a pharmaceutical composition provided herein is about 10, about 12, about 14, about 16, about 17, about 18, about 19, about 20, about 21, about 22, about 23, about 24, about 25, about 26, about 27, about 28, about 29, or about 30.

In certain embodiments, the weight ratio of (i) the calcium channel blocker to (ii) betahistine or a metabolite thereof in a pharmaceutical composition provided herein is ranging from about 1 to about 50, from about 1 to about 40, from about 1 to about 20, or from about 1 to about 10. In certain embodiments, the weight ratio of (i) the calcium channel blocker to (ii) betahistine or a metabolite thereof in a pharmaceutical composition provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10. In certain embodiments, the weight ratio of (i) the calcium channel blocker to (ii) betahistine or a metabolite thereof in a pharmaceutical composition provided herein is about 2, about 2.2, about 2.4, about 2.6, about 2.8, about 3, about 3.2, about 3.4, about 3.6, about 3.8, or about 4.

In certain embodiments, the weight ratio of (i) betahistine or a metabolite thereof to (ii) the $\beta_2$-adrenoreceptor agonist in a pharmaceutical composition provided herein is ranging from about 1 to about 100, from about 1 to about 50, from about 1 to about 30, or from about 1 to about 20. In certain embodiments, the weight ratio of (i) betahistine or a metabolite thereof to (ii) the $\beta_2$-adrenoreceptor agonist in a pharmaceutical composition provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a pharmaceutical composition provided herein comprises betahistine or a metabolite thereof in the amount ranging from about 0.1 to about 200, from about 0.1 to about 100, from about 0.1 to about 60, from about 0.2 to about 50, from about 0.5 to about 40, or from about 1 to about 30 mg. In certain embodiments, a pharmaceutical composition provided herein comprises betahistine or a metabolite thereof in the amount ranging from about 0.1 to about 200 mg. In certain embodiments, a pharmaceutical composition provided herein comprises betahistine or a metabolite thereof in the amount ranging from about 0.1 to about 100 mg. In certain embodiments, a pharmaceutical composition provided herein comprises betahistine or a metabolite thereof in the amount ranging from about 0.1 to about 60 mg. In certain embodiments, a pharmaceutical composition provided herein comprises betahistine or a metabolite thereof in the amount ranging from about 0.2 to about 50 mg. In certain embodiments, a pharmaceutical composition provided herein comprises betahistine or a metabolite thereof in the amount ranging from about 0.5 to about 40 mg. In certain embodiments, a pharmaceutical composition provided herein comprises betahistine or a metabolite thereof in the amount ranging from about 1 to about 30 mg. In certain embodiments, a pharmaceutical composition provided herein comprises betahistine or a metabolite thereof in the amount of about 1, about 2, about 4, about 6, about 8, about 10, about 12, about 14, about 16, about 18, about 20, about 22, about 24, about 26, about 28, or about 30 mg.

In certain embodiments, a pharmaceutical composition provided herein comprises betahistine or a metabolite thereof in the amount ranging from about 0.02 to about 30, from about 0.05 to about 20, from about 0.1 to about 15, or from about 0.2 to about 10% by weight. In certain embodiments, a pharmaceutical composition provided herein comprises betahistine or a metabolite thereof in the amount ranging from about 0.02 to about 30% by weight. In certain embodiments, a pharmaceutical composition provided herein comprises betahistine or a metabolite thereof in the amount ranging from about 0.05 to about 20% by weight. In certain embodiments, a pharmaceutical composition provided herein comprises betahistine or a metabolite thereof in the amount ranging from 0.1 to about 15% by weight. In certain embodiments, a pharmaceutical composition provided herein comprises betahistine or a metabolite thereof in the amount ranging from 0.2 to about 10% by weight. In certain embodiments, a pharmaceutical composition provided herein comprises betahistine or a metabolite thereof in the amount of about 0.2, about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10% by weight.

In one embodiment, provided herein is a pharmaceutical composition comprising (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) optionally one or more compounds, wherein each compound is independently a calcium channel blocker or a $\beta_2$-adrenergic receptor agonist.

In another embodiment, provided herein is a pharmaceutical composition comprising (i) a xanthine compound or an isotopic variant thereof; or a pharmaceutically acceptable salt, hydrate, or solvate thereof; and (ii) betahistine, or a metabolite thereof, or an isotopic variant thereof; or a pharmaceutically acceptable salt, hydrate, or solvate thereof.

In yet another embodiment, provided herein is a pharmaceutical composition comprising (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof, and (iii) a calcium channel blocker or a $\beta_2$-adrenergic receptor agonist.

In one embodiment, the pharmaceutical composition comprises (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) a calcium channel blocker. In another embodiment, the pharmaceutical composition comprises (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) a $\beta_2$-adrenergic receptor agonist.

In still another embodiment, provided herein is a pharmaceutical composition comprising (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) two compounds, wherein each compound is independently a calcium channel blocker or a $\beta_2$-adrenergic receptor agonist.

In one embodiment, the pharmaceutical composition comprises (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; (iii) a calcium channel blocker; and (iv) a $\beta_2$-adrenergic receptor agonist.

In certain embodiments, the weight ratio of the xanthine compound to betahistine or a metabolite thereof in a pharmaceutical composition provided herein is ranging from about 2 to about 200, from about 4 to about 100, from about 5 to about 50, or from about 10 to about 30. In certain embodiments, the weight ratio of the xanthine compound to betahistine or a metabolite thereof in a pharmaceutical composition provided herein is about 10, about 12, about 14, about 16, about 17, about 18, about 19, about 20, about 21, about 22, about 23, about 24, about 25, about 26, about 27, about 28, about 29, or about 30.

In one embodiment, provided herein is a pharmaceutical composition comprising (i) a dihydropyridine or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof, and (iii) optionally one or more compounds, wherein each compound is independently a phosphodiesterase inhibitor, an adenosine receptor antagonist, or a $\beta_2$-adrenoreceptor agonist.

In another embodiment, provided herein is a pharmaceutical composition comprising (i) a dihydropyridine or an isotopic variant thereof; or a pharmaceutically acceptable salt, hydrate, or solvate thereof; and (ii) betahistine, or a metabolite thereof, or an isotopic variant thereof; or a pharmaceutically acceptable salt, hydrate, or solvate thereof.

In yet another embodiment, provided herein is a pharmaceutical composition comprising (i) a dihydropyridine or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof, and (iii) a phosphodiesterase inhibitor, an adenosine receptor antagonist, and/or a $\beta_2$-adrenoreceptor agonist.

In one embodiment, the pharmaceutical composition comprises (i) a dihydropyridine or an isotopic variant thereof, or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) a phosphodiesterase inhibitor or an adenosine receptor antagonist. In another embodiment, the pharmaceutical composition comprises (i) a dihydropyridine or an isotopic variant thereof, or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) a $\beta_2$-adrenoreceptor agonist.

In still another embodiment, provided herein is a pharmaceutical composition comprising (i) a dihydropyridine or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; and (iii) two compounds, wherein each compound is independently a phosphodiesterase inhibitor, an adenosine receptor antagonist, or a $\beta_2$-adrenoreceptor agonist.

In one embodiment, the pharmaceutical composition comprises (i) a dihydropyridine or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; (iii) a phosphodiesterase inhibitor or an adenosine receptor antagonist; and (iv) a $\beta_2$-adrenoreceptor agonist.

In certain embodiments, the weight ratio of the dihydropyridine to betahistine or a metabolite thereof in a pharmaceutical composition provided herein is ranging from about 1 to about 50, from about 1 to about 40, from about 1 to about 20, or from about 1 to about 10. In certain embodiments, the weight ratio of the dihydropyridine to betahistine or a metabolite thereof in a pharmaceutical composition provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10. In certain embodiments, the weight ratio of the dihydropyridine to betahistine or a metabolite thereof in a pharmaceutical composition provided herein is about 2, about 2.2, about 2.4, about 2.6, about 2.8, about 3.0, about 3.2, about 3.4, about 3.6, about 3.8, or about 4.

In one embodiment, provided herein is a pharmaceutical composition comprising (i) a xanthine compound or an isotopic variant thereof; or a pharmaceutically acceptable salt, hydrate, or solvate thereof; (ii) a dihydropyridine or an isotopic variant thereof; or a pharmaceutically acceptable salt, hydrate, or solvate thereof; (iii) betahistine, or a metabolite thereof, or an isotopic variant thereof; or a pharmaceutically acceptable salt, hydrate, or solvate thereof; and (iv) optionally a $\beta_2$-adrenoreceptor agonist.

$\beta_2$-Adrenoreceptor Agonists

In some embodiments, a pharmaceutical composition provided herein comprises an API that is a $\beta_2$-adrenoreceptor agonist. Similar to PDE inhibitors, adenosine receptor antagonists, calcium channel blockers, histamine $H_1$-receptor agonists; histamine $H_2$-receptor agonists or histamine $H_3$-receptor antagonists, when used in a therapeutically effective amount, a variety of undesirable side effects are associated with $\beta_2$-adrenoreceptor agonists for its currently approved indication(s). $\beta_2$-Adrenoreceptor agonists are known to be useful in the treatment of asthma. One secondary therapeutical effect of this API is that it can increase heart rate and cardiac output. Albuterol is a racemic mixture of R-albuterol and S-albuterol. The molecular mechanism of action of this API includes, but is not limited to, that (i) the (R)-enantiomer (levalbuterol) is responsible for the pharmacologic activity and (ii) the (S)-enantiomer blocks metabolic pathways. The API is known as a short-acting $\beta_2$-adrenergic receptor agonist originally used for the relief of bronchospasm. Additionally, this API can also stimulate the heart $B_1$ receptor. The heart myocardium also has the $B_2$ receptor. By excitement of $B_2$ and $B_1$ receptors, the heart rate can be increased. Side effects of this API include the increase of blood pressure. These undesired side effect can be minimized or eliminated by counteracting effects induced by another API such as a histamine $H_1$- and/or $H_2$-receptor agonist and/or a histamine $H_3$-receptor antagonist (e.g., betahistine) provided herein. Meanwhile, desired effects can be enhanced that include, but are not limited to, increased heart rate and cardiac output using a combination of two or more APIs provided herein.

The present disclosure discloses a surprising finding that, when used as a part of a combination of two or more APIs provided herein, a $\beta_2$-adrenoreceptor agonist is useful in the treatment of bradycardia while avoiding or minimizing certain associated undesired side effects.

In one embodiment, the $\beta_2$-adrenergic receptor agonist is a short-acting $\beta_2$ agonist. In another embodiment, the $\beta_2$-adrenergic receptor agonist is a long-acting $\beta_2$ agonist. In yet another embodiment, the $\beta_2$-adrenergic receptor agonist is an ultra-long-acting $\beta_2$ agonist.

In certain embodiments, the $\beta_2$-adrenergic receptor agonist is albuterol, bambuterol, bitolterol, clenbuterol, fenoterol, formoterol, indacaterol, isoprenaline, levalbuterol, metaproterenol, olodaterol, pirbuterol, procaterol, ritodrine, salbutamol, terbutaline, vilanterol, or an isotopic variant thereof; or a pharmaceutically acceptable salt, hydrate, or solvate thereof. In certain embodiments, the $\beta_2$-adrenergic receptor agonist is albuterol or an isotopic variant thereof; or a pharmaceutically acceptable salt, hydrate, or solvate thereof. In certain embodiments, the $\beta_2$-adrenergic receptor agonist is bambuterol or an isotopic variant thereof; or a pharmaceutically acceptable salt, hydrate, or solvate thereof. In certain embodiments, the $\beta_2$-adrenergic receptor agonist is bitolterol or an isotopic variant thereof; or a pharmaceutically acceptable salt, hydrate, or solvate thereof. In certain embodiments, the $\beta_2$-adrenergic receptor agonist is clenbuterol or an isotopic variant thereof, or a pharmaceutically acceptable salt, hydrate, or solvate thereof. In certain embodiments, the $\beta_2$-adrenergic receptor agonist is fenoterol or an isotopic variant thereof; or a pharmaceutically acceptable salt, hydrate, or solvate thereof. In certain embodiments, the $\beta_2$-adrenergic receptor agonist is formoterol or an isotopic variant thereof; or a pharmaceutically acceptable salt, hydrate, or solvate thereof. In certain embodiments, the $\beta_2$-adrenergic receptor agonist is indacaterol or an isotopic variant thereof; or a pharmaceutically acceptable salt, hydrate, or solvate thereof. In certain embodiments, the $\beta_2$-adrenergic receptor agonist is isoprenaline or an isotopic variant thereof; or a pharmaceutically acceptable salt, hydrate, or solvate thereof. In certain embodiments, the $\beta_2$-adrenergic receptor agonist is levalbuterol or an isotopic variant thereof; or a pharmaceutically acceptable salt, hydrate, or solvate thereof. In certain embodiments, the $\beta_2$-adrenergic receptor agonist is metaproterenol or an isotopic variant thereof; or a pharmaceutically acceptable salt, hydrate, or solvate thereof.

In certain embodiments, the $\beta_2$-adrenergic receptor agonist is olodaterol or an isotopic variant thereof; or a pharmaceutically acceptable salt, hydrate, or solvate thereof. In certain embodiments, the $\beta_2$-adrenergic receptor agonist is pirbuterol or an isotopic variant thereof; or a pharmaceutically acceptable salt, hydrate, or solvate thereof. In certain embodiments, the $\beta_2$-adrenergic receptor agonist is procaterol or an isotopic variant thereof; or a pharmaceutically acceptable salt, hydrate, or solvate thereof. In certain embodiments, the $\beta_2$-adrenergic receptor agonist is ritodrine or an isotopic variant thereof; or a pharmaceutically acceptable salt, hydrate, or solvate thereof. In certain embodiments, the $\beta_2$-adrenergic receptor agonist is salbutamol or an isotopic variant thereof; or a pharmaceutically acceptable salt, hydrate, or solvate thereof. In certain embodiments, the $\beta_2$-adrenergic receptor agonist is terbutaline or an isotopic variant thereof; or a pharmaceutically acceptable salt, hydrate, or solvate thereof. In certain embodiments, the $\beta_2$-adrenergic receptor agonist is vilanterol or an isotopic variant thereof; or a pharmaceutically acceptable salt, hydrate, or solvate thereof.

In certain embodiments, the $\beta_2$-adrenergic receptor agonist is arfomoterol, bupherine, dopexamine, epinephrine, isoestarine, isoproterenol, levosalbutamol, orciprenaline, salmeterol, or an isotopic variant thereof; or a pharmaceutically acceptable salt, hydrate, or solvate thereof. In certain embodiments, the $\beta_2$-adrenergic receptor agonist is arfomoterol or an isotopic variant thereof, or a pharmaceutically acceptable salt, hydrate, or solvate thereof. In certain embodiments, the $\beta_2$-adrenergic receptor agonist is bupherine or an isotopic variant thereof, or a pharmaceutically acceptable salt, hydrate, or solvate thereof. In certain embodiments, the $\beta_2$-adrenergic receptor agonist is dopexamine or an isotopic variant thereof, or a pharmaceutically acceptable salt, hydrate, or solvate thereof. In certain embodiments, the $\beta_2$-adrenergic receptor agonist is epinephrine or an isotopic variant thereof; or a pharmaceutically acceptable salt, hydrate, or solvate thereof. In certain embodiments, the $\beta_2$-adrenergic receptor agonist is isoestarine or an isotopic variant thereof; or a pharmaceutically acceptable salt, hydrate, or solvate thereof. In certain embodiments, the $\beta_2$-adrenergic receptor agonist is isoproterenol or an isotopic variant thereof; or a pharmaceutically acceptable salt, hydrate, or solvate thereof. In certain embodiments, the $\beta_2$-adrenergic receptor agonist is levosalbutamol or an isotopic variant thereof; or a pharmaceutically acceptable salt, hydrate, or solvate thereof. In certain embodiments, the $\beta_2$-adrenergic receptor agonist is orciprenaline or an isotopic variant thereof; or a pharmaceutically acceptable salt, hydrate or solvate thereof. In certain embodiments, the $\beta_2$-adrenergic receptor agonist is salmeterol or an isotopic variant thereof; or a pharmaceutically acceptable salt, hydrate, or solvate thereof.

In one embodiment, provided herein is a pharmaceutical composition comprising (i) albuterol, or an enantionmer, a mixture of enantiomers; or levabuterol; or an isotopic variant thereof; or a pharmaceutically acceptable salt, hydrate, or solvate thereof, and (ii) one or more compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In another embodiment, provided herein is a pharmaceutical composition comprising (i) albuterol, or an enantionmer, a mixture of enantiomers; or levabuterol; or an isotopic variant thereof; or a pharmaceutically acceptable salt, hydrate, or solvate thereof, and (ii) a compound that is a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; and (ii) a PDE inhibitor or an adenosine receptor antagonist. In another embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; and (ii) a calcium channel blocker. In yet another embodiment, the pharmaceutical composition comprises (i) albuterol, or an enantionmer, a mixture of enantiomers; or levabuterol; or an isotopic variant thereof;

or a pharmaceutically acceptable salt, hydrate, or solvate thereof; and (ii) a histamine $H_1$-receptor agonist, a histamine $H_2$-receptor agonist, or a histamine $H_3$-receptor antagonist.

In yet another embodiment, provided herein is a pharmaceutical composition comprising (i) albuterol, or an enantionmer, a mixture of enantiomers; or levabuterol; or an isotopic variant thereof; or a pharmaceutically acceptable salt, hydrate, or solvate thereof; and (ii) two compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; (ii) a PDE inhibitor or adenosine receptor antagonist; and (iii) a calcium channel blocker. In another embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; (ii) a PDE inhibitor or adenosine receptor antagonist; and (iii) a histamine $H_1$-receptor agonist, a histamine $H_2$-receptor agonist, or a histamine $H_3$-receptor antagonist. In yet another embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; (ii) a calcium channel blocker; and (iii) a histamine $H_1$-receptor agonist, a histamine $H_2$-receptor agonist, or a histamine $H_3$-receptor antagonist.

In still another embodiment, provided herein is a pharmaceutical composition comprising (i) albuterol, or an enantionmer, a mixture of enantiomers; or levabuterol; or an isotopic variant thereof; or a pharmaceutically acceptable salt, hydrate, or solvate thereof; and (ii) three compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, the pharmaceutical composition comprises (i) albuterol, or an enantionmer, a mixture of enantiomers; or levabuterol; or an isotopic variant thereof; or a pharmaceutically acceptable salt, hydrate, or solvate thereof; (ii) a PDE inhibitor or an adenosine receptor antagonist; (iii) a calcium channel blocker; and (iv) a histamine $H_1$-receptor agonist, a histamine $H_2$-receptor agonist, or a histamine $H_3$-receptor antagonist.

In certain embodiments, the albuterol, or an enantionmer, a mixture of enantiomers; or levabuterol; or an isotopic variant thereof; or a pharmaceutically acceptable salt, hydrate, or solvate thereof; is a solid. In certain embodiments, the albuterol, or an enantionmer, a mixture of enantiomers; or levabuterol; or an isotopic variant thereof; or a pharmaceutically acceptable salt, hydrate, or solvate thereof; is a crystalline solid. In certain embodiments, the albuterol, or an enantionmer, a mixture of enantiomers; or levabuterol; or an isotopic variant thereof; or a pharmaceutically acceptable salt, hydrate, or solvate thereof; is an amorphous solid.

In certain embodiments, the weight ratio of (i) the phosphodiesterase inhibitor or adenosine receptor antagonist to (ii) albuterol or levalbuterol in a pharmaceutical composition provided herein is ranging from about 1 to about 1,000, from about 10 to about 500, from about 20 to about 400, or from about 40 to about 300. In certain embodiments, the weight ratio of (i) the phosphodiesterase inhibitor or adenosine receptor antagonist to (ii) albuterol or levalbuterol in a pharmaceutical composition provided herein is about 40, about 60, about 70, about 80, about 90, about 100, about 110, about 120, about 130, about 140, about 160, about 180, about 200, about 220, about 240, about 260, about 280, or about 300.

In certain embodiments, the weight ratio of (i) the calcium channel blocker to (ii) albuterol in a pharmaceutical composition provided herein is ranging from about 1 to about 100, from about 5 to about 50, or from about 5 to about 30. In certain embodiments, the weight ratio of (i) the calcium channel blocker to (ii) albuterol or levalbuterol in a pharmaceutical composition provided herein is about 5, about 6, about 8, about 10, about 12, about 14, about 16, about 18, about 20, about 22, about 24, about 26, about 28, or about 30.

In certain embodiments, the weight ratio of (i) the histamine $H_1$-receptor agonist, the histamine $H_2$-receptor agonist, or the histamine $H_3$-receptor antagonist to (ii) albuterol or levalbuterol in a pharmaceutical composition provided herein is ranging from about 1 to about 100, from about 1 to about 50, from about 1 to about 30, or from about 1 to about 20. In certain embodiments, the weight ratio of (i) the histamine $H_1$-receptor agonist, the histamine $H_2$-receptor agonist, or the histamine $H_3$-receptor antagonist to (ii) albuterol or levalbuterol in a pharmaceutical composition provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a pharmaceutical composition provided herein comprises albuterol or levalbuterol (micronized or non-micronized) in the amount ranging from about 0.01 to about 60, from about 0.01 to about 40, from about 0.05 to about 30, from about 0.05 to about 20, from about 0.1 to about 10, or from about 0.1 to about 5 mg. In certain embodiments, a pharmaceutical composition provided herein comprises albuterol or levalbuterol in the amount ranging from about 0.01 to about 60 mg. In certain embodiments, a pharmaceutical composition provided herein comprises albuterol or levalbuterol in the amount ranging from about 0.05 to about 30 mg. In certain embodiments, a pharmaceutical composition provided herein comprises albuterol or levalbuterol in the amount ranging from about 0.05 to about 20 mg. In certain embodiments, a pharmaceutical composition provided herein comprises albuterol or levalbuterol in the amount ranging from about 0.1 to about 10 mg. In certain embodiments, a pharmaceutical composition provided herein comprises albuterol or levalbuterol in the amount ranging from about 0.1 to about 5 mg. In certain embodiments, a pharmaceutical composition provided herein comprises albuterol or levalbuterol in the amount of about 0.1, about 0.5, about 1.0, about 1.5, about 2.0, about 2.5, about 3.0, about 3.5, about 4.0, about 4.5, or about 5 mg.

In certain embodiments, a pharmaceutical composition provided herein comprises albuterol or levalbuterol in the amount ranging from about 0.005 to about 10, from about 0.01 to about 8, from about 0.02 to about 6, from about 0.05 to about 5% by weight. In certain embodiments, a pharmaceutical composition provided herein comprises albuterol or levalbuterol in the amount ranging from about 0.005 to about 10% by weight. In certain embodiments, a pharmaceutical composition provided herein comprises albuterol or levalbuterol in the amount ranging from about 0.01 to about 8% by weight. In certain embodiments, a pharmaceutical composition provided herein comprises albuterol or levalbuterol in the amount ranging from about 0.02 to about 6% by weight. In certain embodiments, a pharmaceutical composition provided herein comprises albuterol or levalbuterol in the amount ranging from about 0.05 to about 5% by weight. In certain embodiments, a pharmaceutical composition provided herein comprises albuterol or levalbuterol in the amount of about 0.1, about 0.5, about 1.0, about 1.5, about 2.0, about 2.5, about 3.0, about 3.5, about 4.0, about 4.5, or about 5% by weight.

In one embodiment, provided herein is a pharmaceutical composition comprising (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) optionally one or more compounds, wherein each compound is independently a calcium channel blocker, a histamine $H_1$-receptor agonist, a histamine $H_2$-receptor agonist, or a histamine $H_3$-receptor antagonist.

In another embodiment, provided herein is a pharmaceutical composition comprising (i) a xanthine compound or an isotopic variant thereof; or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, provided herein is a pharmaceutical composition comprising (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker, a histamine $H_1$-receptor agonist, a histamine $H_2$-receptor agonist, or a histamine $H_3$-receptor antagonist.

In one embodiment, the pharmaceutical composition comprises (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker. In another embodiment, the pharmaceutical composition comprises (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof, or a pharmaceutically acceptable salt, hydrate, or solvate thereof; and (iii) a histamine $H_1$-receptor agonist, a histamine $H_2$-receptor agonist, or a histamine $H_3$-receptor antagonist.

In still another embodiment, provided herein is a pharmaceutical composition comprising (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) two compounds, wherein each compound is independently a calcium channel blocker, a histamine $H_1$-receptor agonist, a histamine $H_2$-receptor agonist, or a histamine $H_3$-receptor antagonist.

In one embodiment, the pharmaceutical composition comprises (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a calcium channel blocker; and (iv) a histamine $H_1$-receptor agonist, a histamine $H_2$-receptor agonist, or a histamine $H_3$-receptor antagonist.

In certain embodiments, the weight ratio of (i) the xanthine compound to (ii) albuterol or levalbuterol in a pharmaceutical composition provided herein is ranging from about 1 to about 1,000, from about 10 to about 500, from about 20 to about 400, or from about 40 to about 300. In certain embodiments, the weight ratio of (i) the xanthine compound to (ii) albuterol or levalbuterol in a pharmaceutical composition provided herein is about 40, about 60, about 80, about 100, about 120, about 140, about 160, about 180, about 200, about 220, about 240, about 260, about 280, or about 300.

In one embodiment, provided herein is a pharmaceutical composition comprising (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) optionally one or more compounds, wherein each compound is independently a phosphodiesterase inhibitor, an adenosine receptor antagonist, a histamine $H_1$-receptor agonist, a histamine $H_2$-receptor agonist, or a histamine $H_3$-receptor antagonist.

In another embodiment, provided herein is a pharmaceutical composition comprising (i) a dihydropyridine or an isotopic variant thereof, or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, provided herein is a pharmaceutical composition comprising (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a phosphodiesterase inhibitor, an adenosine receptor antagonist; and (iv) a histamine $H_1$-receptor agonist, a histamine $H_2$-receptor agonist, or a histamine $H_3$-receptor antagonist.

In one embodiment, the pharmaceutical composition comprises (i) a dihydropyridine or an isotopic variant thereof, or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor or an adenosine receptor antagonist. In another embodiment, the pharmaceutical composition comprises (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a histamine $H_1$-receptor agonist, a histamine $H_2$-receptor agonist, or a histamine $H_3$-receptor antagonist.

In still another embodiment, provided herein is a pharmaceutical composition comprising (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof, and (iii) two compounds, wherein each compound is independently a phosphodiesterase inhibitor, an adenosine receptor antagonist, a histamine $H_1$-receptor agonist, a histamine $H_2$-receptor agonist, or a histamine $H_3$-receptor antagonist.

In one embodiment, the pharmaceutical composition comprises (i) a dihydropyridine or an isotopic variant thereof, or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a phosphodiesterase inhibitor or an adenosine receptor antagonist; and (iv) a histamine $H_1$-receptor agonist, a histamine $H_2$-receptor agonist, or a histamine $H_3$-receptor antagonist.

In certain embodiments, the weight ratio of (i) the dihydropyridine to (ii) albuterol or levalbuterol in a pharmaceutical composition provided herein is ranging from about 1 to about 100, from about 5 to about 50, or from about 5 to about 30. In certain embodiments, the weight ratio of (i) the dihydropyridine to (ii) albuterol or levalbuterol in a pharmaceutical composition provided herein is about 5, about 10, about 12, about 14, about 16, about 18, about 20, about 22, about 24, about 26, about 28, or about 30.

In one embodiment, provided herein is a pharmaceutical composition comprising (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) optionally one or more compounds, wherein each compound is independently a phosphodiesterase inhibitor, an adenosine receptor antagonist, or a calcium channel blocker.

In another embodiment, provided herein is a pharmaceutical composition comprising (i) betahistine, or a metabolite thereof, or an isotopic variant thereof; or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, provided herein is a pharmaceutical composition comprising (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor, an adenosine receptor antagonist, or a calcium channel blocker.

In one embodiment, the pharmaceutical composition comprises (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor or an adenosine receptor antagonist. In another embodiment, the pharmaceutical composition comprises (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker.

In still another embodiment, provided herein is a pharmaceutical composition comprising (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) two compounds, wherein each compound is independently a phosphodiesterase inhibitor, an adenosine receptor antagonist, or a calcium channel blocker.

In one embodiment, the pharmaceutical composition comprises (i) betahistine, or a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a phosphodiesterase inhibitor or an adenosine receptor antagonist; and (iv) a calcium channel blocker.

In certain embodiments, the weight ratio of (i) betahistine or a metabolite thereof to (ii) albuterol or levalbuterol in a pharmaceutical composition provided herein is ranging from about 1 to about 100, from about 1 to about 50, from about 1 to about 30, or from about 1 to about 20. In certain embodiments, the weight ratio of (i) betahistine or a metabolite thereof to (ii) albuterol or levalbuterol in a pharmaceutical composition provided herein is about 1, about 2, about 3, about 4, about 5, about 6, about 7, about 8, about 9, about 10, about 11, about 12, about 13, about 14, about 15, about 16, about 17, about 18, about 19, or about 20.

In one embodiment, provided herein is a pharmaceutical composition comprising (i) a xanthine compound or an isotopic variant thereof, or a pharmaceutically acceptable salt, hydrate, or solvate thereof, (ii) a dihydropyridine or an isotopic variant thereof, or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof; and (iv) optionally a histamine $H_1$-receptor agonist, a histamine $H_2$-receptor agonist, or a histamine $H_3$-receptor antagonist.

In another embodiment, provided herein is a pharmaceutical composition comprising (i) a xanthine compound or an isotopic variant thereof; or a pharmaceutically acceptable salt, hydrate, or solvate thereof; (ii) betahistine, or a metabolite thereof, or an isotopic variant thereof; or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof, and (iv) optionally a calcium channel blocker.

In yet another embodiment, provided herein is a pharmaceutical composition comprising (i) a dihydropyridine or an isotopic variant thereof, or a pharmaceutically acceptable salt, hydrate, or solvate thereof; (ii) betahistine, or a metabolite thereof, or an isotopic variant thereof; or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof, and (iv) optionally a PDE inhibitor or an adenosine receptor antagonist.

In still another embodiment, provided herein is a pharmaceutical composition comprising (i) a xanthine compound or an isotopic variant thereof; or a pharmaceutically acceptable salt, hydrate, or solvate thereof, (ii) a dihydropyridine or an isotopic variant thereof; or a pharmaceutically acceptable salt, hydrate, or solvate thereof; (iii) betahistine, or a metabolite thereof, or an isotopic variant thereof; or a pharmaceutically acceptable salt, hydrate, or solvate thereof, and (iv) albuterol, or an enantionmer, a mixture of enantiomers; or levalbuterol; or an isotopic variant thereof, or a pharmaceutically acceptable salt, hydrate, or solvate thereof.

In one embodiment, the xanthine compound is aminophylline or theophylline. In another embodiment, the dihydropyridine is nifedipine.

In one embodiment, a pharmaceutical composition provided herein comprises aminophylline or theophylline. In another embodiment, a pharmaceutical composition provided herein comprises nifedipine. In yet another embodiment, a pharmaceutical composition provided herein comprises betahistine or betahistine hydrochloride. In still another embodiment, a pharmaceutical composition provided herein comprises albuterol, albuterol hydrochloride, levalbuterol, or levalbuterol hydrochloride.

In one embodiment, a pharmaceutical composition provided herein comprises (i) aminophylline or theophylline and (ii) nifedipine.

In another embodiment, a pharmaceutical composition provided herein comprises (i) aminophylline or theophylline and (ii) betahistine or betahistine hydrochloride.

In yet another embodiment, a pharmaceutical composition provided herein comprises (i) aminophylline or theophylline and (ii) albuterol, albuterol hydrochloride, levalbuterol, or levalbuterol hydrochloride.

In yet another embodiment, a pharmaceutical composition provided herein comprises (i) nifedipine and (ii) betahistine or betahistine hydrochloride.

In yet another embodiment, a pharmaceutical composition provided herein comprises (i) nifedipine and (ii) albuterol, albuterol hydrochloride, levalbuterol, or levalbuterol hydrochloride.

In still another embodiment, a pharmaceutical composition provided herein comprises (i) betahistine or betahistine hydrochloride; and (ii) albuterol, albuterol hydrochloride, levalbuterol, or levalbuterol hydrochloride.

In one embodiment, a pharmaceutical composition provided herein comprises (i) aminophylline or theophylline; (ii) nifedipine; and (iii) betahistine or betahistine hydrochloride.

In another embodiment, a pharmaceutical composition provided herein comprises (i) aminophylline or theophylline; (ii) nifedipine; and (iii) albuterol, albuterol hydrochloride, levalbuterol, or levalbuterol hydrochloride.

In yet another embodiment, a pharmaceutical composition provided herein comprises (i) nifedipine; (ii) betahistine or betahistine hydrochloride; and (iii) albuterol, albuterol hydrochloride, levalbuterol, or levalbuterol hydrochloride.

In one embodiment, a pharmaceutical composition provided herein comprises (i) aminophylline or theophylline; (ii) nifedipine; (iii) betahistine or betahistine hydrochloride; and (iv) albuterol, albuterol hydrochloride, levalbuterol, or levalbuterol hydrochloride.

In certain embodiments, aminophylline is a solid. In certain embodiments, aminophylline is a crystalline solid. In certain embodiments, aminophylline is an amorphous solid. In certain embodiments, theophylline is a solid. In certain embodiments, theophylline is a crystalline solid. In certain embodiments, theophylline is an amorphous solid.

In certain embodiments, nifedipine is a solid. In certain embodiments, nifedipine is a crystalline solid. In certain embodiments, nifedipine is an amorphous solid.

In certain embodiments, the weight ratio of theophylline to nifedipine in a pharmaceutical composition provided herein is ranging from about 1 to about 180, from about 2 to about 100, from about 2 to about 50, or from about 2 to about 20. In certain embodiments, the weight ratio of theophylline to nifedipine in a pharmaceutical composition provided herein is ranging from about 1 to about 180. In certain embodiments, the weight ratio of theophylline to nifedipine in a pharmaceutical composition provided herein is ranging from about 2 to about 100. In certain embodiments, the weight ratio of theophylline to nifedipine in a pharmaceutical composition provided herein is ranging from about 2 to about 50. In certain embodiments, the weight ratio of theophylline to nifedipine in a pharmaceutical composition provided herein is ranging from about 2 to about 20. In certain embodiments, the weight ratio of theophylline to nifedipine in a pharmaceutical composition provided herein is about 2, about 4, about 6, about 8, about 10, about 12, about 14, about 16, about 18, or about 20.

In certain embodiments, the weight ratio of theophylline to betahistine in a pharmaceutical composition provided herein is ranging from about 2 to about 200, from about 4 to about 100, from about 5 to about 50, or from about 10 to about 30. In certain embodiments, the weight ratio of theophylline to betahistine in a pharmaceutical composition provided herein is about 10, about 12, about 14, about 16, about 18, about 20, about 22, about 24, about 26, about 28, or about 30.

In certain embodiments, the weight ratio of theophylline to albuterol or levalbuterol in a pharmaceutical composition provided herein is ranging from about 1 to about 1,000, from about 10 to about 500, from about 20 to about 200, or from about 40 to about 300. In certain embodiments, the weight ratio of theophylline to albuterol or levalbuterol in a pharmaceutical composition provided herein is about 40, about 60, about 80, about 100, about 120, about 140, about 160, about 180, about 200, about 220, about 240, about 260, about 280, or about 300.

In certain embodiments, the weight ratio of nifedipine to betahistine in a pharmaceutical composition provided herein is ranging from about 1 to about 50, from about 1 to about 40, from about 1 to about 20, or from about 1 to about 10. In certain embodiments, the weight ratio of nifedipine to betahistine in a pharmaceutical composition provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, the weight ratio of betahistine to albuterol or levalbuterol in a method provided herein is ranging from about 1 to about 100, from about 5 to about 50, from about 5 to about 30, or from about 1 to about 20. In certain embodiments, the weight ratio of betahistine to albuterol or levalbuterol in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a pharmaceutical composition provided herein comprises theophylline in the amount ranging from about 1 to about 1,200, from about 1 to about 1,000, from about 1 to about 800, from about 1 to about 600, from about 2 to about 300, or from about 10 to about 200 mg. In certain embodiments, a pharmaceutical composition provided herein comprises theophylline in the amount ranging from about 1 to about 1,200 mg. In certain embodiments, a pharmaceutical composition provided herein comprises theophylline in the amount ranging from about 1 to about 1,000 mg. In certain embodiments, a pharmaceutical composition provided herein comprises theophylline in the amount ranging from about 1 to about 800 mg. In certain embodiments, a pharmaceutical composition provided herein comprises theophylline in the amount ranging from about 1 to about 600 mg. In certain embodiments, a pharmaceutical composition provided herein comprises theophylline in the amount ranging from about 2 to about 300 mg. In certain embodiments, a pharmaceutical composition provided herein comprises theophylline in the amount ranging from about 10 to about 200 mg. In certain embodiments, a pharmaceutical composition provided herein comprises theophylline in the amount of about 10, about 20, about 40, about 60, about 80, about 100, about 120, about 140, about 160, about 180, or about 200 mg.

In certain embodiments, a pharmaceutical composition provided herein comprises aminophylline in the amount ranging from about 1 to about 1,200, from about 1 to about 1,000, from about 1 to about 800, from about 1 to about 600, from about 2 to about 300, or from about 10 to about 200 mg. In certain embodiments, a pharmaceutical composition provided herein comprises theophylline in the amount ranging from about 1 to about 1,200 mg. In certain embodiments, a pharmaceutical composition provided herein comprises theophylline in the amount ranging from about 1 to about 1,000 mg. In certain embodiments, a pharmaceutical composition provided herein comprises theophylline in the amount ranging from about 1 to about 800 mg. In certain embodiments, a pharmaceutical composition provided herein comprises theophylline in the amount ranging from about 1 to about 600 mg. In certain embodiments, a pharmaceutical composition provided herein comprises theophylline in the amount ranging from about 2 to about 300 mg. In certain embodiments, a pharmaceutical composition provided herein comprises theophylline in the amount ranging from about 10 to about 200 mg. In certain embodiments, a pharmaceutical composition provided herein comprises theophylline in the amount of about 10, about 20, about 40, about 60, about 80, about 100, about 120, about 140, about 160, about 180, or about 200 mg.

In certain embodiments, a pharmaceutical composition provided herein comprises nifedipine (micronized or non-micronized) in the amount ranging from about 0.1 to about 200, about 0.1 to about 100, about 0.2 to about 80, from about 1 to about 50, from about 1 to about 30, or from about 1 to about 20 mg. In certain embodiments, a pharmaceutical composition provided herein comprises nifedipine in the amount ranging from about 0.1 to about 200 mg. In certain embodiments, a pharmaceutical composition provided herein comprises nifedipine in the amount ranging from about 0.1 to about 100 mg. In certain embodiments, a pharmaceutical composition provided herein comprises nifedipine in the amount ranging from about 0.2 to about 80 mg. In certain embodiments, a pharmaceutical composition provided herein comprises nifedipine in the amount ranging from about 1 to about 50 mg. In certain embodiments, a pharmaceutical composition provided herein comprises nifedipine in the amount ranging from about 1 to about 30 mg. In certain embodiments, a pharmaceutical composition provided herein comprises nifedipine in the amount ranging from about 1 to about 20 mg. In certain embodiments, a pharmaceutical composition provided herein comprises nifedipine in the amount of about 1, about 2, about 3, about 4, about 5, about 6, about 7, about 8, about 9, about 10, about 11, about 12, about 13, about 14, about 15, about 16, about 17, about 18, about 19, or about 20 mg.

In certain embodiments, a pharmaceutical composition provided herein comprises theophylline in the amount ranging from about 1 to about 90, from about 2 to about 80, from about 5 to about 60, or from about 5 to about 35% by weight. In certain embodiments, a pharmaceutical composition provided herein comprises theophylline in the amount ranging from about 1 to about 90% by weight. In certain embodiments, a pharmaceutical composition provided herein comprises theophylline in the amount ranging from about 2 to about 80% by weight. In certain embodiments, a pharmaceutical composition provided herein comprises theophylline in the amount ranging from about 5 to about 60% by weight. In certain embodiments, a pharmaceutical composition provided herein comprises theophylline in the amount ranging from about 5 to about 35% by weight. In certain embodiments, a pharmaceutical composition provided herein comprises theophylline in the amount of about 5, about 10, about 20, about 30, or about 35% by weight.

In certain embodiments, a pharmaceutical composition provided herein comprises nifedipine in the amount ranging from about 0.1 to about 30, from about 0.5 to about 20, or from about 1 to about 10% by weight. In certain embodiments, a pharmaceutical composition provided herein comprises nifedipine in the amount ranging from about 0.1 to about 30% by weight. In certain embodiments, a pharmaceutical composition provided herein comprises nifedipine in the amount ranging from about 0.5 to about 20% by weight. In certain embodiments, a pharmaceutical composition provided herein comprises nifedipine in the amount ranging from about 1 to about 10% by weight. In certain embodiments, a pharmaceutical composition provided herein comprises nifedipine in the amount of about 1, about 2, about 3, about 4, about 5, about 6, about 7, about 8, about 9, or about 10% by weight.

In one embodiment, a pharmaceutical composition provided herein comprises (i) a phosphodiesterase inhibitor or an adenosine receptor antagonist in the amount ranging from about 10 to about 200 mg and (ii) a calcium channel blocker in the amount ranging from about 1 to about 20 mg. In another embodiment, a pharmaceutical composition provided herein comprises (i) a phosphodiesterase inhibitor or an adenosine receptor antagonist in the amount ranging from about 5 to about 35% by weight and (ii) a calcium channel blocker in the amount ranging from about 1 to about 10% by weight.

In one embodiment, a pharmaceutical composition provided herein comprises (i) a histamine $H_1$-receptor agonist, a histamine $H_2$-receptor agonist, or a histamine $H_3$-receptor antagonist in the amount ranging from about 1 to about 30 mg and (ii) a $\beta_2$-adrenoreceptor agonist in the amount ranging from about 0.1 to about 5 mg. In another embodiment, a pharmaceutical composition provided herein comprises (i) a histamine $H_1$- and/or $H_2$-receptor agonist, and/or a histamine $H_3$-receptor antagonist in the amount ranging from about 0.2 to about 10% by weight and (ii) a $\beta_2$-adrenoreceptor agonist in the amount ranging from about 0.05 to about 5% by weight.

In one embodiment, a pharmaceutical composition provided herein comprises (i) a phosphodiesterase inhibitor or an adenosine receptor antagonist, in an embodiment, theophylline, aminophylline, or a hydrochloride thereof, in the amount ranging from about 5 to about 90% or from about 10 to about 35% by weight; (ii) a calcium channel blocker, in an embodiment, nifedipine, in the amount ranging from about 1 to about 20% or from about 1 to about 5% by weight; (iii) a histamine $H_1$-receptor agonist, a histamine $H_2$-receptor agonist, or a histamine $H_3$-receptor antagonist, in an embodiment, betahistine, or a metabolite thereof, or a hydrochloride thereof, in the amount ranging from about 0.1 to about 20% or from about 1 to about 5% by weight; (iv) a $\beta_2$-adrenoreceptor agonist, in an embodiment, albuterol, levalbuterol, or a hydrochloride thereof, in the amount ranging from about 0.05 to about 5% or from about 0.1 to about 0.5% by weight; and (v) a pharmaceutically acceptable excipient, in an embodiment, a diluent, a binder, a disintegrate, a glidant, a lubricant, a preservative, or a mixture thereof.

In one embodiment, a pharmaceutical composition provided herein comprises (i) a xanthine compound or an isotopic variant thereof; or a pharmaceutically acceptable salt, hydrate, or solvate thereof in the amount ranging from about 10 to about 200 mg; (ii) a dihydropyridine or an isotopic variant thereof; or a pharmaceutically acceptable salt, hydrate, or solvate thereof in the amount ranging from about 1 to about 20 mg; (iii) betahistine, or a metabolite thereof, or an isotopic variant thereof, or a pharmaceutically acceptable salt thereof in the amount ranging from about 1 to about 20 mg; and (iv) albuterol, levalbuterol, or an isotopic variant thereof, or a pharmaceutically acceptable salt thereof in the amount ranging from about 0.1 to about 5 mg. In another embodiment, a pharmaceutical composition provided herein comprises (i) a xanthine compound or an isotopic variant thereof; or a pharmaceutically acceptable salt, hydrate, or solvate thereof in the amount ranging from about 5 to about 90% by weight; (ii) a dihydropyridine or an isotopic variant thereof; or a pharmaceutically acceptable salt, hydrate, or solvate thereof in the amount ranging from about 1 to about 20% by weight; (iii) betahistine, or a metabolite thereof, or an isotopic variant thereof, or a pharmaceutically acceptable salt thereof in the amount ranging from about 0.1 to about 20% by weight; and (iv) albuterol, levalbuterol, or an isotopic variant thereof, or a pharmaceutically acceptable salt thereof in the amount ranging from about 0.05 to about 5% by weight.

In one embodiment, a pharmaceutical composition provided herein comprises (i) theophylline in the amount ranging from about 10 to about 200 mg; (ii) nifedipine in the amount ranging from about 1 to about 20 mg; (iii) betahistine or a hydrochloride thereof in the amount ranging from about 0.1 to about 20 mg; and (iv) albuterol, levalbuterol, or a hydrochloride thereof in the amount ranging from about 0.1 to about 5 mg. In another embodiment, a pharmaceutical composition provided herein comprises (i) theophylline in the amount ranging from about 5 to about 90% by weight; (ii) nifedipine in the amount ranging from about 1 to about 20% by weight; (iii) betahistine or a hydrochloride thereof in the amount ranging from about 0.1 to about 20% by weight; and (iv) albuterol, levalbuterol or a hydrochloride thereof in the amount ranging from about 0.05 to about 5% by weight.

In one embodiment, a pharmaceutical composition provided herein comprises (i) a xanthine compound, or an isotopic variant thereof; or a pharmaceutically acceptable salt, hydrate, or solvate thereof in the amount ranging from about 10 to about 200 mg; and (ii) a dihydropyridine or an isotopic variant thereof; or a pharmaceutically acceptable salt, hydrate, or solvate thereof in the amount ranging from about 1 to about 20 mg; In another embodiment, a pharmaceutical composition provided herein comprises (i) a xanthine compound or an isotopic variant thereof; or a pharmaceutically acceptable salt, hydrate, or solvate thereof in the amount ranging from about 5 to about 90% by weight; and (ii) a dihydropyridine or an isotopic variant thereof; or a pharmaceutically acceptable salt, hydrate, or solvate thereof in the amount ranging from about 1 to about 20% by weight.

In one embodiment, a pharmaceutical composition provided herein comprises (i) a xanthine compound, or an isotopic variant thereof; or a pharmaceutically acceptable salt, hydrate, or solvate thereof in the amount ranging from about 10 to about 200 mg; (ii) a dihydropyridine or an isotopic variant thereof; or a pharmaceutically acceptable salt, hydrate, or solvate thereof in the amount ranging from about 1 to about 20 mg; and (iii) betahistine, or a metabolite thereof, or an isotopic variant thereof, or a pharmaceutically acceptable salt thereof in the amount ranging from about 1 to about 20 mg; In another embodiment, a pharmaceutical composition provided herein comprises (i) a xanthine compound or an isotopic variant thereof; or a pharmaceutically acceptable salt, hydrate, or solvate thereof in the amount ranging from about 5 to about 90% by weight; (ii) a dihydropyridine or an isotopic variant thereof; or a pharmaceutically acceptable salt, hydrate, or solvate thereof in the amount ranging from about 1 to about 20% by weight; and (iii) betahistine, or a metabolite thereof, or an isotopic variant thereof, or a pharmaceutically acceptable salt thereof in the amount ranging from about 0.1 to about 20% by weight.

In one embodiment, a pharmaceutical composition provided herein comprises (i) theophylline in the amount ranging from about 10 to about 200 mg; (ii) nifedipine in the amount ranging from about 1 to about 20 mg; (iii) betahistine or a hydrochloride thereof in the amount ranging from about 0.1 to about 20 mg; In another embodiment, a pharmaceutical composition provided herein comprises (i) theophylline in the amount ranging from about 5 to about 90% by weight; (ii) nifedipine in the amount ranging from about 1 to about 20% by weight; (iii) betahistine or a hydrochloride thereof in the amount ranging from about 0.1 to about 20% by weight.

In one embodiment, a pharmaceutical composition provided herein comprises (i) theophylline in the amount ranging from about 10 to about 200 mg; (ii) nifedipine in the amount ranging from about 1 to about 20 mg; and (iii) albuterol, levalbuterol, or a hydrochloride thereof in the amount ranging from about 0.1 to about 5 mg. In another embodiment, a pharmaceutical composition provided herein comprises (i) theophylline in the amount ranging from about 5 to about 90% by weight; (ii) nifedipine in the amount ranging from about 1 to about 20% by weight; (iii) albuterol, levalbuterol, or a hydrochloride thereof in the amount ranging from about 0.05 to about 5% by weight.

In one embodiment, a pharmaceutical composition provided herein comprises (i) theophylline in the amount ranging from about 10 to about 200 mg; (ii) betahistine or a hydrochloride thereof in the amount ranging from about 0.1 to about 20 mg; and (iii) albuterol, levalbuterol, or a hydrochloride thereof in the amount ranging from about 0.1 to about 5 mg. In another embodiment, a pharmaceutical composition provided herein comprises (i) theophylline thereof in the amount ranging from about 5 to about 90% by weight; (ii) betahistine or a hydrochloride thereof in the amount ranging from about 0.1 to about 20% by weight; (iii) albuterol, levalbuterol, or a hydrochloride thereof in the amount ranging from about 0.05 to about 5% by weight.

In certain embodiments, a pharmaceutical composition provided herein comprises a diluent, a binder, a disintegrate, a glidant, a lubricant, or a preservative, or a mixture thereof. In certain embodiments, a pharmaceutical composition provided herein comprises a diluent, a binder, a disintegrate, a glidant, a lubricant, and a preservative.

In certain embodiments, the amount of the diluent in a pharmaceutical composition provided herein is ranging from about 10 to about 60, from about 10 to about 50, from about 10 to about 45, or from about 10 to about 35% by weight. In certain embodiments, the amount of the diluent in a pharmaceutical composition provided herein is about 10, about 12, about 14, about 16, about 18, about 20, about 22, about 24, about 26, about 28, about 30, about 32, about 34, or about 35% by weight.

In certain embodiments, the amount of the binder in a pharmaceutical composition provided herein is ranging from about 10 to about 65, about 10 to about 50, about 10 to about 45, or about 10 to about 35% by weight. In certain embodiments, the amount of the binder in a pharmaceutical composition provided herein is about 10, about 12, about 14, about 16, about 18, about 20, about 22, about 24, about 26, about 28, about 30, about 32, about 34, or about 35% by weight.

In certain embodiments, the amount of the disintegrant in a pharmaceutical composition provided herein is ranging from about 1 to about 5%, or from about 1 to about 3% by weight. In certain embodiments, the amount of the disintegrant in a pharmaceutical composition provided herein is about 1, about 1.5, about 2, about 2.5, or about 3% by weight.

In certain embodiments, the amount of the glidant in a pharmaceutical composition provided herein is ranging from about 0.01 to about 0.5, from about 0.02 to about 0.3% by weight. In certain embodiments, the amount of the glidant in a pharmaceutical composition provided herein is about 0.02, about 0.05, about 0.10, about 0.15, about 0.20, about 0.25, or about 0.3% by weight.

In certain embodiments, the amount of the lubricant in a pharmaceutical composition provided herein is ranging from about 0.05 to about 0.8 or from about 0.1 to about 0.5% by weight. In certain embodiments, the amount of the lubricant in a pharmaceutical composition provided herein is about 0.1, about 0.15, about 0.2, about 0.25, about 0.3, about 0.35, about 0.4, about 0.45, or about 0.5% by weight.

In certain embodiments, the amount of the preservative in a pharmaceutical composition provided herein is ranging from about 0.1 to about 2 or from about 0.2 to about 1% by weight. In certain embodiments, the amount of the preservative in a pharmaceutical composition provided herein is about 0.2, about 0.3, about 0.4, about 0.5, about 0.6, about 0.7, about 0.8, about 0.9, or about 1% by weight.

In certain embodiments, a pharmaceutical composition provided herein comprises a diluent in the amount ranging from about 10 to about 65% by weight; the binder is in the amount ranging from about 10 to about 65% by weight; the disintegrant is in the amount ranging from about 1 to about 5% by weight; the glidant is in the amount ranging from about 0.01 to about 0.5% by weight; the lubricant is in the amount ranging from about 0.05 to about 0.8% by weight; and/or the preservative is in the amount ranging from about 0.1 to about 2% by weight.

In certain embodiments, a pharmaceutical composition provided herein further comprises a diluent in the amount ranging from about 50 to about 450 mg, a binder in the amount ranging from about 50 to about 450 mg, a disintegrant in the amount ranging from about 1 to about 25 mg, a glidant in the amount ranging from about 0.1 to about 2 mg, a lubricant in the amount ranging from about 0.2 to about 3 mg, and a preservative in the amount ranging from about 0.5 to about 5 mg.

In certain embodiments, a pharmaceutical composition provided herein comprises a diluent, a binder, a disintegrate, a glidant, a lubricant, or a preservative, or a mixture thereof. In certain embodiments, a pharmaceutical composition provided herein comprises a diluent, a binder, a disintegrate, a glidant, a lubricant, and a preservative.

In certain embodiments, the diluent in a pharmaceutical composition provided herein is microcrystalline cellulose, lactose, or corn starch. In certain embodiments, the diluent in a pharmaceutical composition provided herein is microcrystalline cellulose. In certain embodiments, the binder in a pharmaceutical composition provided herein is mannitol. In certain embodiments, the disintegrant in a pharmaceutical composition provided herein is sodium starch glycolate or crospovidone. In certain embodiments, the disintegrant in a pharmaceutical composition provided herein is sodium starch glycolate. In certain embodiments, the glidant in a pharmaceutical composition provided herein is colloidal silicon dioxide. In certain embodiments, the lubricant in a pharmaceutical composition provided herein is magnesium stearate. In certain embodiments, the preservative in a pharmaceutical composition provided herein is citric acid.

In certain embodiments, in a pharmaceutical composition provided herein, the diluent is microcrystalline cellulose; the binder is mannitol; the disintegrant is sodium starch glycolate; the glidant is colloidal silicon dioxide; the lubricant is magnesium stearate; and the preservative is citric acid.

Without being bound by any theory, a solution provided herein to bradycardia treatment is to take advantages of the side effects (e.g., increasing heart rate and/or cardiac output) of certain therapeutic agents at their prescribed doses for approved indication(s). For example, one of the known side effects of theophylline is a rapid heartbeat, along with an increase in oxygen consumption. One of the known side effects of nifedipine is also a rapid heartbeat, along with a reduction in oxygen consumption. Thus, theophylline and nifedipine are paired together to achieve the desired heart rate increase without a substantial effect on oxygen consumption. One of the known side effects of betahistine is a rapid heartbeat, along with a reduction in blood pressure. One of the known side effects of levalbuterol is a rapid heartbeat, along with an increase in blood pressure. Thus, betahistine and levalbuterol are paired together to achieve the desired heart rate increase without a substantial effect on blood pressure.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2011).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

The pharmaceutical compositions provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Delivery Technology,* 2nd Edition, Rathbone et al., Eds., Marcel Dekker, Inc.: New York, N.Y., 2008).

In one embodiment, a pharmaceutical composition provided herein is formulated in a dosage form for oral administration. In one embodiment, an oral pharmaceutical composition provided herein further comprises one or more pharmaceutically acceptable excipients. In one embodiment, an oral pharmaceutical composition provided herein is formulated as a capsule. In another embodiment, an oral pharmaceutical composition provided herein is formulated as a tablet.

In another embodiment, a pharmaceutical composition provided herein is formulated in a dosage form for parenteral administration. In one embodiment, the parenteral pharmaceutical composition is formulated in a dosage form for intravenous administration. In another embodiment, the parenteral pharmaceutical composition is formulated in a dosage form for intramuscular administration. In yet another embodiment, the parenteral pharmaceutical composition is formulated in a dosage form for subcutaneous administration.

In yet another embodiment, a pharmaceutical composition provided herein is formulated in a dosage form for topical administration.

In certain embodiments, the pharmaceutical compositions provided herein are provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, each active compound in a pharmaceutical composition provided herein is micronized.

A. Oral Administration

A pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), a pharmaceutical composition provided herein can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in a pharmaceutical composition provided herein varies upon the type of formulation, and is readily discernible to those of ordinary skill in the art. The binder or filler may be present from about 50 to about 99% by weight in a pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; and mixtures thereof. The amount of a disintegrant in a pharmaceutical composition provided herein varies upon the type of formulation, and is readily discernible to those of ordinary skill in the art. The amount of a disintegrant in a pharmaceutical composition provided herein varies upon the type of formulation, and is readily discernible to those of ordinary skill in the art. A pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. A pharmaceutical composition provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

A pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrant in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

A pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient.

A pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

A pharmaceutical composition provided herein for oral administration can be also provided in the forms of liposomes, micelles, microspheres, or nanosystems. Micellar dosage forms can be prepared as described in U.S. Pat. No. 6,350,458.

A pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

A pharmaceutical composition provided herein for oral administration can be formulated as immediate or modified release dosage forms, including delayed-, sustained, pulsed-, controlled, targeted-, and programmed-release forms.

B. Parenteral Administration

A pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

A pharmaceutical composition provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

A pharmaceutical composition intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When a pharmaceutical composition provided herein is formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration are provided as ready-to-use sterile solutions. In another embodiment, the pharmaceutical composition is provided as sterile dry soluble products, including lyophilized powders and hypodermic tablets, to be reconstituted with a vehicle prior to use. In yet another embodiment, the pharmaceutical composition is provided as ready-to-use sterile suspensions. In yet another embodiment, the pharmaceutical composition is provided as sterile dry insoluble products to be reconstituted with a vehicle prior to use. In still another embodiment, the pharmaceutical composition is provided as ready-to-use sterile emulsions.

A pharmaceutical composition provided herein for parenteral administration can be formulated as immediate or modified release dosage forms, including delayed-, sustained, pulsed-, controlled, targeted-, and programmed-release forms.

A pharmaceutical composition provided herein for parenteral administration can be formulated as a suspension, solid, semi-solid, or thixotropic liquid, for administration as an implanted depot. In one embodiment, a pharmaceutical composition provided herein is dispersed in a solid inner matrix, which is surrounded by an outer polymeric membrane that is insoluble in body fluids but allows the active ingredient in the pharmaceutical composition diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber, epichlorohydrin rubbers, ethylene/vinyl alcohol copolymer, ethylene/vinyl acetate/vinyl alcohol terpolymer, and ethylene/vinyloxyethanol copolymer.

C. Topical Administration

A pharmaceutical composition provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

A pharmaceutical composition provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of a pharmaceutical composition provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

A pharmaceutical composition provided herein can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

A pharmaceutical composition provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

A pharmaceutical composition provided herein can be administered rectally, urethrally, vaginally, or perivaginally in the forms of suppositories, pessaries, bougies, poultices or cataplasm, pastes, powders, dressings, creams, plasters, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with a pharmaceutical composition provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

A pharmaceutical composition provided herein can be administered ophthalmically in the forms of solutions, suspensions, ointments, emulsions, gel-forming solutions, powders for solutions, gels, ocular inserts, and implants.

A pharmaceutical composition provided herein can be administered intranasally or by inhalation to the respiratory tract. A pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. A pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

A pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of a pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. A pharmaceutical composition provided herein for inhaled/intranasal administration can further comprise a suitable flavor, such as menthol and levomenthol; and/or sweeteners, such as saccharin and saccharin sodium.

A pharmaceutical composition provided herein for topical administration can be formulated to be immediate release or modified release, including delayed-, sustained-, pulsed-, controlled-, targeted, and programmed release.

D. Modified Release

A pharmaceutical composition provided herein can be formulated as a modified release dosage form. As used herein, the term "modified release" refers to a dosage form in which the rate or place of release of the active ingredient (s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. A pharmaceutical composition in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

A pharmaceutical composition provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, a pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(-)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, a pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

A pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

A pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can be substantially modulated via the thickness and porosity of the semipermeable membrane, the composition of the core, and the number, size, and position of the delivery ports.

A pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, a pharmaceutical composition provided herein is formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, a pharmaceutical composition provided herein is formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

A pharmaceutical composition provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with a pharmaceutical composition provided herein to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

A pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or ameliorating one or more symptoms of a cardiovascular disease in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In certain embodiments, the cardiovascular disease is acute myocardial infarction, aortic aneurysms, atherosclerosis, atherosclerosis, atrial fibrillation, atrial flutter, cardiomyopathy, carditis, a cerebrovascular disease, chest pain (angina), a congenital heart disease, a coronary artery disease, endocarditis, hemorrhagic stroke, heart arrhythmia, heart attack, heart block, heart failure, a hypertensive heart disease, an ischemic heart disease, ischemic stroke, left ventricular dysfunction, myocardial fibrosis, myocardial infarction (heart attack), myocardial ischemia, myocarditis, a peripheral artery disease, a peripheral vascular disease, a rheumatic heart disease, stroke, a valvular heart disease, or venous thrombosis.

In one embodiment, the cardiovascular disease is heart attack. In another embodiment, the cardiovascular disease is heart failure. In yet another embodiment, the cardiovascular disease is heart failure associated with abnormal cardiac output. In yet another embodiment, the cardiovascular disease is stroke. In yet another embodiment, the cardiovascular disease is cardiac arrhythmia. In still another embodiment, the cardiovascular disease is venous thrombosis.

In one embodiment, the cardiovascular disease is cardiac arrhythmia. In another embodiment, the cardiovascular disease is bradycardia. In yet another embodiment, cardiovascular disease is sinus bradycardia, sinus arrest, sinus exit block, atrioventricular (AV) block. In still another embodiment, cardiovascular disease is severe sinus bradycardia, sinoatrial block, sinus arrest, or bradycardia-tachycardia syndrome.

In certain embodiments, the cardiovascular disease is heart block. In certain embodiments, the heart block is AV block. In certain embodiments, the AV block is first-degree, second-degree, or third-degree AV block. In certain embodiments, the AV block is Mobitz type I or II second-degree AV block.

In another embodiment, provided herein is a method of treating, preventing, or ameliorating one or more symptoms of bradycardia in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the bradycardia is atrial bradycardia, atrioventricular nodal bradycardia, infantile bradycardia, or ventricular bradycardia. In another embodiment, the bradycardia is respiratory sinus arrhythmia, sinus bradycardia, or sick sinus (SS) bradycardia.

In one embodiment, the bradycardia is asymptomatic bradycardia. In another embodiment, the bradycardia is symptomatic bradycardia.

In one embodiment, the bradycardia is early stage bradycardia. In another embodiment, the bradycardia is severe bradycardia. In one embodiment, the bradycardia is symptomatic bradycardia due to sick sinus symptom.

In certain embodiments, the bradycardia is associated with AV block. In certain embodiments, the bradycardia is associated with first-degree, second-degree, or third-degree AV block. In certain embodiments, the bradycardia is associated with Mobitz type I or II second-degree AV block.

In certain embodiments, the subject to be treated with a pharmaceutical composition or method provided herein does not have chronic obstructive pulmonary disease.

In certain embodiments, the subject after being treated with a pharmaceutical composition or method provided herein has an increase in resting pulse rate from about 28-45 BPM to about 40-68 BPM.

In yet another embodiment, provided herein is a method of treating, preventing, or ameliorating one or more symptoms of stroke in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the stroke is hemorrhagic stroke. In another embodiment, the stroke is ischemic stroke. In yet another embodiment, the stroke is stroke associated with abnormal cardiac output. In still another embodiment, the stroke is stroke associated with bradycardia.

In yet another embodiment, provided herein is a method of treating, preventing, or ameliorating one or more symptoms of cerebral vascular thrombosis in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

Without being bound by any theory, a subject normally has slower heart beats when sleeping at night. Consequently, a bradycardia subject is prone to thrombosis during sleeping because of the slower heart beats.

In yet another embodiment, provided herein is a method of treating, preventing, or ameliorating abnormal heart rhythm (e.g., heart rate ≤50 beats per minutes (BPM)) in a subject after a cardiac surgery, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the subject after being treated with a pharmaceutical composition or method provided herein has a normal heart rhythm. In one embodiment, the subject after being treated with a pharmaceutical composition or method provided herein has a resting pulse rate (RPR) ranging from about 35 to about 130, from about 40 to about 120, from about 45 to 110, from about 50 to about 100, or from about 60 to about 100. In another embodiment, the subject after being treated with a pharmaceutical composition or method provided herein has a RPR of about 40, about 42, about 44, about 46, about 48, about 50, about 52, about 54, about 56, about 58, about 60, about 62, about 64, about 66, about 68, or about 70. In yet another embodiment, the subject after being treated with a pharmaceutical composition or method provided herein has a RPR of about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, or about 75.

In yet another embodiment, provided herein is a method of increasing heart rate in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, provided herein is a method of increasing heart rate without a substantial change in oxygen consumption in a subject, comprising administering to the subject: (i) a phosphodiesterase inhibitor or an adenosine receptor antagonist; and (ii) a calcium channel blocker.

In another embodiment, provided herein is a method of increasing heart rate without a substantial change in oxygen consumption in a subject, comprising administering to the subject: (i) a xanthine compound or an isotopic variant thereof, or a pharmaceutically acceptable salt, hydrate, or solvate thereof, and (ii) a dihydropyridine or an isotopic variant thereof; or a pharmaceutically acceptable salt, hydrate, or solvate thereof.

In yet another embodiment, provided herein is a method of increasing heart rate without a substantial change in oxygen consumption in a subject, comprising administering to the subject: (i) theophylline or an isotopic variant thereof; or a pharmaceutically acceptable salt, hydrate, or solvate thereof; and (ii) nifedipine or an isotopic variant thereof, or a pharmaceutically acceptable salt, hydrate, or solvate thereof.

In still another embodiment, provided herein is a method of increasing heart rate without a substantial change in oxygen consumption in a subject, comprising administering to the subject: (i) aminophylline or theophylline; and (ii) nifedipine.

Without being bound by any theory, a phosphodiesterase inhibitor or adenosine receptor antagonist can be paired together with a calcium channel blocker to minimize undesired side effect(s). For example, theophylline is known to have the side effect of causing an increase in oxygen consumption, whereas nifedipine is known to have the side effect of causing a decrease in oxygen consumption. Both are also known to have the side effect of causing an increase in heart rate. Thus, theophylline can be paired together with nifedipine to cause an increase in heart rate without a substantial change in oxygen consumption.

In one embodiment, provided herein is a method of increasing heart rate without a substantial change in blood pressure in a subject, comprising administering to the subject: (i) a histamine $H_1$-receptor agonist, a histamine $H_2$-receptor agonist, or a histamine $H_3$-receptor antagonist; and (ii) a $\beta_2$-adrenoreceptor agonist; wherein the subject has no substantial change in blood pressure.

In another embodiment, provided herein is a method of increasing heart rate without a substantial change in blood pressure in a subject, comprising administering to the subject: (i) betahistine or an isotopic variant thereof; or a pharmaceutically acceptable salt, hydrate, or solvate thereof; and (ii) albuterol, or an enantiomer, a mixture of enantiomers, or an isotopic variant thereof, or a pharmaceutically acceptable salt, hydrate, or solvate thereof.

In yet another embodiment, provided herein is a method of increasing heart rate without a substantial change in blood pressure in a subject, comprising administering to the subject: (i) betahistine hydrochloride; and (ii) albuterol hydrochloride or levalbuterol hydrochloride.

Without being bound by any theory, a histamine $H_1$-receptor agonist, a histamine $H_2$-receptor agonist, or a histamine $H_3$-receptor antagonist can be paired together with a $\beta_2$-adrenoreceptor agonist to minimize undesired side effect(s). For example, betahistine is known to have the side effect of causing an increase in blood pressure, whereas albuterol and levalbuterol are each known to have the side effect of causing a decrease in blood pressure. Betahistine, albuterol, and levalbuterol are also known to have the side effect of causing an increase in heart rate. Thus, betahistine can be paired together with albuterol or levalbuterol to cause an increase in heart rate without a substantial change in blood pressure.

In one embodiment, the subject after treated with a pharmaceutical composition or method provided herein has an increase in a RPR ranging from about 2 to about 25, from about 5 to about 20, from about 5 to about 15, or from about 5 to about 10. In another embodiment, the subject after treated with a pharmaceutical composition or method provided herein has an increase in a RPR of about 5, about 6, about 7, about 8, about 9, or about 10.

In yet another embodiment, provided herein is a method of increasing cardiac output in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the subject after being treated with a pharmaceutical composition or method provided herein has an increase in cardiac output at rest ranging from about 200 to about 2,000, from about 100 to about 1,000, or from about 100 to about 500 mL/min.

In yet another embodiment, provided herein is a method of increasing cerebral blood flow in a subject, comprising administering to the subject two or more compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, the subject after being treated with a pharmaceutical composition or method provided herein has an increase in cerebral blood flow ranging from about 200 to about 750, from about 250 to about 600, or from about 300 to about 500 mL/min.

In one embodiment, a method provided herein comprises administering to the subject two compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a phosphodiesterase inhibitor or an adenosine receptor antagonist; and (ii) a calcium channel blocker. In another embodiment, a method provided herein comprises administering to the subject: (i) a phosphodiesterase inhibitor or an adenosine receptor antagonist; and (ii) a histamine $H_1$-receptor agonist, a histamine $H_2$-receptor agonist, or a histamine $H_3$-receptor antagonist. In yet another embodiment, a method provided herein comprises administering to the subject: (i) a phosphodiesterase inhibitor or an adenosine receptor antagonist; and (ii) a $\beta_2$-adrenoreceptor agonist. In yet another embodiment, a method provided herein comprises administering to the subject: (i) a calcium channel blocker; and (ii) a histamine $H_1$-receptor agonist, a histamine $H_2$-receptor agonist, or a histamine $H_3$-receptor antagonist. In yet another embodiment, a method provided herein comprises administering to the subject: (i) a calcium channel blocker and (ii) a $\beta_2$-adrenoreceptor agonist. In still another embodiment, a method provided herein comprises administering to the subject: (i) a histamine $H_1$-receptor agonist, a histamine $H_2$-receptor agonist, or a histamine $H_3$-receptor antagonist; and (ii) a $\beta_2$-adrenoreceptor agonist.

In another embodiment, a method provided herein comprises administering to the subject three compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a phosphodiesterase inhibitor or an adenosine receptor antagonist; (ii) a calcium channel blocker; and (iii) a histamine $H_1$-receptor agonist, a histamine $H_2$-receptor agonist, or a histamine $H_3$-receptor antagonist. In another embodiment, a method provided herein comprises administering to the subject: (i) a phosphodiesterase inhibitor or an adenosine receptor antagonist; (ii) a calcium channel blocker; and (iii) a $\beta_2$-adrenoreceptor agonist. In yet another embodiment, a method provided herein comprises administering to the subject: (i) a phosphodiesterase inhibitor or an adenosine receptor antagonist; (ii) a histamine $H_1$-receptor agonist, a histamine $H_2$-receptor agonist, or a histamine $H_3$-receptor antagonist; and (iii) a $\beta_2$-adrenoreceptor agonist.

In yet another embodiment, a method provided herein comprises administering to the subject four compounds, wherein each compound is independently a phosphodiesterase inhibitor, an adenosine receptor antagonist, a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a phosphodiesterase inhibitor or an adenosine receptor antagonist; (ii) a calcium channel blocker; (iii) a histamine $H_1$-receptor agonist, a histamine $H_2$-receptor agonist, or a histamine $H_3$-receptor antagonist; and (iv) $\beta_2$-adrenoreceptor agonist.

In certain embodiments, the weight ratio of (i) the phosphodiesterase inhibitor or adenosine receptor antagonist to (ii) the calcium channel blocker in a method provided herein is ranging from about 1 to about 180, from about 2 to about 100, from about 2 to about 50, or from about 2 to about 20. In certain embodiments, the weight ratio of (i) the phosphodiesterase inhibitor or adenosine receptor antagonist to (ii) the calcium channel blocker in a method provided herein is about 2, about 3, about 4, about 5, about 6, about 7, about 8, about 9, about 10, about 11, about 12, about 13, about 14, about 15, about 16, about 17, about 18, about 19, or about 20.

In certain embodiments, the weight ratio of (i) the phosphodiesterase inhibitor or adenosine receptor antagonist to (ii) the histamine $H_1$-receptor agonist, histamine $H_2$-receptor agonist, or histamine $H_3$-receptor antagonist in a method provided herein is ranging from about 2 to about 200, from about 4 to about 100, from about 5 to about 50, or from about 10 to about 30. In certain embodiments, the weight ratio of (i) the phosphodiesterase inhibitor or adenosine receptor antagonist to (ii) the histamine $H_1$-receptor agonist, histamine $H_2$-receptor agonist, or histamine $H_3$-receptor antagonist in a method provided herein is about 10, about 12, about 14, about 16, about 18, about 20, about 22, about 24, about 26, about 28, or about 30.

In certain embodiments, the weight ratio of (i) the phosphodiesterase inhibitor or adenosine receptor antagonist to (ii) the $\beta_2$-adrenoreceptor agonist in a method provided herein is ranging from about 1 to about 1,000, from about 10 to about 500, from about 20 to about 400, or from about 40 to about 300. In certain embodiments, the weight ratio of (i) the phosphodiesterase inhibitor or adenosine receptor antagonist to (ii) the $\beta_2$-adrenoreceptor agonist in a method provided herein is about 40, about 60, about 80, about 100, about 120, about 140, about 160, about 180, about 200, about 220, about 240, about 260, about 280, or about 300.

In certain embodiments, the weight ratio of (i) the calcium channel blocker to (ii) the histamine $H_1$-receptor agonist, histamine $H_2$-receptor agonist, or histamine $H_3$-receptor antagonist in a method provided herein is ranging from about 1 to about 50, from about 1 to about 40, from about 1 to about 20, or from about 1 to about 10. In certain embodiments, the weight ratio of (i) the calcium channel blocker to (ii) the histamine $H_1$-receptor agonist, histamine $H_2$-receptor agonist, or histamine $H_3$-receptor antagonist in a method provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, the weight ratio of (i) the calcium channel blocker to (ii) the $\beta_2$-adrenoreceptor agonist in a method provided herein is ranging from about 1 to about 100, from about 5 to about 50, or from about 5 to about 30. In certain embodiments, the weight ratio of (i) the calcium channel blocker to (ii) the $\beta_2$-adrenoreceptor agonist in a method provided herein is about 5, about 6, about 8, about 10, about 12, about 14, about 16, about 18, about 20, about 22, about 24, about 26, about 28, or about 20.

In certain embodiments, the weight ratio of (i) the histamine $H_1$-receptor agonist, histamine $H_2$-receptor agonist, or histamine $H_3$-receptor antagonist to (ii) the $\beta_2$-adrenoreceptor agonist in a method provided herein is ranging from about 1 to about 100, from about 1 to about 50, from about 1 to about 30, or from about 1 to about 20. In certain embodiments, the weight ratio of (i) the histamine $H_1$-receptor agonist, histamine $H_2$-receptor agonist, or histamine $H_3$-receptor antagonist to (ii) the $\beta_2$-adrenoreceptor agonist in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a method provided herein comprises administering to the subject a phosphodiesterase inhibitor or an adenosine receptor antagonist in a subtherapeutic effective amount. In certain embodiments, a method provided herein comprises administering to the subject a phosphodiesterase inhibitor or an adenosine receptor antagonist in the amount ranging from about 1 to about 1,200, from about 5 to about 1,000, from about 10 to about 800, or from about 20 to about 600 mg per day. In certain embodiments, a method provided herein comprises administering to the subject a phosphodiesterase inhibitor or an adenosine receptor antagonist in the amount ranging from about 1 to about 1,200 mg per day. In certain embodiments, a method provided herein comprises administering to the subject a phosphodiesterase inhibitor or an adenosine receptor antagonist in the amount ranging from about 5 to about 1,000 mg per day. In certain embodiments, a method provided herein comprises administering to the subject a phosphodiesterase inhibitor or an adenosine receptor antagonist in the amount ranging from about 10 to about 800 mg per day. In certain embodiments, a method provided herein comprises administering to the subject a phosphodiesterase inhibitor or an adenosine receptor antagonist in the amount ranging from about 20 to about 600 mg per day. In certain embodiments, a method provided herein comprises administering to the subject a phosphodiesterase inhibitor or an adenosine receptor antagonist in the amount of about 20, about 50, about 75, about 100, about 125, about 150, about 175, about 200, about 225, about 250, about 275, about 300, about 325, about 350, about 375, about 400, about 425, about 450, about 475, about 500, about 525, about 550, about 575, or about 600 mg per day.

In certain embodiments, a method provided herein comprises administering to the subject a calcium channel blocker in a subtherapeutic effective amount. In certain embodiments, a method provided herein comprises administering to the subject a calcium channel blocker in the amount ranging from about 1 to about 200, from about 1 to about 100, or from about 2 to about 60 mg per day. In certain embodiments, a method provided herein comprises administering to the subject a calcium channel blocker in the amount ranging from about 1 to about 200 mg per day. In certain embodiments, a method provided herein comprises administering to the subject a calcium channel blocker in the amount ranging from about 1 to about 100 mg per day. In certain embodiments, a method provided herein comprises administering to the subject a calcium channel blocker in the amount ranging from about 2 to about 60 mg per day. In certain embodiments, a method provided herein comprises administering to the subject a calcium channel blocker in the amount of about 2, about 5, about 10, about 15, about 20, about 25, about 30, about 35, about 40, about 45, about 50, about 55, or about 60 mg per day.

In certain embodiments, a method provided herein comprises administering to the subject a histamine $H_1$-receptor agonist, a histamine $H_2$-receptor agonist, or a histamine $H_3$-receptor antagonist in a subtherapeutic effective amount. In certain embodiments, a method provided herein comprises administering to the subject a histamine $H_1$-receptor agonist, a histamine $H_2$-receptor agonist, or a histamine $H_3$-receptor antagonist in the amount ranging from about 0.1 to about 100, from about 0.5 to about 50, from about 1 to about 30 mg per day. In certain embodiments, a method provided herein comprises administering to the subject a histamine $H_1$-receptor agonist, a histamine $H_2$-receptor agonist, or a histamine $H_3$-receptor antagonist in the amount ranging from about 0.1 to about 100 mg per day. In certain embodiments, a method provided herein comprises administering to the subject a histamine $H_1$-receptor agonist, a histamine $H_2$-receptor agonist, or a histamine $H_3$-receptor antagonist in the amount ranging from about 0.5 to about 50 mg per day. In certain embodiments, a method provided herein comprises administering to the subject a histamine $H_1$-receptor agonist, a histamine $H_2$-receptor agonist, or a histamine $H_3$-receptor antagonist in the amount ranging from about 1 to about 30 mg per day. In certain embodiments, a method provided herein comprises administering to the subject a histamine $H_1$-receptor agonist, a histamine $H_2$-receptor agonist, or a histamine $H_3$-receptor antagonist in the amount of about 1, about 2, about 4, about 6, about 8, about 10, about 12, about 14, about 16, about 18, about 20, about 22, about 24, about 26, about 28 or about 30 mg per day.

In certain embodiments, a method provided herein comprises administering to the subject a $\beta_2$-adrenoreceptor agonist in a subtherapeutic effective amount. In certain embodiments, a method provided herein comprises administering to the subject a $\beta_2$-adrenoreceptor agonist in the amount ranging from about 0.1 to about 50, from about 0.1 to about 20, or from about 0.1 to about 10 mg per day. In certain embodiments, a method provided herein comprises administering to the subject a $\beta_2$-adrenoreceptor agonist in the amount ranging from about 0.1 to about 50 mg per day. In certain embodiments, a method provided herein comprises administering to the subject a $\beta_2$-adrenoreceptor agonist in the amount ranging from about 0.1 to about 20 mg per day. In certain embodiments, a method provided herein comprises administering to the subject a $\beta_2$-adrenoreceptor agonist in the amount ranging from about 0.1 to about 10 mg per day. In certain embodiments, a method provided herein comprises administering to the subject a $\beta_2$-adrenoreceptor agonist in the amount of about 0.1, about 0.2, about 0.5, about 1, about 1.5, about 2, about 2.5, about 3, about 3.5, about 4, about 4.5, about 5, about 6, about 7, about 8, about 9, or about 10 mg per day.

In certain embodiments, the phosphodiesterase inhibitor or adenosine receptor antagonist in a method provided herein is administered once daily (QD) or divided into multiple daily doses such as twice daily (BID), three times daily (TID), four times daily (QID), five times daily, or six times daily. In certain embodiments, the phosphodiesterase inhibitor or adenosine receptor antagonist in a method provided herein is administered QD. In certain embodiments, the phosphodiesterase inhibitor or adenosine receptor antagonist in a method provided herein is administered BID. In certain embodiments, the phosphodiesterase inhibitor or adenosine receptor antagonist in a method provided herein is administered TID. In certain embodiments, the phosphodiesterase inhibitor or adenosine receptor antagonist in a method provided herein is administered QID.

In certain embodiments, the calcium channel blocker in a method provided herein is administered once daily (QD) or divided into multiple daily doses such as twice daily (BID), three times daily (TID), four times daily (QID), five times daily, or six times daily. In certain embodiments, the calcium channel blocker in a method provided herein is administered QD. In certain embodiments, the calcium channel blocker in a method provided herein is administered BID. In certain embodiments, the calcium channel blocker in a method provided herein is administered TID. In certain embodiments, the calcium channel blocker in a method provided herein is administered QID.

In certain embodiments, the histamine $H_1$-receptor agonist, histamine $H_2$-receptor agonist, or histamine $H_3$-receptor antagonist in a method provided herein is administered once daily (QD) or divided into multiple daily doses such as twice daily (BID), three times daily (TID), four times daily (QID), five times daily, or six times daily. In certain embodiments, the histamine $H_1$-receptor agonist, histamine $H_2$-receptor agonist, or histamine $H_3$-receptor antagonist in a method provided herein is administered QD. In certain embodiments, the histamine $H_1$-receptor agonist, histamine $H_2$-receptor agonist, or histamine $H_3$-receptor antagonist in a method provided herein is administered BID. In certain embodiments, the histamine $H_1$-receptor agonist, histamine $H_2$-receptor agonist, or histamine $H_3$-receptor antagonist in a method provided herein is administered TID. In certain embodiments, the histamine $H_1$-receptor agonist, histamine $H_2$-receptor agonist, or histamine $H_3$-receptor antagonist in a method provided herein is administered QID.

In certain embodiments, the $\beta_2$-adrenergic receptor agonist in a method provided herein is administered once daily (QD), or divided into multiple daily doses such as twice daily (BID), three times daily (TID), four times daily (QID), five times daily, or six times daily. In certain embodiments, the $\beta_2$-adrenergic receptor agonist in a method provided herein is administered QD. In certain embodiments, the $\beta_2$-adrenergic receptor agonist in a method provided herein is administered BID. In certain embodiments, the $\beta_2$-adrenergic receptor agonist in a method provided herein is administered TID. In certain embodiments, the $\beta_2$-adrenergic receptor agonist in a method provided herein is administered QID.

In certain embodiments, the phosphodiesterase inhibitor, adenosine receptor antagonist, calcium channel blocker, histamine $H_1$-receptor agonist, histamine $H_2$-receptor agonist, or histamine $H_3$-receptor antagonist, and $\beta_2$-adrenoreceptor agonist in a method provided herein are administered concurrently or sequentially in any order. In certain embodiments, the phosphodiesterase inhibitor and/or adenosine receptor antagonist in a method provided herein is administered currently with the calcium channel blocker. In certain embodiments, the phosphodiesterase inhibitor and/or adenosine receptor antagonist in a method provided herein is administered currently with the calcium channel blocker in a single pharmaceutical composition provided herein. In certain embodiments, the histamine $H_1$-receptor agonist, histamine $H_2$-receptor agonist, or histamine $H_3$-receptor antagonist in a method provided herein is administered concurrently with the $\beta_2$-adrenoreceptor agonist. In certain embodiments, the histamine $H_1$-receptor agonist, histamine $H_2$-receptor agonist, or histamine $H_3$-receptor antagonist in a method provided herein is administered concurrently with the $\beta_2$-adrenoreceptor agonist in a single pharmaceutical composition provided herein. In certain embodiments, the phosphodiesterase inhibitor, adenosine receptor antagonist, calcium channel blocker, histamine $H_1$-receptor agonist, histamine $H_2$-receptor agonist, or histamine $H_3$-receptor antagonist, and $\beta_2$-adrenoreceptor agonist in a method provided herein are administered concurrently. In certain embodiments, the phosphodiesterase inhibitor, adenosine receptor antagonist, calcium channel blocker, histamine $H_1$-receptor agonist, histamine $H_2$-receptor agonist, or histamine $H_3$-receptor antagonist, and $\beta_2$-adrenoreceptor agonist in a method provided herein are administered in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof, and (ii) one or more compounds, wherein each compound is independently a calcium channel blocker, a histamine $H_1$-receptor agonist, a histamine $H_2$-receptor agonist, a histamine $H_3$-receptor antagonist, or a $\beta_2$-adrenoreceptor agonist.

In another embodiment, a method provided herein comprises administering to the subject: (i) a xanthine compound or an isotopic variant thereof; or a pharmaceutically acceptable salt, hydrate, or solvate thereof; and (ii) a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a xanthine compound or an isotopic variant thereof; or a pharmaceutically acceptable salt, hydrate, or solvate thereof; and (ii) a calcium channel blocker. In another embodiment, a method provided herein comprises administering to the subject: (i) a xanthine compound or an isotopic variant thereof; or a pharmaceutically acceptable salt, hydrate, or solvate thereof; and (ii) a histamine $H_1$-receptor agonist, a histamine $H_2$-receptor agonist, or histamine $H_3$-receptor antagonist. In yet another embodiment, a method provided herein comprises administering to the subject: (i) a xanthine compound or an isotopic variant thereof; or a pharmaceutically acceptable salt, hydrate, or solvate thereof; and (ii) a $\beta_2$-adrenoreceptor agonist.

In yet another embodiment, a method provided herein comprises administering to the subject: (i) a xanthine compound or an isotopic variant thereof; or a pharmaceutically acceptable salt, hydrate, or solvate thereof; and (ii) two compounds, wherein each compound is independently a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a xanthine compound or an isotopic variant thereof; or a pharmaceutically acceptable salt, hydrate, or solvate thereof; (ii) a calcium channel blocker; and (iii) a histamine $H_1$-receptor agonist, a histamine $H_2$-receptor agonist, or histamine $H_3$-receptor antagonist. In another embodiment, a method provided herein comprises administering to the subject: (i) a xanthine compound or an isotopic variant thereof; or a pharmaceutically acceptable salt, hydrate, or solvate thereof; (ii) a calcium channel blocker; and (iii) a $\beta_2$-adrenoreceptor agonist. In yet another embodiment, a method provided herein comprises administering to the subject: (i) a xanthine compound or an isotopic variant thereof; or a pharmaceutically acceptable salt, hydrate, or solvate thereof; (ii) a histamine $H_1$-receptor agonist, a histamine $H_2$-receptor agonist, or a histamine $H_3$-receptor antagonist; and (iii) a $\beta_2$-adrenoreceptor agonist.

In still another embodiment, a method provided herein comprises administering to the subject: (i) a xanthine compound or an isotopic variant thereof; or a pharmaceutically acceptable salt, hydrate, or solvate thereof; and (ii) three compounds, wherein each compound is independently a calcium channel blocker, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a xanthine compound or an isotopic variant thereof; or a pharmaceutically acceptable salt, hydrate, or solvate thereof; (ii) a calcium channel blocker; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the weight ratio of the xanthine compound to the calcium channel blocker in a method provided herein is ranging from about 1 to about 180, from about 2 to about 100, from about 2 to about 50, or from about 2 to about 20. In certain embodiments, the weight ratio of the xanthine compound to the calcium channel blocker in a method provided herein is ranging from about 1 to about 180. In certain embodiments, the weight ratio of the xanthine compound to the calcium channel blocker in a method provided herein is ranging from about 2 to about 100. In certain embodiments, the weight ratio of the xanthine compound to the calcium channel blocker in a method provided herein is ranging from about 2 to about 50. In certain embodiments, the weight ratio of the xanthine compound to the calcium channel blocker in a method provided herein is ranging from about 2 to about 20. In certain embodiments, the weight ratio of the xanthine compound to the calcium channel blocker in a method provided herein is about 2, about 4, about 6, about 8, about 10, about 12, about 14, about 16, about 18, or about 20.

In certain embodiments, the weight ratio of (i) the xanthine compound to (ii) the histamine $H_1$-receptor agonist, histamine $H_2$-receptor agonist, or histamine $H_3$-receptor antagonist in a method provided herein is ranging from about 2 to about 200, from about 4 to about 100, from about 5 to about 50, or from about 10 to about 30. In certain embodiments, the weight ratio of (i) the xanthine compound to (ii) the histamine $H_1$-receptor agonist, histamine $H_2$-receptor agonist, or histamine $H_3$-receptor antagonist in a method provided herein is about 10, about 12, about 14, about 16, about 18, about 20, about 22, about 24, about 26, about 28, or about 30.

In certain embodiments, the weight ratio of the xanthine compound to the $\beta_2$-adrenoreceptor agonist in a method provided herein is ranging from about 1 to about 1,000, from about 10 to about 500, from about 20 to about 400, or from about 40 to about 300. In certain embodiments, the weight ratio of the xanthine compound to the $\beta_2$-adrenoreceptor agonist in a method provided herein is about 40, about 60, about 80, about 100, about 120, about 140, about 160, about 180, about 200, about 220, about 240, about 260, about 280, or about 300.

In certain embodiments, a method provided herein comprises administering to the subject a xanthine compound or an isotopic variant thereof; or a pharmaceutically acceptable salt, hydrate, or solvate thereof in a subtherapeutic effective amount. In certain embodiments, a method provided herein comprises administering to the subject a xanthine compound in the amount ranging from about 1 to about 1,200, from about 5 to about 1,000, from about 10 to about 800, or from about 20 to about 600 mg per day. In certain embodiments, a method provided herein comprises administering to the subject a xanthine compound in the amount ranging from about 1 to about 1,200 mg per day. In certain embodiments, a method provided herein comprises administering to the subject a xanthine compound in the amount ranging from about 5 to about 1,000 mg per day. In certain embodiments, a method provided herein comprises administering to the subject a xanthine compound in the amount ranging from about 10 to about 800 mg per day. In certain embodiments, a method provided herein comprises administering to the subject a xanthine compound in the amount ranging from about 20 to about 600 mg per day. In certain embodiments, a method provided herein comprises administering to the subject a xanthine compound in the amount of about 20, about 50, about 75, about 100, about 125, about 150, about 175, about 200, about 225, about 250, about 275, about 300, about 325, about 350, about 375, about 400, about 425, about 450, about 475, about 500, about 525, about 550, about 575, or about 600 mg per day.

In certain embodiments, the xanthine compound in a method provided herein is administered once daily (QD), or divided into multiple daily doses such as twice daily (BID), three times daily (TID), four times daily (QID), five times daily, or six times daily. In certain embodiments, the xanthine compound in a method provided herein is administered QD. In certain embodiments, the xanthine compound in a method provided herein is administered BID. In certain embodiments, the xanthine compound in a method provided herein is administered TID. In certain embodiments, the xanthine compound in a method provided herein is administered QID.

In certain embodiments, the xanthine compound in a method provided herein is administered concurrently or sequentially in any order with the calcium channel blocker, histamine $H_1$-receptor agonist, histamine $H_2$-receptor agonist, histamine $H_3$-receptor antagonist, and $\beta_2$-adrenoreceptor agonist. In certain embodiments, the xanthine compound in a method provided herein is administered concurrently with the calcium channel blocker. In certain embodiments, the xanthine compound in a method provided herein is administered concurrently with the calcium channel blocker in a single pharmaceutical composition provided herein. In certain embodiments, the xanthine compound in a method provided herein is administered concurrently with the calcium channel blocker, histamine $H_1$-receptor agonist, histamine $H_2$-receptor agonist, histamine $H_3$-receptor antagonist, and $\beta_2$-adrenoreceptor agonist. In certain embodiments, the xanthine compound in a method provided herein is administered concurrently with the calcium channel blocker, histamine $H_1$-receptor agonist, histamine $H_2$-receptor agonist, histamine $H_3$-receptor antagonist, and $\beta_2$-adrenoreceptor agonist in a single pharmaceutical composition provided herein.

In one embodiment, a method provided herein comprises administering to the subject: (i) a dihydropyridine or an isotopic variant thereof; or a pharmaceutically acceptable salt, hydrate, or solvate thereof; and (ii) one or more compounds, wherein each compound is independently a PDE inhibitor, an adenosine receptor antagonist, a histamine $H_1$-receptor agonist, a histamine $H_2$-receptor agonist, a histamine $H_3$-receptor antagonist or a $\beta_2$-adrenoreceptor agonist.

In another embodiment, a method provided herein comprises administering to the subject: (i) a dihydropyridine or an isotopic variant thereof; or a pharmaceutically acceptable salt, hydrate, or solvate thereof; and (ii) a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a dihydropyridine or an isotopic variant thereof; or a pharmaceutically acceptable salt, hydrate, or solvate thereof; and (ii) a PDE inhibitor or an adenosine receptor antagonist. In another embodiment, a method provided herein comprises administering to the subject: (i) a dihydropyridine or an isotopic variant thereof; or a pharmaceutically acceptable salt, hydrate, or solvate thereof; and (ii) a histamine $H_1$-receptor agonist, a histamine $H_2$-receptor agonist, or a histamine $H_3$-receptor antagonist. In yet another embodiment, a method provided herein comprises administering to the subject: (i) a dihydropyridine or an isotopic variant thereof; or a pharmaceutically acceptable salt, hydrate, or solvate thereof; and (ii) a $\beta_2$-adrenoreceptor agonist.

In yet another embodiment, a method provided herein comprises administering to the subject: (i) a dihydropyridine or an isotopic variant thereof; or a pharmaceutically acceptable salt, hydrate, or solvate thereof; and (ii) two compounds, wherein each compound is independently a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a dihydropyridine or an isotopic variant thereof; or a pharmaceutically acceptable salt, hydrate, or solvate thereof; (ii) a PDE inhibitor or an adenosine receptor antagonist; and (iii) a histamine $H_1$-receptor agonist, a histamine $H_2$-receptor agonist, or a histamine $H_3$-receptor antagonist. In another embodiment, a method provided herein comprises administering to the subject: (i) a dihydropyridine or an isotopic variant thereof; or a pharmaceutically acceptable salt, hydrate, or solvate thereof; (ii) a PDE inhibitor or an adenosine receptor antagonist; and (iii) a $\beta_2$-adrenoreceptor agonist. In yet another embodiment, a method provided herein comprises administering to the subject: (i) a dihydropyridine or an isotopic variant thereof; or a pharmaceutically acceptable salt, hydrate, or solvate thereof; (ii) a histamine $H_1$-receptor agonist, a histamine $H_2$-receptor agonist, or a histamine $H_3$-receptor antagonist; and (iii) a $\beta_2$-adrenoreceptor agonist.

In yet another embodiment, a method provided herein comprises administering to the subject: (i) a dihydropyridine or an isotopic variant thereof; or a pharmaceutically acceptable salt, hydrate, or solvate thereof; and (ii) three compounds, wherein each compound is independently a PDE inhibitor, an adenosine receptor antagonist, a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a dihydropyridine or an isotopic variant thereof; or a pharmaceutically acceptable salt, hydrate, or solvate thereof; (ii) a PDE inhibitor or an adenosine receptor antagonist; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the weight ratio of (i) the phosphodiesterase inhibitor or adenosine receptor antagonist to (ii) the dihydropyridine in a method provided herein is ranging from about 1 to about 180, from about 2 to about 100, from about 2 to about 50, or from about 2 to about 20. In certain embodiments, the weight ratio of (i) the phosphodiesterase inhibitor or adenosine receptor antagonist to (ii) the dihydropyridine in a method provided herein is about 2, about 4, about 6, about 8, about 10, about 12, about 14, about 16, about 18, or about 20.

In certain embodiments, the weight ratio of (i) the dihydropyridine to (ii) the histamine $H_1$-receptor agonist, histamine $H_2$-receptor agonist, or histamine $H_3$-receptor antagonist in a method provided herein is ranging from about 1 to about 50, from about 1 to about 40, from about 1 to about 20, or from about 1 to about 10. In certain embodiments, the weight ratio of (i) the dihydropyridine to (ii) the histamine $H_1$-receptor agonist, histamine $H_2$-receptor agonist, or histamine $H_3$-receptor antagonist in a method provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, the weight ratio of the dihydropyridine to the $\beta_2$-adrenoreceptor agonist in a method provided herein is ranging from about 1 to about 100, from about 1 to about 50, or from about 5 to about 30. In certain embodiments, the weight ratio of the dihydropyridine to the $\beta_2$-adrenoreceptor agonist in a method provided herein is about 5, about 10, about 11, about 12, about 13, about 14, about 15, about 16, about 17, about 18, about 19, about 20, about 21, about 22, about 23, about 24, about 25, about 26, about 27, about 28, about 29, or about 30.

In certain embodiments, a method provided herein comprises administering to the subject a dihydropyridine or an isotopic variant thereof; or a pharmaceutically acceptable salt, hydrate, or solvate thereof in a subtherapeutically effective amount. In certain embodiments, a method provided herein comprises administering to the subject a dihydropyridine in a subtherapeutic effective amount. In certain embodiments, a method provided herein comprises administering to the subject a dihydropyridine in the amount ranging from about 0.5 to about 200, from about 1 to about 100, or from about 2 to about 60 mg per day. In certain embodiments, a method provided herein comprises administering to the subject a dihydropyridine in the amount ranging from about 0.5 to about 200 mg per day. In certain embodiments, a method provided herein comprises administering to the subject a dihydropyridine in the amount ranging from about 1 to about 100 mg per day. In certain embodiments, a method provided herein comprises administering to the subject a dihydropyridine in the amount ranging from about 2 to about 50 mg per day. In certain embodiments, a method provided herein comprises administering to the subject a dihydropyridine in the amount of about 2, about 5, about 10, about 15, about 20, about 25, about 30, about 35, about 40, about 45, about 50, about 55, or about 60 mg per day.

In certain embodiments, the dihydropyridine in a method provided herein is administered once daily (QD) or divided into multiple daily doses such as twice daily (BID), three times daily (TID), four times daily (QID), five times daily, or six times daily. In certain embodiments, the dihydropyridine in a method provided herein is administered QD. In certain embodiments, the dihydropyridine in a method provided herein is administered BID. In certain embodiments, the dihydropyridine in a method provided herein is administered TID. In certain embodiments, the dihydropyridine in a method provided herein is administered QID.

In certain embodiments, the dihydropyridine in a method provided herein is administered concurrently or sequentially in any order with the phosphodiesterase inhibitor, adenosine receptor antagonist, histamine $H_1$-receptor agonist, histamine $H_2$-receptor agonist, a histamine $H_3$-receptor antagonist, or $\beta_2$-adrenoreceptor agonist. In certain embodiments, the dihydropyridine in a method provided herein is administered concurrently with the phosphodiesterase inhibitor or adenosine receptor antagonist. In certain embodiments, the dihydropyridine in a method provided herein is administered concurrently with the phosphodiesterase inhibitor or adenosine receptor antagonist in a single pharmaceutical composition provided herein. In certain embodiments, the dihydropyridine in a method provided herein is administered concurrently with the phosphodiesterase inhibitor, adenosine receptor antagonist, histamine $H_1$-receptor agonist, histamine $H_2$-receptor agonist, a histamine $H_3$-receptor antagonist, or $\beta_2$-adrenoreceptor agonist. In certain embodiments, the dihydropyridine in a method provided herein is administered concurrently with the phosphodiesterase inhibitor, adenosine receptor antagonist, histamine $H_1$-receptor agonist, histamine $H_2$-receptor agonist, a histamine $H_3$-receptor antagonist or $\beta_2$-adrenoreceptor agonist in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof, (ii) a dihydropyridine or an isotopic variant thereof, or a pharmaceutically acceptable salt, hydrate, or solvate thereof; and (iii) optionally one or more compounds, wherein each compound is independently a histamine $H_1$-receptor agonist, a histamine $H_2$-receptor agonist, a histamine $H_3$-receptor antagonist, or a $\beta_2$-adrenoreceptor agonist.

In another embodiment, a method provided herein comprises administering to the subject: (i) a xanthine compound or an isotopic variant thereof, or a pharmaceutically acceptable salt, hydrate, or solvate thereof; and (ii) a dihydropyridine or an isotopic variant thereof, or a pharmaceutically acceptable salt, hydrate, or solvate thereof.

In yet another embodiment, a method provided herein comprises administering to the subject: (i) a xanthine compound or an isotopic variant thereof, or a pharmaceutically acceptable salt, hydrate, or solvate thereof; (ii) a dihydropyridine or an isotopic variant thereof, or a pharmaceutically acceptable salt, hydrate, or solvate thereof; and (iii) a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a xanthine compound or an isotopic variant thereof, or a pharmaceutically acceptable salt, hydrate, or solvate thereof; (ii) a dihydropyridine or an isotopic variant thereof, or a pharmaceutically acceptable salt, hydrate, or solvate thereof; and (iii) a histamine $H_1$-receptor agonist, a histamine $H_2$-receptor agonist, or a histamine $H_3$-receptor antagonist. In another embodiment, a method provided herein comprises administering to the subject: (i) a xanthine compound or an isotopic variant thereof, or a pharmaceutically acceptable salt, hydrate, or solvate thereof; (ii) a dihydropyridine or an isotopic variant thereof; or a pharmaceutically acceptable salt, hydrate, or solvate thereof; and (iii) a $\beta_2$-adrenoreceptor agonist.

In still another embodiment, a method provided herein comprises administering to the subject: (i) a xanthine compound or an isotopic variant thereof; or a pharmaceutically acceptable salt, hydrate, or solvate thereof; (ii) a dihydropyridine or an isotopic variant thereof; or a pharmaceutically acceptable salt, hydrate, or solvate thereof; and (iii) two compounds, wherein each compound is independently a histamine $H_1$-receptor agonist, a histamine $H_2$-receptor agonist, a histamine $H_3$-receptor antagonist, or a $\beta_2$-adrenoreceptor agonist.

In one embodiment, a method provided herein comprises administering to the subject: (i) a xanthine compound or an isotopic variant thereof; or a pharmaceutically acceptable salt, hydrate, or solvate thereof; (ii) a dihydropyridine or an isotopic variant thereof; or a pharmaceutically acceptable salt, hydrate, or solvate thereof; (iii) a histamine $H_1$-receptor agonist, a histamine $H_2$-receptor agonist, or a histamine $H_3$-receptor antagonist; and (iv) a $\beta_2$-adrenoreceptor agonist.

In certain embodiments, the weight ratio of the xanthine compound to the dihydropyridine in a method provided herein is ranging from about 1 to about 180, from about 2 to about 100, from about 2 to about 50, or from about 2 to about 20. In certain embodiments, the weight ratio of the xanthine compound to the dihydropyridine in a method provided herein is ranging from about 1 to about 180. In certain embodiments, the weight ratio of the xanthine compound to the dihydropyridine in a method provided herein is ranging from about 2 to about 100. In certain embodiments, the weight ratio of the xanthine compound to the dihydropyridine in a method provided herein is ranging from about 2 to about 50. In certain embodiments, the weight ratio of the xanthine compound to the dihydropyridine in a method provided herein is ranging from about 2 to about 20. In certain embodiments, the weight ratio of the xanthine compound to the dihydropyridine in a method provided herein is about 2, about 4, about 6, about 8, about 10, about 12, about 14, about 16, about 18, or about 20.

In certain embodiments, the dihydropyridine in a method provided herein is administered concurrently or sequentially in any order with the xanthine compound, histamine $H_1$-receptor agonist, histamine $H_2$-receptor agonist, histamine $H_3$-receptor antagonist, or $\beta_2$-adrenoreceptor agonist. In certain embodiments, the dihydropyridine in a method provided herein is administered concurrently with the xanthine compound. In certain embodiments, the dihydropyridine in a method provided herein is administered concurrently with the xanthine compound in a single pharmaceutical composition provided herein. In certain embodiments, the dihydropyridine in a method provided herein is administered concurrently with the xanthine compound, histamine $H_1$-receptor agonist, histamine $H_2$-receptor agonist, a histamine $H_3$-receptor antagonist, or a $\beta_2$-adrenoreceptor agonist. In certain embodiments, the dihydropyridine in a method provided herein is administered concurrently with the xanthine compound, histamine $H_1$-receptor agonist, histamine $H_2$-receptor agonist, a histamine $H_3$-receptor antagonist, or $\beta_2$-adrenoreceptor agonist in a single pharmaceutical composition provided herein.

In one embodiment, a method provided herein comprises administering to the subject: (i) betahistine, a metabolite thereof, or an isotopic variant thereof; or a pharmaceutically acceptable salt, hydrate, or solvate thereof; and (ii) one or more compounds, wherein each compound is independently a PDE inhibitor, an adenosine receptor antagonist, a calcium channel blocker, or a $\beta_2$-adrenergic receptor agonist.

In another embodiment, a method provided herein comprises administering to the subject: (i) betahistine, a metabolite thereof, or an isotopic variant thereof; or a pharmaceutically acceptable salt, hydrate, or solvate thereof; and (ii) a PDE inhibitor, an adenosine receptor antagonist, a calcium channel blocker, and a $\beta_2$-adrenergic receptor agonist.

In one embodiment, a method provided herein comprises administering to the subject: (i) betahistine, a metabolite thereof, or an isotopic variant thereof; or a pharmaceutically acceptable salt, hydrate, or solvate thereof; and (ii) a PDE inhibitor or an adenosine receptor antagonist. In another embodiment, a method provided herein comprises administering to the subject: (i) betahistine, a metabolite thereof, or an isotopic variant thereof; or a pharmaceutically acceptable salt, hydrate, or solvate thereof; and (ii) a calcium channel blocker. In yet another embodiment, a method provided herein comprises administering to the subject: (i) betahistine, a metabolite thereof, or an isotopic variant thereof; or a pharmaceutically acceptable salt, hydrate, or solvate thereof; and (ii) a $\beta_2$-adrenergic receptor agonist.

In yet another embodiment, a method provided herein comprises administering to the subject: (i) betahistine, a metabolite thereof, or an isotopic variant thereof; or a pharmaceutically acceptable salt, hydrate, or solvate thereof; and (ii) two compounds, wherein each compound is independently a PDE inhibitor, an adenosine receptor antagonist, a calcium channel blocker, or a $\beta_2$-adrenergic receptor agonist.

In one embodiment, a method provided herein comprises administering to the subject: (i) betahistine, a metabolite thereof, or an isotopic variant thereof; or a pharmaceutically acceptable salt, hydrate, or solvate thereof; (ii) a PDE inhibitor or adenosine receptor antagonist; and (iii) a calcium channel blocker. In another embodiment, a method provided herein comprises administering to the subject: (i) betahistine, a metabolite thereof, or an isotopic variant thereof; or a pharmaceutically acceptable salt, hydrate, or solvate thereof; (ii) a PDE inhibitor or adenosine receptor antagonist; and (iii) a $\beta_2$-adrenergic receptor agonist. In yet another embodiment, a method provided herein comprises administering to the subject: (i) betahistine, a metabolite thereof, or an isotopic variant thereof; or a pharmaceutically acceptable salt, hydrate, or solvate thereof; (ii) a calcium channel blocker; and (iii) a $\beta_2$-adrenergic receptor agonist.

In still another embodiment, a method provided herein comprises administering to the subject: (i) betahistine, a metabolite thereof, or an isotopic variant thereof; or a pharmaceutically acceptable salt, hydrate, or solvate thereof; and (ii) three compounds, wherein each compound is independently a PDE inhibitor, an adenosine receptor antagonist, a calcium channel blocker, or a $\beta_2$-adrenergic receptor agonist.

In one embodiment, a method provided herein comprises administering to the subject: (i) betahistine, a metabolite thereof, or an isotopic variant thereof; or a pharmaceutically acceptable salt, hydrate, or solvate thereof; (ii) a PDE inhibitor or an adenosine receptor antagonist; (iii) a calcium channel blocker; and (iv) a $\beta_2$-adrenergic receptor agonist.

In certain embodiments, the weight ratio of (i) the phosphodiesterase inhibitor or adenosine receptor antagonist to (ii) betahistine in a method provided herein is ranging from about 2 to about 200, from about 4 to about 100, from about 5 to about 50, or from about 10 to about 30. In certain embodiments, the weight ratio of (i) the phosphodiesterase inhibitor or adenosine receptor antagonist to (ii) betahistine in a method provided herein is about 10, about 11, about 12, about 13, about 14, about 15, about 16, about 17, about 18, about 19, about 20, about 21, about 22, about 23, about 24, about 25, about 26, about 27, about 28, about 29, or about 30.

In certain embodiments, the weight ratio of (i) the calcium channel blocker to (ii) betahistine in a method provided herein is ranging from about 1 to about 50, from about 1 to about 40, from about 1 to about 20, or from about 1 to about 10. In certain embodiments, the weight ratio of (i) the calcium channel blocker to (ii) betahistine in a method provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, the weight ratio of (i) betahistine to (ii) the $\beta_2$-adrenoreceptor agonist in a method provided herein is ranging from about 1 to about 100, from about 1 to about 50, from about 1 to about 30, or from about 1 to about 20. In certain embodiments, the weight ratio of (i) betahistine to (ii) the $\beta_2$-adrenoreceptor agonist in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a method provided herein comprises administering to the subject betahistine, a metabolite thereof, or an isotopic variant thereof; or a pharmaceutically acceptable salt, hydrate, or solvate thereof in a subtherapeutically effective amount. In certain embodiments, a method provided herein comprises administering to the subject betahistine in the amount ranging from about 0.1 to about 100, from about 0.5 to about 50, from about 1 to about 20 mg per day. In certain embodiments, a method provided herein comprises administering to the subject betahistine in the amount ranging from about 0.1 to about 100 mg per day.

In certain embodiments, a method provided herein comprises administering to the subject betahistine in the amount ranging from about 0.5 to about 50 mg per day. In certain embodiments, a method provided herein comprises administering to the subject betahistine in the amount ranging from about 1 to about 20 mg per day. In certain embodiments, a method provided herein comprises administering to the subject betahistine in the amount of about 1, about 2, about 3, about 4, about 5, about 6, about 8, about 10, about 12, about 14, about 16, about 18, or about 20 mg per day.

In certain embodiments, betahistine in a method provided herein is administered once daily (QD) or divided into multiple daily doses such as twice daily (BID), three times daily (TID), four times daily (QID), five times daily, or six times daily. In certain embodiments, betahistine in a method provided herein is administered QD. In certain embodiments, betahistine in a method provided herein is administered BID. In certain embodiments, betahistine in a method provided herein is administered TID. In certain embodiments, betahistine in a method provided herein is administered QID.

In certain embodiments, betahistine in a method provided herein is administered concurrently or sequentially in any order with the phosphodiesterase inhibitor, adenosine receptor antagonist, calcium channel blocker, and/or $\beta_2$-adrenoreceptor agonist. In certain embodiments, betahistine in a method provided herein is administered concurrently with the $\beta_2$-adrenoreceptor agonist. In certain embodiments, the dihydropyridine in a method provided herein is administered concurrently with the $\beta_2$-adrenoreceptor agonist in a single pharmaceutical composition provided herein. In certain embodiments, betahistine in a method provided herein is administered concurrently with the phosphodiesterase inhibitor, adenosine receptor antagonist, calcium channel blocker, and/or $\beta_2$-adrenoreceptor agonist. In certain embodiments, the dihydropyridine in a method provided herein is administered concurrently with the phosphodiesterase inhibitor, adenosine receptor antagonist, calcium channel blocker, and/or $\beta_2$-adrenoreceptor agonist in a single pharmaceutical composition provided herein.

In one embodiment, a method provided herein comprises administering to the subject: (i) a xanthine compound or an isotopic variant thereof, or a pharmaceutically acceptable salt, hydrate, or solvate thereof; (ii) betahistine, a metabolite thereof, or an isotopic variant thereof, or a pharmaceutically acceptable salt, hydrate, or solvate thereof, and (iii) optionally one or more compounds, wherein each compound is independently a calcium channel blocker or a $\beta_2$-adrenergic receptor agonist.

In another embodiment, a method provided herein comprises administering to the subject: (i) a xanthine compound or an isotopic variant thereof, or a pharmaceutically acceptable salt, hydrate, or solvate thereof; and (ii) betahistine, a metabolite thereof, or an isotopic variant thereof; or a pharmaceutically acceptable salt, hydrate, or solvate thereof.

In yet another embodiment, a method provided herein comprises administering to the subject: (i) a xanthine compound or an isotopic variant thereof, or a pharmaceutically acceptable salt, hydrate, or solvate thereof; (ii) betahistine, a metabolite thereof, or an isotopic variant thereof; or a pharmaceutically acceptable salt, hydrate, or solvate thereof, and (iii) a calcium channel blocker or a $\beta_2$-adrenergic receptor agonist.

In one embodiment, a method provided herein comprises administering to the subject: (i) a xanthine compound or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; and (iii) a calcium channel blocker. In another embodiment, a method provided herein comprises administering to the subject: (i) a xanthine compound or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; and (iii) a $\beta_2$-adrenergic receptor agonist.

In still another embodiment, a method provided herein comprises administering to the subject: (i) a xanthine compound or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; and (iii) two compounds, wherein each compound is independently a calcium channel blocker or a $\beta_2$-adrenergic receptor agonist.

In one embodiment, a method provided herein comprises administering to the subject: (i) a xanthine compound or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; (iii) a calcium channel blocker; and (iv) a $\beta_2$-adrenergic receptor agonist.

In certain embodiments, the weight ratio of the xanthine compound to betahistine in a method provided herein is ranging from about 2 to about 200, from about 4 to about 100, from about 5 to about 50, or from about 10 to about 30. In certain embodiments, the weight ratio of the xanthine compound to betahistine in a method provided herein is about 10, about 12, about 14, about 16, about 17, about 18, about 19, about 20, about 21, about 22, about 23, about 24, about 25, about 26, about 27, about 28, about 29, or about 30.

In certain embodiments, betahistine in a method provided herein is administered concurrently or sequentially in any order with the xanthine compound, calcium channel blocker, or $\beta_2$-adrenoreceptor agonist. In certain embodiments, betahistine in a method provided herein is administered concurrently with the xanthine compound, calcium channel blocker, and $\beta_2$-adrenoreceptor agonist. In certain embodiments, the dihydropyridine in a method provided herein is administered concurrently with the xanthine compound, calcium channel blocker, and $\beta_2$-adrenoreceptor agonist in a single pharmaceutical composition provided herein.

In one embodiment, a method provided herein comprises administering to the subject: (i) a dihydropyridine or an isotopic variant thereof, or a pharmaceutically acceptable salt, hydrate, or solvate thereof; (ii) betahistine, a metabolite thereof, or an isotopic variant thereof; or a pharmaceutically acceptable salt, hydrate, or solvate thereof, and (iii) optionally one or more compounds, wherein each compound is independently a phosphodiesterase inhibitor, an adenosine receptor antagonist, or a $\beta_2$-adrenoreceptor agonist.

In another embodiment, a method provided herein comprises administering to the subject: (i) a dihydropyridine or an isotopic variant thereof, or a pharmaceutically acceptable salt, hydrate, or solvate thereof; and (ii) betahistine, a metabolite thereof, or an isotopic variant thereof; or a pharmaceutically acceptable salt, hydrate, or solvate thereof.

In yet another embodiment, a method provided herein comprises administering to the subject: (i) a dihydropyridine or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof, and (iii) a phosphodiesterase inhibitor, an adenosine receptor antagonist, and a $\beta_2$-adrenoreceptor agonist.

In one embodiment, a method provided herein comprises administering to the subject: (i) a dihydropyridine or an isotopic variant thereof, or a pharmaceutically acceptable salt, hydrate, or solvate thereof; (ii) betahistine, a metabolite thereof, or an isotopic variant thereof; or a pharmaceutically acceptable salt, hydrate, or solvate thereof; and (iii) a phosphodiesterase inhibitor or an adenosine receptor antagonist. In another embodiment, a method provided herein comprises administering to the subject: (i) a dihydropyridine or an isotopic variant thereof; or a pharmaceutically acceptable salt, hydrate, or solvate thereof; (ii) betahistine, a metabolite thereof, or an isotopic variant thereof, or a pharmaceutically acceptable salt, hydrate, or solvate thereof; and (iii) a $\beta_2$-adrenoreceptor agonist.

In still another embodiment, a method provided herein comprises administering to the subject: (i) a dihydropyridine or an isotopic variant thereof, or a pharmaceutically acceptable salt, hydrate, or solvate thereof; (ii) betahistine, a metabolite thereof, or an isotopic variant thereof, or a pharmaceutically acceptable salt, hydrate, or solvate thereof; and (iii) two compounds, wherein each compound is independently a phosphodiesterase inhibitor, an adenosine receptor antagonist, or a $\beta_2$-adrenoreceptor agonist.

In one embodiment, a method provided herein comprises administering to the subject: (i) a dihydropyridine or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; (iii) a phosphodiesterase inhibitor or an adenosine receptor antagonist; and (iv) a $\beta_2$-adrenoreceptor agonist.

In certain embodiments, the weight ratio of the dihydropyridine to betahistine in a method provided herein is ranging from about 1 to about 50, from about 1 to about 40, from about 1 to about 20, or from about 1 to about 10. In certain embodiments, the weight ratio of the dihydropyridine to betahistine in a method provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, betahistine in a method provided herein is administered concurrently or sequentially in any order with the phosphodiesterase inhibitor, adenosine receptor antagonist, dihydropyridine, or $\beta_2$-adrenoreceptor agonist. In certain embodiments, betahistine in a method provided herein is administered concurrently with the phosphodiesterase inhibitor, adenosine receptor antagonist, dihydropyridine, and $\beta_2$-adrenoreceptor agonist. In certain embodiments, the dihydropyridine in a method provided herein is administered concurrently with the phosphodiesterase inhibitor, adenosine receptor antagonist, dihydropyridine, and $\beta_2$-adrenoreceptor agonist in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof; (ii) a dihydropyridine or an isotopic variant thereof; or a pharmaceutically acceptable salt, hydrate, or solvate thereof; (iii) betahistine, a metabolite thereof, or an isotopic variant thereof; or a pharmaceutically acceptable salt, hydrate, or solvate thereof; and (iv) optionally a $\beta_2$-adrenoreceptor agonist.

In certain embodiments, betahistine in a method provided herein is administered concurrently or sequentially in any order with the xanthine compound, dihydropyridine, or $β_2$-adrenoreceptor agonist. In certain embodiments, betahistine in a method provided herein is administered concurrently with the xanthine compound, dihydropyridine, and $β_2$-adrenoreceptor agonist. In certain embodiments, the dihydropyridine in a method provided herein is administered concurrently with the xanthine compound, dihydropyridine, and $β_2$-adrenoreceptor agonist in a single pharmaceutical composition provided herein.

In one embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) one or more compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) a PDE inhibitor or an adenosine receptor antagonist. In another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) a calcium channel blocker. In yet another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) a histamine $H_1$-receptor agonist, a histamine $H_2$-receptor agonist, or a histamine $H_3$-receptor antagonist.

In yet another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) two compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; (ii) a PDE inhibitor or adenosine receptor antagonist; and (iii) a calcium channel blocker. In another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; (ii) a PDE inhibitor or adenosine receptor antagonist; and (iii) a histamine $H_1$-receptor agonist, a histamine $H_2$-receptor agonist, or a histamine $H_3$-receptor antagonist. In yet another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; (ii) a calcium channel blocker; and (iii) a histamine $H_1$-receptor agonist, a histamine $H_2$-receptor agonist, or a histamine $H_3$-receptor antagonist.

In still another embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; and (ii) three compounds, wherein each compound is independently a PDE inhibitor, an adenosine receptor antagonist, a calcium channel blocker, a histamine $H_1$-receptor agonist, a histamine $H_2$-receptor agonist, or a histamine $H_3$-receptor antagonist.

In one embodiment, a method provided herein comprises administering to the subject: (i) albuterol, or an enantionmer, a mixture of enantiomers; or levabuterol; or an isotopic variant thereof; or a pharmaceutically acceptable salt, hydrate, or solvate thereof; (ii) a PDE inhibitor or an adenosine receptor antagonist; (iii) a calcium channel blocker; and (iv) a histamine $H_1$-receptor agonist, a histamine $H_2$-receptor agonist, or a histamine $H_3$-receptor antagonist.

In certain embodiments, the weight ratio of (i) the phosphodiesterase inhibitor or adenosine receptor antagonist to (ii) albuterol or levalbuterol in a method provided herein is ranging from about 1 to about 1,000, from about 10 to about 500, from about 20 to about 200, or from about 50 to about 200. In certain embodiments, the weight ratio of (i) the phosphodiesterase inhibitor or adenosine receptor antagonist to (ii) albuterol or levalbuterol in a method provided herein is about 50, about 60, about 70, about 80, about 90, about 100, about 110, about 120, about 130, about 140, about 150, about 160, about 170, about 180, about 190, or about 200.

In certain embodiments, the weight ratio of (i) the calcium channel blocker to (ii) albuterol or levalbuterol in a method provided herein is ranging from about 1 to about 100, from about 5 to about 50, or from about 5 to about 20. In certain embodiments, the weight ratio of (i) the calcium channel blocker to (ii) albuterol or levalbuterol in a method provided herein is about 5, about 6, about 7, about 8, about 9, about 10, about 11, about 12, about 13, about 14, about 15, about 16, about 17, about 18, about 19, or about 20.

In certain embodiments, the weight ratio of (i) the histamine $H_1$-receptor agonist, histamine $H_2$-receptor agonist, or histamine $H_3$-receptor antagonist to (ii) albuterol or levalbuterol in a method provided herein is ranging from about 1 to about 100, from about 1 to about 50, from about 1 to about 30, or from about 1 to about 20. In certain embodiments, the weight ratio of (i) the histamine $H_1$-receptor agonist, histamine $H_2$-receptor agonist, histamine $H_3$-receptor antagonist to (ii) albuterol or levalbuterol in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a method provided herein comprises administering to the subject albuterol, or an enantionmer, a mixture of enantiomers; or levabuterol; or an isotopic variant thereof; or a pharmaceutically acceptable salt, hydrate, or solvate thereof in a subtherapeutically effective amount. In certain embodiments, a method provided herein comprises administering to the subject albuterol or levalbuterol (micronized or non-micronized) in the amount ranging from about 0.1 to about 50, from about 0.2 to about 20, or from about 0.5 to about 10 mg per day. In certain embodiments, a method provided herein comprises administering to the subject albuterol or levalbuterol in the amount ranging from about 0.1 to about 50 mg per day. In certain embodiments, a method provided herein comprises administering to the subject albuterol or levalbuterol in the amount ranging from about 0.2 to about 20 mg per day. In certain embodiments, a method provided herein comprises administering to the subject albuterol or levalbuterol in the amount ranging from about 0.5 to about 10 mg per day. In certain embodiments, a method provided herein comprises administering to the subject albuterol or levalbuterol in the amount of about 0.1, about 0.2, about 0.5, about 1, about 1.5, about 2, about 2.5, about 3, about 3.5, about 4, about 4.5, about 5, about 6, about 7, about 8, about 9, or about 10 mg per day.

In certain embodiments, albuterol or levalbuterol in a method provided herein is administered once daily (QD) or divided into multiple daily doses such as twice daily (BID), three times daily (TID), four times daily (QID), five times daily, or six times daily. In certain embodiments, albuterol or levalbuterol in a method provided herein is administered QD. In certain embodiments, albuterol or levalbuterol in a method provided herein is administered BID. In certain embodiments, albuterol or levalbuterol in a method provided herein is administered TID. In certain embodiments, albuterol or levalbuterol in a method provided herein is administered QID.

In certain embodiments, albuterol or levalbuterol in a method provided herein is administered concurrently or sequentially in any order with the phosphodiesterase inhibitor, adenosine receptor antagonist, calcium channel blocker, histamine $H_1$-receptor agonist, histamine $H_2$-receptor agonist, or histamine $H_3$-receptor antagonist. In certain embodiments, albuterol or levalbuterol in a method provided herein is administered currently with the histamine $H_1$-receptor agonist, histamine $H_2$-receptor agonist, or histamine $H_3$-receptor antagonist. In certain embodiments, albuterol or levalbuterol in a method provided herein is administered currently with the histamine $H_1$-receptor agonist, histamine $H_2$-receptor agonist, or histamine $H_3$-receptor antagonist in a single pharmaceutical composition provided herein. In certain embodiments, albuterol or levalbuterol in a method provided herein is administered currently with the phosphodiesterase inhibitor, adenosine receptor antagonist, calcium channel blocker, histamine $H_1$-receptor agonist, histamine $H_2$-receptor agonist, or histamine $H_3$-receptor antagonist. In certain embodiments, albuterol or levalbuterol in a method provided herein is administered currently with the phosphodiesterase inhibitor, adenosine receptor antagonist, calcium channel blocker, histamine $H_1$-receptor agonist, histamine $H_2$-receptor agonist, or histamine $H_3$-receptor antagonist in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof, (ii) albuterol, or an enantionmer, a mixture of enantiomers; or levalbuterol; or an isotopic variant thereof, or a pharmaceutically acceptable salt, hydrate, or solvate thereof, and (iii) optionally one or more compounds, wherein each compound is independently a calcium channel blocker, a histamine $H_1$-receptor agonist, a histamine $H_2$-receptor agonist, or a histamine $H_3$-receptor antagonist.

In another embodiment, a method provided herein comprises administering to the subject: (i) a xanthine compound or an isotopic variant thereof; or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, a method provided herein comprises administering to the subject: (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker, a histamine $H_1$-receptor agonist, a histamine $H_2$-receptor agonist, or a histamine $H_3$-receptor antagonist.

In one embodiment, a method provided herein comprises administering to the subject: (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker. In another embodiment, a method provided herein comprises administering to the subject: (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a histamine $H_1$-receptor agonist, a histamine $H_2$-receptor agonist, or a histamine $H_3$-receptor antagonist.

In still another embodiment, a method provided herein comprises administering to the subject: (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) two compounds, wherein each compound is independently a calcium channel blocker, a histamine $H_1$-receptor agonist, a histamine $H_2$-receptor agonist, or a histamine $H_3$-receptor antagonist.

In one embodiment, a method provided herein comprises administering to the subject: (i) a xanthine compound or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a calcium channel blocker; and (iv) a histamine $H_1$- and/or $H_2$-receptor agonist, and/or a histamine $H_3$-receptor antagonist.

In certain embodiments, the weight ratio of (i) the xanthine compound to (ii) albuterol or levalbuterol in a method provided herein is ranging from about 1 to about 1,000, from about 10 to about 500, from about 20 to about 400, or from about 40 to about 300. In certain embodiments, the weight ratio of (i) the xanthine compound to (ii) albuterol or levalbuterol in a method provided herein is about 40, about 60, about 80, about 100, about 120, about 140, about 160, about 180, about 200, about 220, about 240, about 260, about 280, or about 300.

In certain embodiments, albuterol or levalbuterol in a method provided herein is administered concurrently or sequentially in any order with the xanthine compound, calcium channel blocker, histamine $H_1$-receptor agonist, histamine $H_2$-receptor agonist, or histamine $H_3$-receptor antagonist. In certain embodiments, albuterol or levalbuterol in a method provided herein is administered currently with the xanthine compound, calcium channel blocker, histamine H$_1$-receptor agonist, histamine H$_2$-receptor agonist, or histamine H$_3$-receptor antagonist. In certain embodiments, albuterol or levalbuterol in a method provided herein is administered currently with the xanthine compound, calcium channel blocker, histamine H$_1$-receptor agonist, histamine H$_2$-receptor agonist, or histamine H$_3$-receptor antagonist in a single pharmaceutical composition provided herein.

In one embodiment, a method provided herein comprises administering to the subject: (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) optionally one or more compounds, wherein each compound is independently a phosphodiesterase inhibitor, an adenosine receptor antagonist, a histamine H$_1$-receptor agonist, histamine H$_2$-receptor agonist, or histamine H$_3$-receptor antagonist.

In another embodiment, a method provided herein comprises administering to the subject: (i) a dihydropyridine or an isotopic variant thereof, or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, a method provided herein comprises administering to the subject: (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor, an adenosine receptor antagonist, a histamine H$_1$-receptor agonist, a histamine H$_2$-receptor agonist, or a histamine H$_3$-receptor antagonist.

In one embodiment, a method provided herein comprises administering to the subject: (i) a dihydropyridine or an isotopic variant thereof, or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor or an adenosine receptor antagonist. In another embodiment, a method provided herein comprises administering to the subject: (i) a dihydropyridine or an isotopic variant thereof, or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a histamine H$_1$-receptor agonist, a histamine H$_2$-receptor agonist, or a histamine H$_3$-receptor antagonist.

In still another embodiment, a method provided herein comprises administering to the subject: (i) a dihydropyridine or an isotopic variant thereof, or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) two compounds, wherein each compound is independently a phosphodiesterase inhibitor, an adenosine receptor antagonist, a histamine H$_1$-receptor agonist, a histamine H$_2$-receptor agonist, or a histamine H$_3$-receptor antagonist.

In one embodiment, a method provided herein comprises administering to the subject: (i) a dihydropyridine or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a phosphodiesterase inhibitor or an adenosine receptor antagonist; and (iv) a histamine H$_1$-receptor agonist, a histamine H$_2$-receptor agonist, or a histamine H$_3$-receptor antagonist.

In certain embodiments, the weight ratio of (i) the dihydropyridine to (ii) albuterol or levalbuterol in a method provided herein is ranging from about 1 to about 100, from about 5 to about 50, or from about 10 to about 20. In certain embodiments, the weight ratio of (i) the dihydropyridine to (ii) albuterol or levalbuterol in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, albuterol or levalbuterol in a method provided herein is administered concurrently or sequentially in any order with the phosphodiesterase inhibitor, adenosine receptor antagonist, dihydropyridine, histamine H$_1$-receptor agonist, histamine H$_2$-receptor agonist, or histamine H$_3$-receptor antagonist. In certain embodiments, albuterol or levalbuterol in a method provided herein is administered currently with the phosphodiesterase inhibitor, adenosine receptor antagonist, dihydropyridine, histamine H$_1$-receptor agonist, histamine H$_2$-receptor agonist, or histamine H$_3$-receptor antagonist. In certain embodiments, albuterol or levalbuterol in a method provided herein is administered currently with the phosphodiesterase inhibitor, adenosine receptor antagonist, dihydropyridine, histamine H$_1$-receptor agonist, histamine H$_2$-receptor agonist, or histamine H$_3$-receptor antagonist in a single pharmaceutical composition provided herein.

In one embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) optionally one or more compounds, wherein each compound is independently a phosphodiesterase inhibitor, an adenosine receptor antagonist, or a calcium channel blocker.

In another embodiment, a method provided herein comprises administering to the subject: (i) betahistine, a metabolite thereof, or an isotopic variant thereof; or a pharmaceutically acceptable salt, hydrate, or solvate thereof; and (ii) albuterol, or an enantionmer, a mixture of enantiomers; or levalbuterol; or an isotopic variant thereof; or a pharmaceutically acceptable salt, hydrate, or solvate thereof.

In yet another embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor, an adenosine receptor antagonist, or a calcium channel blocker.

In one embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a phosphodiesterase inhibitor or an adenosine receptor antagonist. In another embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) a calcium channel blocker.

In still another embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; and (iii) two compounds, wherein each compound is independently a phosphodiesterase inhibitor, an adenosine receptor antagonist, or a calcium channel blocker.

In one embodiment, a method provided herein comprises administering to the subject: (i) betahistine, a metabolite thereof, or an isotopic variant thereof; or a pharmaceutically acceptable salt, hydrate, or solvate thereof; (ii) albuterol, or an enantionmer, a mixture of enantiomers; or levalbuterol; or an isotopic variant thereof; or a pharmaceutically acceptable salt, hydrate, or solvate thereof; (iii) a phosphodiesterase inhibitor or an adenosine receptor antagonist; and (iv) a calcium channel blocker.

In certain embodiments, the weight ratio of (i) betahistine to (ii) albuterol or levalbuterol in a method provided herein is ranging from about 1 to about 100, from about 1 to about 50, from about 1 to about 20, or from about 1 to about 10. In certain embodiments, the weight ratio of (i) betahistine to (ii) albuterol or levalbuterol in a method provided herein is about 1, about 2, about 3, about 4, about 5, about 6, about 7, about 8, about 9, or about 10.

In certain embodiments, albuterol or levalbuterol in a method provided herein is administered concurrently or sequentially in any order with the phosphodiesterase inhibitor, adenosine receptor antagonist; calcium channel blocker, or betahistine. In certain embodiments, albuterol or levalbuterol in a method provided herein is administered currently with betahistine. In certain embodiments, albuterol or levalbuterol in a method provided herein is administered currently with betahistine in a single pharmaceutical composition provided herein. In certain embodiments, albuterol or levalbuterol in a method provided herein is administered currently with the phosphodiesterase inhibitor, adenosine receptor antagonist; calcium channel blocker, and betahistine. In certain embodiments, albuterol or levalbuterol in a method provided herein is administered currently with the phosphodiesterase inhibitor, adenosine receptor antagonist; calcium channel blocker, and betahistine in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof; (ii) a dihydropyridine or an isotopic variant thereof; or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof; and (iv) optionally a histamine $H_1$- and/or $H_2$-receptor agonist, and/or a histamine $H_3$-receptor antagonist.

In certain embodiments, albuterol or levalbuterol in a method provided herein is administered concurrently or sequentially in any order with the xanthine compound, dihydropyridine, a histamine $H_1$-receptor agonist, a histamine $H_2$-receptor agonist, or a histamine $H_3$-receptor antagonist. In certain embodiments, albuterol or levalbuterol in a method provided herein is administered currently with the xanthine compound, dihydropyridine, a histamine $H_1$-receptor agonist, a histamine $H_2$-receptor agonist, or a histamine $H_3$-receptor antagonist. In certain embodiments, albuterol or levalbuterol in a method provided herein is administered currently with the xanthine compound, dihydropyridine, a histamine $H_1$-receptor agonist, a histamine $H_2$-receptor agonist, or a histamine $H_3$-receptor antagonist in a single pharmaceutical composition provided herein.

In one embodiment, a method provided herein comprises administering to the subject: (i) a xanthine compound or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof; and (iv) optionally a calcium channel blocker.

In certain embodiments, albuterol or levalbuterol in a method provided herein is administered concurrently or sequentially in any order with the xanthine compound, calcium channel blocker, or betahistine. In certain embodiments, albuterol or levalbuterol in a method provided herein is administered currently with the xanthine compound, calcium channel blocker, and betahistine. In certain embodiments, albuterol or levalbuterol in a method provided herein is administered currently with the xanthine compound, calcium channel blocker, and betahistine in a single pharmaceutical composition provided herein.

In one embodiment, a method provided herein comprises administering to the subject: (i) a dihydropyridine or an isotopic variant thereof; or a pharmaceutically acceptable salt, hydrate, or solvate thereof; (ii) betahistine, a metabolite thereof, or an isotopic variant thereof; or a pharmaceutically acceptable salt, hydrate, or solvate thereof; (iii) albuterol, or an enantionmer, a mixture of enantiomers; or levalbuterol; or an isotopic variant thereof; or a pharmaceutically acceptable salt, hydrate, or solvate thereof; and (iv) optionally a PDE inhibitor or an adenosine receptor antagonist.

In certain embodiments, albuterol or levalbuterol in a method provided herein is administered concurrently or sequentially in any order with the PDE inhibitor, adenosine receptor antagonist, dihydropyridine, or betahistine. In certain embodiments, albuterol or levalbuterol in a method provided herein is administered currently with the PDE inhibitor, adenosine receptor antagonist, dihydropyridine, and betahistine. In certain embodiments, albuterol or levalbuterol in a method provided herein is administered currently with the PDE inhibitor, adenosine receptor antagonist, dihydropyridine, and betahistine in a single pharmaceutical composition provided herein.

In one embodiment, a method provided herein comprises administering to the subject: (i) a xanthine compound or an isotopic variant thereof, or a pharmaceutically acceptable salt, hydrate, or solvate thereof, (ii) a dihydropyridine or an isotopic variant thereof, or a pharmaceutically acceptable salt, hydrate, or solvate thereof; (iii) betahistine, a metabolite thereof, or an isotopic variant thereof; or a pharmaceutically acceptable salt, hydrate, or solvate thereof, and (iv) albuterol, or an enantionmer, a mixture of enantiomers; or levalbuterol; or an isotopic variant thereof, or a pharmaceutically acceptable salt, hydrate, or solvate thereof.

In certain embodiments, albuterol or levalbuterol in a method provided herein is administered concurrently or sequentially in any order with the xanthine compound, dihydropyridine, or betahistine. In certain embodiments, albuterol or levalbuterol in a method provided herein is administered currently with the xanthine compound, dihydropyridine, and betahistine. In certain embodiments, albuterol or levalbuterol in a method provided herein is administered currently with the xanthine compound, dihydropyridine, and betahistine in a single pharmaceutical composition provided herein.

In one embodiment, a method provided herein comprises administering to the subject aminophylline or theophylline. In another embodiment, a method provided herein comprises administering to the subject nifedipine. In yet another embodiment, a method provided herein comprises administering to the subject betahistine or betahistine hydrochloride. In still another embodiment, a method provided herein comprises administering to the subject albuterol, albuterol hydrochloride, levalbuterol, or levalbuterol hydrochloride.

In one embodiment, a method provided herein comprises administering to the subject (i) aminophylline or theophylline and (ii) nifedipine. In another embodiment, a method provided herein comprises administering to the subject (i) aminophylline or theophylline and (ii) betahistine or betahistine hydrochloride. In yet another embodiment, a method provided herein comprises administering to the subject (i) aminophylline or theophylline and (ii) albuterol, albuterol hydrochloride, levalbuterol, or levalbuterol hydrochloride. In yet another embodiment, a method provided herein comprises administering to the subject (i) nifedipine and (ii) betahistine or betahistine hydrochloride. In yet another embodiment, a method provided herein comprises administering to the subject (i) nifedipine and (ii) albuterol, albuterol hydrochloride, levalbuterol, or levalbuterol hydrochloride. In still another embodiment, a method provided herein comprises administering to the subject (i) betahistine or betahistine hydrochloride; and (ii) albuterol, albuterol hydrochloride, levalbuterol, or levalbuterol hydrochloride.

In one embodiment, a method provided herein comprises administering to the subject (i) aminophylline or theophylline; (ii) nifedipine; and (iii) betahistine or betahistine hydrochloride. In another embodiment, a method provided herein comprises administering to the subject (i) aminophylline or theophylline; (ii) nifedipine; and (iii) albuterol, albuterol hydrochloride, levalbuterol, or levalbuterol hydrochloride. In yet another embodiment, a method provided herein comprises administering to the subject (i) aminophylline or theophylline; (ii) betahistine or betahistine hydrochloride; and (iii) albuterol, albuterol hydrochloride, levalbuterol, or levalbuterol hydrochloride.

In one embodiment, a method provided herein comprises administering to the subject (i) aminophylline or theophylline; (ii) nifedipine; (iii) betahistine or betahistine hydrochloride; and (iv) albuterol, albuterol hydrochloride, levalbuterol, or levalbuterol hydrochloride.

In certain embodiments, the weight ratio of theophylline to nifedipine in a method provided herein is ranging from about 1 to about 180, from about 2 to about 100, from about 2 to about 50, or from about 2 to about 20. In certain embodiments, the weight ratio of theophylline to nifedipine in a method provided herein is ranging from about 1 to about 180. In certain embodiments, the weight ratio of theophylline to nifedipine in a method provided herein is ranging from about 2 to about 100. In certain embodiments, the weight ratio of theophylline to nifedipine in a method provided herein is ranging from about 2 to about 50. In certain embodiments, the weight ratio of theophylline to nifedipine in a method provided herein is ranging from about 2 to about 20. In certain embodiments, the weight ratio of theophylline to nifedipine in a method provided herein is about 2, about 4, about 6, about 8, about 10, about 12, about 14, about 16, about 18, or about 20.

In certain embodiments, the weight ratio of theophylline to betahistine in a method provided herein is ranging from about 2 to about 200, from about 4 to about 100, from about 5 to about 50, or from about 10 to about 30. In certain embodiments, the weight ratio of theophylline to betahistine in a method provided herein is about 10, about 12, about 14, about 16, about 18, about 20, about 22, about 24, about 26, about 28, or about 30.

In certain embodiments, the weight ratio of theophylline to albuterol or levalbuterol in a method provided herein is ranging from about 1 to about 1,000, from about 10 to about 500, from about 20 to about 400, or from about 40 to about 300. In certain embodiments, the weight ratio of theophylline to albuterol or levalbuterol in a method provided herein is about 40, about 60, about 80, about 100, about 120, about 140, about 160, about 180, about 200, about 220, about 240, about 260, about 280, or about 300.

In certain embodiments, the weight ratio of nifedipine to betahistine in a method provided herein is ranging from about 1 to about 50, from about 1 to about 40, from about 1 to about 20, or from about 1 to about 10. In certain embodiments, the weight ratio of nifedipine to betahistine in a method provided herein is about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10.

In certain embodiments, the weight ratio of nifedipine to albuterol or levalbuterol in a method provided herein is ranging from about 1 to about 100, from about 5 to about 50, or from about 5 to about 20. In certain embodiments, the weight ratio of nifedipine to albuterol or levalbuterol in a method provided herein is about 5, about 6, about 7, about 8, about 9, about 10, about 11, about 12, about 13, about 14, about 15, about 16, about 17, about 18, about 19, or about 20.

In certain embodiments, the weight ratio of betahistine to albuterol or levalbuterol in a method provided herein is ranging from about 1 to about 100, from about 1 to about 50, from about 1 to about 30, or from about 1 to about 20. In certain embodiments, the weight ratio of betahistine to albuterol or levalbuterol in a method provided herein is about 1, about 2, about 3, about 4, about 5, about 6, about 7, about 8, about 9, about 10, about 11, about 12, about 13, about 14, about 15, about 16, about 17, about 18, about 19, or about 20.

In certain embodiments, a method provided herein comprises administering to the subject aminophylline in a subtherapeutically effective amount. In certain embodiments, a method provided herein comprises administering to the subject aminophylline (micronized or non-micronized) in the amount ranging from about 1 to about 1,200 mg/day, from about to about 1,000 mg/day, from about 1 to about 800 mg/day, from about 1 to about 700 mg/day, from about 1 to about 600 mg/day, from about 1 to about 500 mg/day, from about 1 to about 400 mg/day, from about 1 to about 300 mg/day, from about 1 to about 200 mg/day, from about 1 to about 100 mg/day, from about 1 to about 90 mg/day, from about 1 to about 80 mg/day, from about 1 to about 70 mg/day, from about 1 to about 60 mg/day, from about 1 to about 50 mg/day, from about 1 to about 40 mg/day, from about 1 to about 30 mg/day, from about 1 to about 20 mg/day, or from about 1 to about 10 mg/day.

In certain embodiments, a method provided herein comprises administering to the subject theophylline (micronized or non-micronized) in a subtherapeutic effective amount. In certain embodiments, a method provided herein comprises administering to the subject theophylline in the amount ranging from about 1 to about 1,200, from about to about 1,000, from about 5 to about 800, or from about 10 to about 600 mg per day. In certain embodiments, a method provided herein comprises administering to the subject theophylline in the amount ranging from about 1 to about 1,200 mg per day. In certain embodiments, a method provided herein comprises administering to the subject theophylline in the amount ranging from about 1 to about 1,000 mg per day. In certain embodiments, a method provided herein comprises administering to the subject theophylline in the amount ranging from about 5 to about 800 mg per day. In certain embodiments, a method provided herein comprises administering to the subject theophylline in the amount ranging from about 20 to about 600 mg per day. In certain embodiments, a method provided herein comprises administering to the subject theophylline in the amount of about 20, about 50, about 75, about 100, about 125, about 150, about 175, about 200, about 225, about 250, about 275, about 300, about 325, about 350, about 375, about 400, about 425, about 450, about 475, about 500, about 525, about 550, about 575, or about 600 mg per day.

In certain embodiments, a method provided herein comprises administering to the subject nifedipine (micronized or non-micronized) in a subtherapeutically effective amount. In certain embodiments, a method provided herein comprises administering to the subject nifedipine in a subtherapeutic effective amount. In certain embodiments, a method provided herein comprises administering to the subject nifedipine in the amount ranging from about 0.1 to about 200, from about 1 to about 100, or from about 2 to about 60 mg per day. In certain embodiments, a method provided herein comprises administering to the subject nifedipine in the amount ranging from about 0.1 to about 200 mg per day. In certain embodiments, a method provided herein comprises administering to the subject nifedipine in the amount ranging from about 1 to about 100 mg per day. In certain embodiments, a method provided herein comprises administering to the subject nifedipine in the amount ranging from about 2 to about 60 mg per day. In certain embodiments, a method provided herein comprises administering to the subject nifedipine in the amount of about 2, about 5, about 10, about 15, about 20, about 25, about 30, about 35, about 40, about 45, about 50, about 55, or about 60 mg per day.

In certain embodiments, a method provided herein comprises administering to the subject (i) aminophylline or theophylline, (ii) nifedipine, (iii) betahistine, and (iv) albuterol or levalbuterol; wherein the amount of aminophylline or theophylline is from about 1 to about 1000 mg/day, the amount of nifedipine is from about 0.1 to about 180 mg/day, the amount of betahistine is from about 1 to about 100 mg/day, and wherein the amount of albuterol or levalbuterol is from about 0.1 to about 32 mg/day.

In certain embodiments, (i) aminophylline or theophylline, (ii) nifedipine and (iii) betahistine in a method provided herein are administered concurrently or sequentially in any order. In certain embodiments, (i) aminophylline or theophylline, (ii) nifedipine, and (iii) betahistine in a method provided herein are administered concurrently. In certain embodiments, (i) aminophylline or theophylline, (ii) nifedipine, and (iii) betahistine in a method provided herein are administered concurrently in a single pharmaceutical composition provided herein.

In certain embodiments, (i) aminophylline or theophylline, (ii) nifedipine and (iii) albuterol or levalbuterol in a method provided herein are administered concurrently or sequentially in any order. In certain embodiments, (i) aminophylline or theophylline, (ii) nifedipine, and (iii) albuterol or levalbuterol in a method provided herein are administered concurrently. In certain embodiments, (i) aminophylline or theophylline, (ii) nifedipine, and (iii) albuterol or levabuterol in a method provided herein are administered concurrently in a single pharmaceutical composition provided herein.

In certain embodiments, (i) aminophylline or theophylline, (ii) betahistine, and (iii) albuterol, albuterol hydrochloride, levalbuterol, or levalbuterol hydrochloride in a method provided herein are administered concurrently or sequentially in any order. In certain embodiments, (i) aminophylline or theophylline, (ii) betahistine, and (iii) albuterol, albuterol hydrochloride, levalbuterol, or levalbuterol hydrochloride in a method provided herein are administered concurrently. In certain embodiments, (i) aminophylline or theophylline, (ii) betahistine, and (iii) albuterol, albuterol hydrochloride, levalbuterol, or levalbuterol hydrochloride in a method provided herein are administered concurrently in a single pharmaceutical composition provided herein.

In certain embodiments, (i) aminophylline or theophylline, (ii) nifedipine, (iii) betahistine or betahistine hydrochloride, and (iv) albuterol, albuterol hydrochloride, levalbuterol, or levalbuterol hydrochloride in a method provided herein are administered concurrently or sequentially in any order. In certain embodiments, (i) aminophylline or theophylline, (ii) nifedipine, (iii) betahistine or betahistine hydrochloride, and (iv) albuterol, albuterol hydrochloride, levalbuterol, or levalbuterol hydrochloride in a method provided herein are administered concurrently. In certain embodiments, (i) aminophylline or theophylline, (ii) nifedipine, (iii) betahistine or betahistine hydrochloride, and (iv) albuterol, albuterol hydrochloride, levalbuterol, or levalbuterol hydrochloride in a method provided herein are administered concurrently in a single pharmaceutical composition provided herein.

In certain embodiments, a method provided herein comprises administering to the subject a pharmaceutical composition provided herein. In certain embodiments, the pharmaceutical composition is administered once daily (QD), or divided into multiple daily doses such as twice daily (BID), three times daily (TID), four times daily (QID), five times daily, or six times daily. In certain embodiments, the pharmaceutical composition is administered QD. In certain embodiments, the pharmaceutical composition is administered BID. In certain embodiments, the pharmaceutical composition is administered TID. In certain embodiments, the pharmaceutical composition is administered QID. In certain embodiments, the pharmaceutical composition is administered orally. In certain embodiments, the pharmaceutical composition is administered orally as a capsule.

In certain embodiments, a method provided herein comprises administering to the subject each active compound before a meal. In certain embodiments, a method provided herein comprises administering to the subject each active compound after a meal.

In certain embodiments, a method provided herein for treating cerebral vascular thrombosis comprises administering to the subject each active compound at bedtime. In certain embodiments, a method provided herein for treating cerebral vascular thrombosis comprises administering to the subject each active compound in the morning and at bedtime. In certain embodiments, a method provided herein for treating cerebral vascular thrombosis comprises administering to the subject each active compound in the morning and midday and at bedtime. In certain embodiments, a method provided herein for treating cerebral vascular thrombosis comprises administering to the subject each active compound at about 6 AM, 2 PM, and 10 PM. In certain embodiments, a method provided herein for treating cerebral vascular thrombosis comprises administering to the subject each active compound in the morning at about 4 AM to 8 AM. In certain embodiments, a method provided herein for treating cerebral vascular thrombosis comprises administering to the subject each active compound in midday at noon to 4 PM. In certain embodiments, a method provided herein for treating cerebral vascular thrombosis comprises administering to the subject each active compound at bedtime at 8 PM to midnight.

In certain embodiments, the subject is a mammal. In certain embodiments, the subject is a human.

The methods provided herein encompass treating a subject regardless of patient's age, although some diseases or disorders are more common in certain age groups. Depending on the disease to be treated and the subject's condition, each active compound can independently be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable carriers, adjuvants and vehicles appropriate for each route of administration.

It will be understood, however, that the specific dose level and frequency of dosage for any particular patient may be varied and will depend upon a variety of factors including the activity of the specific active compound employed, the metabolic stability and length of action of that active compound, the age, body weight, general health, sex, diet, mode and time of administration, rate of excretion, drug combination, the severity of the particular condition, and the host undergoing therapy.

In certain embodiments, provided herein are kits which, when used by the medical practitioner, can simplify the administration of appropriate amounts of active ingredients to a subject. In certain embodiments, the kit provided herein includes a container and a dosage form of an active compound provided herein or a pharmaceutical composition provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, water for injection USP, sodium chloride injection, Ringer's injection, dextrose injection, dextrose and sodium chloride injection, and lactated Ringer's injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

A Two-API Combination

When aminophylline (a phosphodiesterase inhibitor and adenosine receptor antagonist commonly used in the treatment of asthma) and clenbuterol (a $\beta_2$ agonist useful in the treatment of asthma) were prescribed to treat a patient needing bronchodilation, it was observed that the 2-drug combination, as undesired side effects for the prescribed treatment, increased the patient' heart rate significantly. The observation of the unwanted side effects led to the hypothesis that a combination of aminophylline and clenbuterol might be useful in treating a bradycardia patient. To test this hypothesis, an experiment was conducted, where a combination of aminophylline and clenbuterol was administered to a small group of volunteer subjects. After about 2-3 hours, the subjects' heart rates increased by 5-6 beats per minute. The effect lasted about 6 to 8 hours. For each subject in this example, an electrocardiogram (ECG) was used to monitor heart rate and A-V conduction abnormalities.

Even though an increase of 5-6 beats per minute in heart rate observed in this example was not as large as an increase typically achieved with a pacemaker implantation, such an increase is significant, especially when there is no approved drug even today for treating bradycardia patients who either did not or could not receive a pacemaker. The drug combination was tested on bradycardia patients, and the pateints treated with the 2-combination were observed to have a heart rate increase of 5-6 beats per minute on average in this example.

Example 2

Three-API Combinations

To further improve the effect of the aminophylline and clenbuterol combination on the heart rate, various combinations with active pharmaceutical ingredients were investigated. Without being bound by theory, the hypothesis in this experiment was to utilize a combination of APIs with similar mechanism of action or with the same side effect (a secondary therapeutical effects) on heart as aminophylline and clenbuterol. Oryzanol, nicotinamide, or anisodamine in combination with aminophylline and clenbuterol was tested on a small group of volunteer subjects. However, there was no further improvement observed.

Nifedipine (a calcium channel blocker) was then selected and tested. Although the primary indication of nifedipine is vasospastic angina and chronic stable angina, nifedipine combined with aminophylline and clenbuterol, when tested on a small group of volunteer subjects, led to enhanced effects on the heart rate compared to the results of Example 1. After two to three hours following administration of the 3-API combination, the subjects' heart rates increased by 7-9 beats per minute. The increased heart rate effect lasted about 6 to 8 hours. The combination of 3 APIs was then tested on patients with symptomatic sinus bradycardia. The bradycardia patients treated with the 3-drug combination were observed to have a heart rate increase of 7-9 beats per minute on average.

Example 3

Four-API Combinations

During the treatment of a vertigo patient, it was observed that the patient's heart rate was noticeably increased after administering betahistine. Although betahistine is commonly prescribed to patients with balance disorders or to alleviate vertigo symptoms associated with Ménière's disease, it had not been used for treating bradycardia. Based on this observation, betahistine was selected as one of potential APIs in combination for treating bradycardia. A combination of betahistine with aminophylline, clenbuterol, and nifedipine was then prepared and tested on a small group of healthy volunteer subjects. The results from the healthy volunteer subjects showed an increase in heart rate of 10 beats per minute or even higher. This 4-API combination was also tested on bradycardia patients. The results from the bradycardia patients showed a heart rate increase of 10 beats per minute or greater.

During the testing of the 4-API combination on bradycardia patients, a few adverse side effects were observed on some patients. These side effects included hand tremors and convulsions gastrocnemius. Therefore, a further study was conducted to determine how to avoid or reduce such side effects. After careful investigation, it was found that these side effects were related to clenbuterol. To confirm this finding, clenbuterol was replaced by albuterol in the 4-API combination, which has a similar secondary therapeutical effect on heart rate. It was found that the side effects (hand tremors and convulsions gastrocnemius) were either significantly reduced or eliminated as a result of clenbuterol being substituted with albuterol. Daily electrocardiograms were used to monitor the bradycardia patients. The patients treated with the new 4-API combination showed a heart rate increase by 10 beats per minute or greater. With this improvement, the effectiveness of the treatment on bradycardia patients was retained while the undesired side effects were minimized or eliminated.

Additional modifications were made to improve the 4-API combinations: (1) aminophylline was replaced by theophylline as aminophylline caused degradation of another API and affected the stability of a 4-API composition formulation; (2) albuterol (50% R-albuterol and 50% S-albuterol) was replaced by equivalently active levalbuterol (purity 100% R-albuterol) because (S)-albuterol is either inert or has some adverse effects; only (R)-albuterol is believe to have the desired pharmacological activities; and (3) micronized theophylline and nifedipine were used to enhance their bioavailabilities.

Example 4

4-API Pharmaceutical Formulation

Pharmaceutical formulations comprising micronized theophylline (or an isotopic variant thereof) (API-1), micronized nifedipine (or an isotopic variant thereof) (API-2), betahistine dihydrochloride (or an isotopic variant thereof) (API-3), and levalbuterol hydrochloride (or an isotopic variant thereof) (API-4) were prepared following the Current Good Manufacturing Practices (CGMPs). Levalbuterol hydrochloride (API-4) was blended with 10 wt % of total microcrystalline cellulose for 5 min. Micronized nifedipine (API-2) and 20 wt % of total microcrystalline cellulose were added and the resulting mixture was blended for 5 min. Betahistine dihydrochloride (API-3) and 30 wt % of total microcrystalline cellulose were added and the resulting mixture was blended for 5 min. Micronized theophylline (API-1) and 40 wt % of total microcrystalline cellulose were added and the resulting mixture was blended for 5 min. Mannitol, sodium starch glycolate, colloidal silicon dioxide, and citric acid were added, followed by addition of magnesium stearate. The resulting mixture was blended for 5 min and formulated into capsules in a size of 000, 00, 0, 1, 2, 3, 4, or 5. Each micronized API was prepared via jet milling.

TABLE 1

Phamaceutical Compositions

| Composition | Weight (%) |
|---|---|
| Theophylline (or an isotopic variant thereof) (API-1) | 1-20, 1-30, 2-35, 2-40, 2-45, 2-50, 2-55, 3-60, 3-65, 4-70, 4-75, 5-80, 5-85, or 5-90% |
| Nifedipine (or an isotopic variant thereof) (API-2) | 0.1-2, 0.1-3, 0.2-4, 0.2-5, 0.4-6, 0.4-6.5, 0.5-7, 0.5-7.5, 1-8, 1-8.5, 1-9, 1-9.5, or 1-10% |
| Betahistine (or an isotopic variant thereof) (HCl)$_2$ (API-3) | 0.02-1, 0.02-2, 0.02-3, 0.02-4, 0.2-5, 0.2-6, 0.2-7, 0.5-8, 0.5-9, 1-9.5, or 1-10% |
| Levalbuterol HCl (or an isotopic variant thereof) (API-4) | 0.002-0.5, 0.002-1, 0.002-1.5, 0.02-2, 0.02-2.5, 0.02-3, 0.02-3.5, 0.2-4, 0.2-4.5, or 0.2-5% |
| Microcrystalline cellulose | 2-5%, 2-10%, 5-15%, 5-20%, 5-25%, 5-30%, 5-35%, 5-40%, 10-45%, 10-50%, 10-55%, 10-60%, or 10-65% |
| Mannitol | 2-5%, 5-10%, 5-15%, 5-20%, 5-25%, 5-30%, 5-35%, 5-40%, 10-45%, 10-50%, 10-55%, 10-60%, or 10-65% |
| Sodium starch glycolate | 1-2%, 1-3%, 1-4%, or 1-5% |
| Colloidal silicon dioxide | 0.02-0.05, 0.02-0.1%, 0.02-0.15%, or 0.02-0.2% |
| Magnesium stearate | 0.05-0.1%, 0.05-0.15%, 0.1-0.2% 0.1-0.3%, 0.1-0.4%, or 0.1-0.5% |
| Citric acid | 0.1-0.2%, 0.1-0.4%, 0.1-0.6, 0.1-0.8%, or 0.1-1% |

Example 5

Quality Control

Several analytical methods for identification and quantitation of the APIs in the pharmaceutical compositions prepared were developed and fully validated following the US and global standards. One assay method was developed for identification and quantitation of API-1 and API-2 by HPLC. Another assay method was developed for identification and quantitation of API-3 and API-4 by HPLC. The United States Pharmacopeial (USP) grade reference standards of APIs were used to quantify the concentrations of the APIs in the pharmaceutical compositions.

A Distek 5100 Dissolution Apparatus was used in a dissolution assay for API-1 and API-2. A Hanson Sr8-Plus Dissolution Apparatus was used in a dissolution assay for API-3 and API-4.

Several batches of the pharmaceutical compositions were prepared. The stability studies of the pharmaceutical compositions were conducted following the US and International Council for Harmonisation (ICH) Guidelines. The stability samples were stored under the following conditions: (1) preferred conditions: 25° C.±2° C., 60%±5% relative humidity (RH); (2) accelerated conditions: 40° C.±2° C., 75%±5% RH; or (3) intermediate conditions: 30° C.±2° C., 65%±5% RH. Stability studies were completed with a 6-month under the accelerated condition at temperature of 40° C./75% RH, and an 18-month under the preferred conditions at temperature of 25° C./60% RH. The pharmaceutical compositions were stable for more than 2-years, and thus met the requirements of the US and ICH guidelines.

Example 6

Cardiovascular Evaluation of 4-API Composition in Animals

A cardiovascular evaluation of an orally administered 4-API composition in beagle dogs was carried out. Five male experimental non-naïve beagle dogs, approximately 1 year and 8 months to 1 year and 11 months of age, were selected. All animals were given a physical examination prior to selection for study. The animals were weighed periodically and observed with respect to general health and any signs of a disease. Baseline cardiovascular telemetry monitoring (body temperature, blood pressure, heart rate, and the electrocardiogram) was conducted. Electrocardiographic (ECG) tracings from the 24-hour baseline cardiovascular monitoring sessions were evaluated for all animals to rule out electrophysiological abnormalities of the heart and to determine suitability for the study. All animals had blood samples collected pretest to evaluate clinical chemistry and hematology parameters. All animals selected for study were considered suitable based on pretest evaluations.

No relevant abnormal clinical signs were noted following administration of a 4-API composition of Table 1. The clinical observations included body weights, body temperature, systolic, diastolic and mean arterial blood pressures, heart rate, RR interval, PR interval, WRS duration, QT interval and corrected QT interval, and electrocardiography.

Acute oral administration of the 4-API composition in dogs at test doses was without mortality and did not produce clinical signs or effects on body temperature, QTc, or the qualitative aspects of the ECG.

The 4-API composition at the test doses produced non-dose dependent decreases in blood pressure and slight increases in QRS duration. Dose-dependent increases in heart rate were observed at all dose levels, which resulted in rate-related changes in the quantitative ECG parameters (RR, PR, QT).

Example 7

Dosage Forms of 4-API Compositions

Several dosage forms were prepared as shown in Table 2. The low dose is designed to treat patients with early stage bradycardia; the middle dose is designed to treat symptomatic sinus patients; and the high dose is designed to treat severe symptomatic sinus patients or Atrio-Ventricular block patients.

TABLE 2

4-API Compositions

| API | Low Dose (mg) | Middle Dose (mg) | High Dose (mg) |
|---|---|---|---|
| Theophylline (or an isotopic variant thereof) (API-1) | 3.2-28.8 | 28.8-80 | 80-192 |
| Nifedipine (or an isotopic variant thereof) (API-2) | 0.16-2.88 | 1.44-12 | 4-38.4 |
| Betahistine $(HCl)_2$ (or an isotopic variant thereof) (API-3) | 0.4-10.8 | 3.6-40 | 10-120 |
| Levalbuterol HCl (or an isotopic variant thereof) (API-4) | 0.03-1.08 | 0.27-3.8 | 0.75-9 |

Example 8

Cardiovascular Evaluation of 4-API Compositions in Healthy Volunteers

To evaluate the cardiovascular effects of the 4-API compositions described in Example 7 above, two healthy volunteer subjects were participated. To obtain heart rate (HR) base lines, the two volunteer subjects were measured for heart rates, without any medication, daily at 7:00, 10:00, and 18:00 in a sitting position, quiet and resting for 10 minutes before each measurement, recording HR once per each time point (3 time points per day) for 3 consecutive days.

The average of all measurements was calculated as a baseline HR for each volunteer. Several oral formulations were tested. Each volunteer received a formulation orally 3 times daily at 7:00, 15:00, and 22:00; and each time 2 capsules were taken. The dosing range was in the middle of Table 2 above. The medication was administered to each volunteer for 3 consecutive days. The HR was measured at the same time points as for the base-line HR record. Then the average HR of each volunteer subject was calculated and recorded. To avoid carry-over medication interference or influence on the next medication, both volunteer subjects waited 7 days without any medication after completing each type of formulation. The results are summarized in Tables 3 to 5 below.

TABLE 3

Baseline Heart Rates of Healthy Volunteer Subjects

| Daily Record | | Subject 1 (BPM) | Subject 2 (BPM) | HR Average (BPM) |
|---|---|---|---|---|
| First Day | 7 am | 58 | 57 | 64 |
| | 10 am | 61 | 72 | |
| | 6 pm | 66 | 71 | |
| Second Day | 7 am | 56 | 59 | 62 |
| | 10 am | 58 | 72 | |
| | 6 pm | 62 | 65 | |
| Third Day | 7 am | 56 | 57 | 63 |
| | 10 am | 61 | 67 | |
| | 6 pm | 63 | 72 | |
| HR Average (BPM) | | 60 | 66 | 63 |

TABLE 4

Heart Rates of Healthy Volunteer Subjects Treated with Placebo

| Daily Record | | Subject 1 (BPM) | Subject 2 (BPM) | HR Average (BPM) |
|---|---|---|---|---|
| First Day | 7 am | 56 | 55 | 60 |
| | 10 am | 61 | 71 | |
| | 6 pm | 59 | 58 | |
| Second Day | 7 am | 55 | 57 | 61 |
| | 10 am | 60 | 60 | |
| | 6 pm | 63 | 69 | |
| Third Day | 7 am | 57 | 58 | 62 |
| | 10 am | 60 | 66 | |
| | 6 pm | 61 | 70 | |
| HR Average (BPM) | | 59 | 63 | 61 |

TABLE 5

Heart Rates of Healthy Volunteer Subjects Treated with the Developed Pharmaceutical Composition

| | Daily Record | Subject 1 (BPM) | Subject 2 (BPM) | HR Average (BPM) |
|---|---|---|---|---|
| First Day | 7 am | 52 | 58 | 73 |
| | 10 am | 85 | 88 | |
| | 6 pm | 73 | 82 | |
| Second Day | 7 am | 68 | 74 | 82 |
| | 10 am | 81 | 98 | |
| | 6 pm | 81 | 90 | |
| Third Day | 7 am | 69 | 75 | 82 |
| | 10 am | 82 | 97 | |
| | 6 pm | 80 | 90 | |
| HR Average (BPM) | | 75 | 84 | 79 |

As shown in Table 4, there was no significant change in heart rate (HR) compared to the baseline measurement of beat per min (BPM) when treated with a placebo. However, as shown in above Table 5, the heart rates are increased 15 BPM for volunteer 1 and 18 BPM for volunteer 2 when treated with the 4-API compositions.

Example 9

Cardiovascular Evaluation of 4-API Combinations in Bradycardia Patients

4-API combinations shown in Example 3 were evaluated on bradycardia patients. The results are summarized in Table 5 below. The bradycardia patients treated with a 4-API combination experienced disappearance or lessening of symptoms of bradycardia, including chest pains, chest tightness, confusion or memory problems, dizziness, fatigue, shortness of breach, and syncope.

TABLE 6

Patients Treated with 4-API Combinations

| Gender (Age) | Cardiovascular Symptom Before Treatment (ECG, HR, etc.) | Pre-Treatment HR (BPM) | Post-Treatment HR (BPM) |
|---|---|---|---|
| Female (65) | In 5 years, often feeling chest tightness, palpitations dizziness and seizure amaurosis fugax in recent two weeks, collapsed with sudden loss of consciousness during talking one hour ago and sent to hospital. Sinus rhythm ECG shows, daytime heart rate 45-54 BPM, at night 28-46 BPM, maximum R-R Spacing 2.5 Second, V5 Lead ST Move down 0.8 mm, Diagnosis of coronary artery disease, sick sinus syndrome, adams-stokes syndrome. Treatment: daily intravenous hydrogenated to cortisone 200 mg; Oral taking ubidecarenone, aminophylline, atropine, and nicotinamide. Continuous administration for 7 Days, still have seizures amaurosis fugax attach, illness without obvious improvement | 45-54 (day) 28-46 (night) | 69(day) 61(night) |
| Female (59) | Because of heart palpitations dizziness fatigue, Collapsed convulsions happened within a month and then hospitalized. Third-degree A-V block, ventricular rate 37 beats/minutes. Diagnosis of coronary heart disease, complete A-V block, adams-stokes syndrome. Treatment: daily intravenous infusion isoprenaline; Oral atropine, aminophylline, nicotinamide, After continuous treatment for 10 days, ECG showed the ventricular rate was 36 BPM. Patients couldn't get out of bed, and had coma twitch during these days. Doctors' consultation recommended the immediate placement of pacemakers, but pacemaker was refused by the patient and her families. | 36-37 | 54 |
| Male (43) | Dizziness, memory loss and physical decline for over a year, the outer Court Holter Report: two two-sinus block, sinus stationary, and escape, and the slowest heart rate 25 BPM, SNRT 4200 ms, diagnosed with SS syndrome, Used anisodamine, nicotinamide, dexamethasone, and taking Chinese medicine Xin Bao for a long time, the effect is not obvious. Patient was unwilling to accept the pacemaker, and come from laiwu city, Shandong province to Beng hospital for treatment. At time of receiving, ECG Report: HR 45 BPM. | 25-45 | 61 |
| Male (67) | Chest tightness, dizziness for more than a month, syncope for once. Holter inspection report: junctional rhythm. The slowest HR 32 BPM. 24 hours' average HR: 45, diagnosis with SS syndrome. There is no response by treatment with atropine, and nicotinamide. | 32-45 | 63. |
| Male (61) | Dizziness fatigue for more than one year. ECG Shows an A-V block, ventricular rate 38 BPM. 10 days' treatment with dexamethasone, nicotinamide, vitamin $B_2$, and atropine was ineffective. | 38 | 45 |
| Male (59) | Suddenly collapsed while working in the Office and patient was hospitalized. ECG shown sinus rhythm, HR 41 BPM, esophageal pacing SNRT 1860 ms, SACT430 ms, Diagnosed with SS syndrome. No obvious effect by treatment with atropine, and nicotinamide. Because of dry mouth in patients and dysuria, patient can't tolerate with atropine. | 41 | 71. |
| Female (45) | Sluggish chest tightness, palpitations for 3 years, getting worse for more than a month, and sometimes dizziness, occasional fainting. ECG shows sinus bradycardia and arrhythmia, HR 36 BPM, diagnosis with SS syndrome. No effect by treatment with atropine, and/or some traditional medicine. | 36 | 63 |
| Male (48) | Because of dizziness, tightness in the chest and could not stand. Patient was hospitalized 3 hours later, ECG report: sinus rhythm, HR was between 26 to 44 BPM. Diagnosed with SS syndrome and acute myocarditis. There is no obvious effect after treatment with IV isoprenaline, or oral administration of atropine. | 26-44 | 71 |

TABLE 6-continued

Patients Treated with 4-API Combinations

| Gender (Age) | Cardiovascular Symptom Before Treatment (ECG, HR, etc.) | Pre-Treatment HR (BPM) | Post-Treatment HR (BPM) |
|---|---|---|---|
| Male (73) | Tightness in the chest, swelling of lower extremities, bradycardia for 2 years. ECG shown sinus rhythm, and HR was 51 BPM. Paroxysmal junctional escape rhythm HR was 41 BPM. Myocardial strain and second degree atrioventricular block. Diagnose as SS syndrome. There is no obvious effect after treatment with isosorbide, atropine, and nicotinamide. | 41-51 | 71 |
| Male (63) | Palpitation chest tightness, dizziness, lacking in strength for half a month and was hospitalized. ECG shows sinus bradycardia and arrhythmia, HR between 41 and 50 BPM, second degree type of sinus block, Junctional escape beat, diagnosed as SS syndrome. There is no obvious effect after treatment with isosorbide, and nicotinamide. | 41-50 | 68 |
| Female (41) | Sluggish chest tightness, palpitations and lacking in strength for 3 years. Patient was hospitalized because of dizziness and passed out. ECG shows sinus bradycardia and HR 36 BPM, sinus arrest, and junctional escape. Holter reported RR interval ≥2 seconds 13 times and maximum interval 2.6 seconds. Patient was diagnosed with SS syndrome. There is no obvious effect after treatment with isosorbide, Nifedipine, nicotinamide, and atropine. Patient is still sick in bed. | 36 | 73 |
| Male (67) | Fatigue and dizziness for 2 years. The patient was diagnosed as coronary heart disease by Heilongjiang provincial hospital. ECG shows an A-V block and the ventricular rate 39 BPM. Treatment with nitroglycerin, and nicotinamide is ineffective. Provincial hospital recommended placing cardiac pacemaker. Patient is unwilling to use the pacemaker. | 39 | 51 |
| Female (51) | Chest tightness, dizziness and feeling fatigue for more than a year. The Holter report showed the slowest HR 35 BPM, due to high grade A-V block. The slowest ventricular rate was 28 BPM. There is no improvement after treatment with aminophylline, and nicotinamide. Doctors suggest using pacemaker. As a hospital director, the patient didn't want to use the pacemaker. | 28-35 | 56 |
| Female (35) | Dizziness and fatigue for more than two years. ECG shown HR between 35 to50 BPM. Patient was diagnosed as SS syndrome by a Hospital of Cardiology. There is no improvement after treatment with atropine and nicotinamide. The pacemaker was suggested to patients but was refused. | 35-50 | 61 |
| Female (53) | Dizziness and fatigue for more than two years. ECG shown HR between 44 and 48 BPM, arrhythmias, and frequent atrial premature beats. There is no obvious effect after treatment with oxyfedrine, prednisone, and nicotinamide, etc. The patient felt no improvement. | 44-48 | 63. |
| Male (52) | Dizziness and weakness. Slow HR for 5 years. Ineffective treatment in a few hospitals. Patient was diagnosed as SS syndrome by a hospital. ECG shown HR 39 BPM. Doctor recommends pacemaker but was refused by the patient. | 39 | 63 |
| Female (42) | Palpitation chest tightness, dizziness and fatigue for more than 3 years. The Holter examination results: During 24 hours, the fastest HR 49 BPM, and the slowest HR 39 BPM, the longest RR interval was 2.6 seconds, diagnosed as SS syndrome. There is no obvious effect after treatment with atropine, nicotinamide, dexamethasone, intravenous injection of fructose diphosphate. When the patient came to the hospital, ECG shown HR41 BPM. | 39-49 | 64 |
| Female (29) | Palpitation, shortness of breath, and fatigue for 5 years. ECG shown an A-V block and the ventricular rate 41 BPM. There is no obvious effect after treatment with atropine, dexamethasone, and energy agents. Hospital recommended a pacemaker but the patient refused. When the patient arrived the hospital, ECG shown an A-V block and HR was 39 BPM. | 39-41 | 54. |
| Female (25) | Palpitation and shortness of breath for 2 years. Holter examination shown an A-V block. The ventricular rate was 34 BPM. The hospital suggested that the drug treatment won't have the effect in this case and recommended the use of pacemaker. Patients was unwilling to place a pacemaker. When the patient arrived our hospital, ECG shown ventricular rate was 33 BPM. | 33-34 | 47 |
| Male (58) | Palpitation, shortness of breath, and fatigue for 5 years. The hospital diagnosed as rheumatic heart disease, mitral insufficiency, left atrial and right ventricular enlargement. Holter examination report: atrial fibrillation, A-V block, the slowest ventricular rate31 BPM, the fastest 48 BPM, average41 BPM. Recommended placement of pacemakers but refused by the patient. When the patient arrived our hospital, ECG shown atrial fibrillation and ventricular rate 38 BPM. | 31-38 | 58 |

Example 10

Clinical Evaluation of 4-API Compositions in Symptomatic Sinus Bradycardia Patients An open-label, single ascending dose study is conducted to establish the safety and tolerability of 4-API compositions (shown in Table 2 above) in symptomatic sinus bradycardia patients. Patients with peptic ulcer disease, seizure disorder, or cardiac arrhythmia are excluded. Patients with asthma who are taking a beta-agonist and/or theophylline are also excluded.

About 18 patients between 18 to 80 years and with an average heart rate of ≤50 bpm are divided into six cohorts without randomization. Each cohort has 3-4 symptomatic sinus bradycardia patients. Each patient receives orally a 4-API composition described in Example 7.

On the day of dosing, the patents are monitored for 2 hours with a Holter monitor to establish a baseline. Immediately after the dosing, the patients are monitored continually with a Holter monitor for at least 22 hours. A 12-lead electrocardiogram is also taken for each patient prior to discharge.

The study starts with the lowest dose. The initial cohort is enrolled in a staggered manner to identify any blood pressure or heart rate effects. Specifically, the study starts with only one patient on the first day of dosing. If there are no significant adverse events observed in the first patient 24 hours after the dosing as monitored by a Holter monitor and 12-lead ECG, the second patient is enrolled 24 hours after the first patient, and the third patient is enrolled 24 hours after the second patient, and so forth. Each patient in a cohort is monitored for additional 7-days for clinical safety.

Standard clinical evaluation and objective measures are employed to monitor and assess safety during the study. Safety and tolerability assessments for all the patients include adverse events (AEs), physical examinations, vital signs (systolic/diastolic blood pressure, heart rate, respiratory rate, and temperature), clinical laboratory tests, digital Holter monitoring Data (ECGs), and local tolerability rating scales.

If there is little or no effect observed in the first cohort, the dose is increased to the next level. Once effects on heart rate and blood pressure are observed, the dose is increased in a smaller step to ensure the dose is safe for the patients. A patient may participate in more than one dose level study after a ≥7-day washout period. The high dose is designed for atrioventricular block bradycardia patients and may not be used in this study for sinus bradycardia patients.

The examples set forth above are provided to give those of ordinary skill in the art with a complete disclosure and description of how to make and use the embodiments and are not intended to limit the scope of the disclosure. Modifications of the above-described modes for carrying out the disclosure that are obvious to persons of skill in the art are intended to be within the scope of the following claims. All publications, patents, and patent applications cited in this specification are incorporated herein by reference as if each such publication, patent, or patent application were specifically and individually indicated to be incorporated herein by reference.

What is claimed is:

1. A method of treating or ameliorating bradycardia in a subject, comprising:
   administering to the subject in need thereof a therapeutically effective amount of the pharmaceutical composition comprising:
   (i) theophylline or aminophylline 3.2-192 mg/dose;
   (ii) nifedipine 0.16-38.4 mg/dose;
   (iii) betahistine 0.4-120 mg/dose;
   (iv) levalbuterol or albuterol 0.03-9 mg/dose; and
   (v) a pharmaceutically acceptable excipient; and
   wherein the pharmaceutical composition is formulated in a dosage form for oral, intravenous, intramuscular administration.

2. A method of treating or ameliorating bradycardia in a subject, comprising:
   administering to the subject in need thereof a therapeutic effective amount of the pharmaceutical composition comprising:
   (a) any three compounds, wherein each compound is independently
      (i) theophylline or aminophylline 3.2-192 mg/dose;
      (ii) a nifedipine 0.16-38.4 mg/dose;
      (iii) betahistine or a metabolite thereof 0.4-120 mg/dose;
      (iv) levalbuterol or albuterol 0.03-9 mg/dose; and
      (v) a pharmaceutically acceptable excipient; and
   wherein the pharmaceutical composition is formulated in a liquid or solid dosage form for oral, intravenous, intramuscular administration.

3. The method of claim 1, wherein the amount of theophylline or aminophylline administered comprises from about 9.6 to about 576 mg per day.

4. The method of claim 1, wherein the amount of nifedipine administered comprises from about 0.48 to about 115.2 mg per day.

5. The method of claim 1, wherein the amount of betahistine administered comprises from about 1.2 to about 360 mg per day.

6. The method of claim 1, wherein the amount of levalbuterol or albuterol administered comprises from 0.09 to about 27 mg per day.

7. The method of claim 1, wherein the pharmaceutical composition is formulated as a liquid dosage form, or semiliquid dosage form, or a solid dosage form of tablets or capsules.

8. The method of claim 1, wherein the pharmaceutical composition is formulated for multiple-dose per day by an immediate release, or two-dose per day by a controlled release, or single dose per day by a modified or extended-release.

9. The method of claim 1, wherein the method increases heart rate and/or cardiac output, and/or cerebral blood flow in a subject comprising administering to the subject in need thereof an effective amount of a pharmaceutical composition of (i) theophylline or aminophylline, (ii) nifedipine, (iii) betahistine, (iv) levalbuterol or albuterol, and (v) a pharmaceutically acceptable excipient; and wherein the pharmaceutical composition is formulated in a dosage form for oral, or intravenous, or intramuscular administration.

10. The method of claim 1, wherein the cardiovascular disease is bradycardia, chronic bradycardia (heart rate <60 beats per minute), that is caused by the sickness of either sinus, or atrial, or ventricular, or atrioventricular block.

* * * * *